United States Patent
Ishii

(10) Patent No.: US 10,501,737 B2
(45) Date of Patent: Dec. 10, 2019

(54) METHOD FOR PRODUCING ANTIGEN-BINDING MOLECULE USING MODIFIED HELPER PHAGE

(71) Applicant: CHUGAI SEIYAKU KABUSHIKI KAISHA, Tokyo (JP)

(72) Inventor: Shinya Ishii, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 294 days.

(21) Appl. No.: 15/024,692

(22) PCT Filed: Sep. 30, 2014

(86) PCT No.: PCT/JP2014/076001
§ 371 (c)(1),
(2) Date: Mar. 24, 2016

(87) PCT Pub. No.: WO2015/046554
PCT Pub. Date: Apr. 2, 2015

(65) Prior Publication Data
US 2016/0264960 A1    Sep. 15, 2016

(30) Foreign Application Priority Data
Sep. 30, 2013  (JP) .................. 2013-203528

(51) Int. Cl.
*C40B 50/06* (2006.01)
*C12N 15/10* (2006.01)
(Continued)

(52) U.S. Cl.
CPC .......... *C12N 15/1037* (2013.01); *C07K 16/00* (2013.01); *C12N 7/00* (2013.01); *C12N 15/86* (2013.01); *C07K 2317/31* (2013.01); *C12N 2795/00051* (2013.01); *C12N 2795/14131* (2013.01); *C12N 2795/14143* (2013.01); *C40B 50/06* (2013.01)

(58) Field of Classification Search
None
See application file for complete search history.

(56) References Cited

U.S. PATENT DOCUMENTS

2006/0159673 A1  7/2006 Kojima
2010/0146647 A1  6/2010 Logtenberg et al.

FOREIGN PATENT DOCUMENTS

EP   1 264 885 A1   12/2002
JP   H06-508511 A    9/1994
(Continued)

OTHER PUBLICATIONS

Baek, H., et al., "An improved helper phage system for efficient isolation of specific antibody molecules in phage display," *Nucleic Acids Research* 30(5):e18, Oxford University Press, United Kingdom (2002).
(Continued)

*Primary Examiner* — Christian C Boesen
(74) *Attorney, Agent, or Firm* — Nixon & Vanderhye P.C.

(57) ABSTRACT

The present invention provides a method for preparing a bacteriophage displaying an antigen-binding molecule, comprising the step of contacting a helper phage capable of expressing a first polypeptide with a bacterium capable of expressing a second polypeptide, wherein the first polypeptide and the second polypeptide associate with each other to form the antigen-binding molecule.

14 Claims, 11 Drawing Sheets
Specification includes a Sequence Listing.

(51) Int. Cl.
C12N 15/86 (2006.01)
C07K 16/00 (2006.01)
C12N 7/00 (2006.01)

(56) References Cited

FOREIGN PATENT DOCUMENTS

| JP | 2002-517186 A | 6/2002 |
|---|---|---|
| JP | 2004-502428 A | 1/2004 |
| JP | 2007-510738 A | 4/2007 |
| WO | WO 92/20791 A1 | 11/1992 |
| WO | WO 96/27011 A1 | 9/1996 |
| WO | WO 98/50431 A2 | 11/1998 |
| WO | WO-9962944 A | 12/1999 |
| WO | WO 01/62907 A1 | 8/2001 |
| WO | WO-0202773 A | 1/2002 |
| WO | WO 2004/065611 A1 | 8/2004 |
| WO | WO-2005/046723 A | 5/2005 |
| WO | WO 2006/106905 A1 | 10/2006 |
| WO | WO 2008/119353 A1 | 10/2008 |
| WO | WO 2009/080251 A1 | 7/2009 |
| WO | WO 2009/108406 A2 | 9/2009 |
| WO | WO 2011/097603 A1 | 8/2011 |
| WO | WO 2012/023053 A2 | 2/2012 |
| WO | WO 2013/081143 A1 | 6/2013 |

OTHER PUBLICATIONS

Beiboer, S.H.W., et al., "Guided Selection of a Pan Carcinoma Specific Antibody Reveals Similar Binding Characteristics yet Structural Divergence Between the Original Murine Antibody and its Human Equivalent," *J. Mol. Biol.* 296:833-849, Academic Press, United States (2000).

Brockmann, E.-C., et al., "Synthetic single-framework antibody library integrated with rapid affinity maturation by $V_L$ shuffling," *Protein Engineering, Design & Selection* 24(9):691-700, Oxford University Press, United Kingdom (2011).

Davis, J.H., et al., "SEEDbodies: fusion proteins based on strand-exchange engineered domain (SEED) $C_H3$ heterodimers in an Fc analogue platform for asymmetric binders or immunofusions and bispecific antibodies," *Protein Engineering, Design & Selection* 23(4):195-202, Oxford University Press, United Kingdom (2010).

Hur, B.-u., et al., "Development of the dual-vector system-III (DVS-III), which facilitates affinity maturation of a Fab antibody via light chain shuffling," *Immunology Letters* 132:24-30, Elsevier B.V., Netherlands (2010).

Jackman, J., et al., "Development of a Two-part Strategy to Identity a Therapeutic Human Bispecific Antibody That Inhibits IgE Receptor Signaling," *Journal of Biological Chemistry* 285(27):20850-20859, The American Society for Biochemistry and Molecular Biology, Inc., United States (2010).

Kim, S.J., et al., "Antibody Engineering for the Development of Therapeutic Antibodies," *Mol. Cells* 20(1):17-29, The Korean Society for Molecular and Cellular Biology, Korea (2005).

Kramer, R.A., et al., "A novel helper phage that improves phage display selection efficiency by preventing the amplification of phages without recombinant protein," *Nucleic Acids Research* 31(11):e59, Oxford University Press, United Kingdom (2003).

Lu, T.K., and Collins, J.J., "Engineered bacteriophage targeting gene networks as adjuvants for antibiotic therapy," *PNAS* 106(12):4629-4634, National Academy of Sciences, United States (2009).

Merchant, A.M., et al., "An efficient route to human bispecific IgG," *Nature Biotechnology* 16:677-681, Nature Publishing Group, United Kingdom (1998).

Pavlou, A.K., and Belsey, M.J., "The therapeutic antibodies market to 2008," *European Journal of Pharmaceutics and Biopharmaceutics* 59:389-396, Elsevier B.V., Netherlands (2005).

Reichert, J.M., et al., "Monoclonal antibody successes in the clinic," *Nature Biotechnology* 23(9):1073-1078, Nature Publishing Group, United Kingdom (2005).

Ridgway, J.B.B., et al., "'Knobs-into-holes' engineering of antibody $C_H3$ domains for heavy chain heterodimerization," *Protein Engineering* 9(7):617-621, Oxford University Press, United Kingdom (1996).

Rondot, S., et al., "A helper phage to improve single-chain antibody presentation in phage display," *Nature Biotechnology* 19:75-78, Nature Publishing Group, United Kingdom (2001).

Sampei, Z., et al., "Identification and Multidimensional Optimization of an Asymmetric Bispecific IgG Antibody Mimicking the Function of Factor VIII Cofactor Activity," *PLOS ONE* 8(2):e57479, Public Library of Science, United States (2013).

Smith, G.P., and Scott, J.K., "Libraries of Peptides and Proteins Displayed on Filamentous Phage," *Methods in Enzymology* 217:228-257, Academic Press, Inc., United States (1993).

Suresh, M.R., et al., "Bispecific Monoclonal Antibodies from Hybrid Hybridomas," *Methods in Enzymology* 121:210-228, Academic Press, Inc., United States (1986).

International Search Report for International Application No. PCT/JP2014/076001, Japanese Patent Office, Japan, dated Dec. 22, 2014.

Unverified English translation of WO 2004/065611, cited as document FP5 on SB/08a, 20 pages.

Unverified English translation of WO 2006/106905, cited as document FP6 on SB/08a, 123 pages.

Unverified English translation of WO 2013/081143, cited as document FP12 on SB/08a, 293 pages.

Guo, Y., et al., "Construction of bifunctional phage display for biological analysis and immunoassay," *Analytical Biochemistry* 396:155-157, Elsevier Inc., Netherlands (2010).

Wang, K.C., et al., "Adapter-Directed Display: A Modular Design for Shuttling Display on Phage Surfaces," *J. Mol. Biol.* 395:1088-1101, Elsevier Ltd., Netherlands (2010).

METHOD FOR PRODUCING ANTIGEN-BINDING MOLECULE USING MODIFIED HELPER PHAGE

TECHNICAL FIELD

Related Application

The present patent application claims the priority based on Japanese Patent Application No. 2013-203528 filed on Sep. 30, 2013, the content of which is incorporated herein by reference in their entirety.

REFERENCE TO SEQUENCE LISTING SUBMITTED ELECTRONICALLY

The content of the electronically submitted sequence listing (Name: 21440750001sequence.txt; Size: 186 KB; and Date of Creation: Mar. 24, 2016) filed with the application is incorporated herein by reference in its entirety.

In one aspect, the present invention relates to, for example, a method for preparing a bacteriophage displaying an antigen-binding molecule.

BACKGROUND ART

Antibodies have received attention as drugs because of having high stability in plasma and producing few adverse reactions. Among others, many IgG-type antibody drugs have been launched, and a large number of antibody drugs are also currently under development (Non Patent Literatures 1 and 2). Meanwhile, various techniques have been developed as techniques applicable to second generation antibody drugs. For example, techniques of improving effector functions, the ability to bind to antigens, pharmacokinetics, or stability or reducing immunogenic risks have been reported (Non Patent Literature 3).

In recent years, multispecific antibodies such as bispecific antibodies (BsAbs) have received attention as one of methods for highly functionalizing antibodies. BsAb is one kind of multivalent antibody capable of binding to two types of antigens by possessing, in one molecule, sites capable of binding to two different antigenic determinants (epitopes).

BsAb typically comprises two types of H chains and two types of L chains. A problem associated with the production of BsAb is that when these H chains and L chains are transferred to one cell and expressed therein, immunoglobulin H chains are combined with immunoglobulin L chains at random, possibly producing 10 different types of antibody molecules (Non Patent Literature 4 and Patent Literature 1). Of these 10 types of antibodies produced, an antibody having desired bispecificity is only one type of antibody constituted by a combination of two H chain-L chain pairs differing in binding specificity in which each H chain is correctly combined with each L chain.

Methods for efficiently heterodimerizing produced H chains are known as methods to solve such a problem. Examples of such known methods include: a method which involves introducing structures sterically complementary to each other to two CH3 domains (Non Patent Literature 5 and Patent Literature 2); a method which exploits the properties of IgG and IgA CH3 domains of not binding to each other and involves converting two CH3 domains only to a desired heterodimer by interdigitating an IgG-derived sequence and an IgA-derived sequence (SEEDbodies: Non Patent Literature 6); and a method which involves promoting heterodimerization through the use of the charge interaction between two H chains by introducing a mutation to their CH3 domains (Patent Literature 3).

Unfortunately, the H chains produced by these methods still may pair with wrong L chains. Accordingly, methods for producing a multispecific antibody having common L chains while promoting the heterodimerization of H chains have been reported. Examples of known methods for obtaining common L chains include: a method for obtaining common L chains by preparing a library of L chains, sequentially combining each L chain of the library with H chains of two antibodies, and screening for an antibody capable of binding to their respective antigens (Patent Literature 4); a method which involves obtaining antibodies binding to different antigens from an antibody library having a limited repertoire of L chains, and selecting antibodies having identical L chains from among the obtained antibodies (Non Patent Literature 7 and Patent Literature 1); a method which involves preparing chimeric L chains by the shuffling of CDRs of two types of antibody L chains, and screening for common L chains capable of binding to both antigens (Non Patent Literature 8); a method for obtaining an antibody having common L chains by immunizing a transgenic mouse harboring a particular L chain gene (Patent Literatures 5 and 6); and a method for obtaining an antibody having common L chains by obtaining antibodies binding to different antigens from an antibody library containing a particular L chain gene and having diverse H chains (Non Patent Literature 14).

Alternative examples of such known methods include: a method for promoting selective heterodimerization by altering H chain and L chain constant regions (Patent Literature 3); a method for preparing only a desired heterodimer by H chain variable region/L chain variable region (VH/VL) or H chain constant region CH1/L chain constant region (CH1/CL) crossover (Crossmab: Patent Literature 7); and a method for preparing a bispecific antibody by preparing two types of antibodies, followed by in vitro disulfide bond isomerization (DuoBody: Patent Literature 8).

Furthermore, a method which involves obtaining antibodies against various antigens using a common H chain library and an L chain library, and then preparing a bispecific antibody from common H chains and two types of L chains (κ chain and λ chain) is known (Kappa-Lambda Body: Patent Literature 11) in relation to a method for obtaining common H chains.

Alternatively, antibodies that recognize different epitopes on the same antigen are obtained and may be used in a bispecific antibody (particularly, biparatopic antibody). Upon antigen binding of the biparatopic antibody, even single antigens can be cross-linked by the biparatopic antibody to form an immune complex (IC). The in vivo formation of this immune complex is expected to offer the rapid clearance of the immune complex from blood (Patent Literature 9).

Meanwhile, phage display technology is increasingly adopted widely as one of methods for obtaining antigen-binding molecules. The phage display technology is a technique of displaying, for example, H chain variable regions and L chain variable regions of antibodies on the particles of bacteriophages. A population of many bacteriophages displaying antibodies differing in sequence (phage antibody library) was prepared by use of this technique, and an antibody binding to an arbitrary antigen can be selected (picked) from the library to obtain an antibody specifically binding to the desired antigen.

The phages used in the phage display technology are typically filamentous phages M13. The antibody display on phage particles can usually be carried out by inserting an antibody H chain variable region gene and L chain variable region gene linked to a gene encoding a phage coat protein such as g3p to phagemid vectors, and transferring the phagemid vectors to *E. coli*, which is then infected with a helper phage. For antibody screening from the phage antibody library, the antibody library is mixed with an immobilized antigen, and a phage displaying an antibody capable of binding to the antigen can be selected (picked) by binding, washing and elution procedures (panning). The recovered phage can be amplified by the infection of a host such as *E. coli*. The phage thus amplified can be used in repeated panning to thereby enhance the ratio of the antibody specifically binding to the antigen (Non Patent Literature 9).

In order to obtain an antibody fragment by the phage display method, an antibody library is usually prepared in the form of a fusion protein of Fab or single-chain Fv (scFv) and a phage coat protein. Although phage vectors containing the whole gene information of bacteriophages were initially used, current methods generally employ phagemid vectors. The phagemid vectors are plasmid vectors smaller in size than phage vectors. A gene encoding a protein to be displayed is linked to the end (which corresponds to the N terminus) of a gene encoding a phage coat protein, such as gene 3 or gene 8, and the resulting gene is inserted to phagemid vectors. In the phage display method, the gene encoding a protein to be displayed must be packaged in a phage particle. Therefore, a phage packaging signal needs to reside on the phagemid vectors. In addition, phage production from *E. coli* containing the phagemid vector requires infecting the *E. coli* with a helper phage, such as M13KO7 or VCSM13, which supplies a phage structural protein or the like.

Chain shuffling may be used as a method for identifying an antibody fragment having high affinity for a target antigen using the phage antibody library thus prepared. In this method, for example, a polynucleotide encoding an antigen-binding site (e.g., L chain variable region) of an antibody is diversified by random or site-directed mutagenesis, while a polynucleotide encoding another antigen-binding site (e.g., H chain variable region) of the antibody is fixed. This can be achieved, for example, by cloning a wild-type polynucleotide encoding the H chain variable region of an antibody binding to the target antigen, into a phage display vector system having a library of the diversified L chain variable region polynucleotides, and subsequently screening for an antibody binding with high affinity to the antigen. Typically, the H chain variable region is first fixed, while the L chain variable regions are shuffled. Examples of methods for affinity maturation of an antibody using such L chain shuffling may include: an approach using dual-vector system-III (DVS-III) composed of a set of a pLf1T-3 (L chain) phagemid vector and pHg3A-3 (H chain-gene 3) plasmid (Non Patent Literature 15); and an approach which involves carrying out panning operation for an antigen using a phage display library of H chain variable regions, and then carrying out panning operation again using the H chain variable regions thus enriched by panning operation in combination with VL genes in a library (Non Patent Literature 16).

The phage display method is also used as means to humanize a non-human animal-derived antibody binding to a target antigen. For example, human-derived antibody L chains are obtained by panning operation for an antigen using fixed H chains of an antibody obtained by mouse immunization and a human naive-derived L chain antibody library in combination. Subsequently, a human-derived antibody H chain can be further obtained by panning operation again for the antigen using the fixed L chains and a human naive-derived H chain antibody library in combination. In this way, a human antibody can be obtained on the basis of the non-human animal-derived antibody by the sequential replacement with the human antibody libraries (Non Patent Literature 17).

There are some reports on phage display modified by altering genes of helper phages. For example, Hyper phage (Non Patent Literature 10), CT helper phage (Non Patent Literature 11), and Ex-phage (Non Patent Literature 12) are known. The transfer of a gene encoding a substance inhibiting a drug resistance gene has been reported as an example of the transfer of a foreign gene to the genome of a bacteriophage (Non Patent Literature 13 and Patent Literature 10). However, none of the previous reports disclose the construction of a novel phage display method suitable for obtaining antibodies having common L chains or H chains by the alteration of a helper phage.

CITATION LIST

Patent Literature

Patent Literature 1: WO98/50431
Patent Literature 2: WO96/27011
Patent Literature 3: WO2006/106905
Patent Literature 4: WO2004/065611
Patent Literature 5: WO2011/097603
Patent Literature 6: US2010/0146647
Patent Literature 7: WO2009/080251
Patent Literature 8: WO2008/119353
Patent Literature 9: WO2013/081143
Patent Literature 10: WO2009/108406
Patent Literature 11: WO2012023053

Non Patent Literature

Non Patent Literature 1: Nat Biotechnol (2005) 23, 1073-1078
Non Patent Literature 2: Eur J Pharm Biopharm (2005) 59, 389-396
Non Patent Literature 3: Mol Cells (2005) 20, 17-29
Non Patent Literature 4: Methods Enzymol (1986) 121, 210-228
Non Patent Literature 5: Protein Eng (1996) 9, 617-621
Non Patent Literature 6: Protein Eng Des Sel (2010) 23, 195-202
Non Patent Literature 7: Nat Biotechnol (1998) 16, 677-681
Non Patent Literature 8: PLoS One (2013) 8, e57479
Non Patent Literature 9: Methods Enzymol (1993) 217, 228-257
Non Patent Literature 10: Nat Biotechnol (2001) 19, 75-78
Non Patent Literature 11: Nucleic Acids Res (2003) 31, e59
Non Patent Literature 12: Nucleic Acids Res (2002) 30, e18
Non Patent Literature 13: Proc Natl Acad Sci USA (2009) 106, 4629-4634
Non Patent Literature 14: J Biol Chem. 2010 Jul. 2; 285 (27): 20850-9
Non Patent Literature 15: Immunol Lett. 2010 Aug. 16; 132 (1-2): 24-30
Non Patent Literature 16: Protein Eng Des Sel. 2011 September; 24 (9): 691-700
Non Patent Literature 17: J Mol Biol. 2000 Feb. 25; 296 (3): 833-49

SUMMARY OF INVENTION

Technical Problem

The present invention has been made in light of these circumstances. In one embodiment, an object of the present invention is to provide a novel method for efficiently obtaining a plurality of antigen-binding molecules each comprising two polypeptides, one of which is common polypeptides (first polypeptides) and the other of which is polypeptides (second polypeptides) different among the antigen-binding molecules.

Solution to Problem

The present inventor has conducted diligent studies on a method for efficiently preparing a plurality of antigen-binding molecules comprising common first polypeptides, and consequently found that, surprisingly, a bacteriophage displaying an antigen-binding molecule constituted by a first polypeptide and a second polypeptide can be prepared by preparing a helper phage capable of expressing the first polypeptide, and a bacterium capable of expressing the second polypeptide and infecting the bacterium with the helper phage. The present inventor has also found that in this approach, a population of bacteriophages displaying antigen-binding molecules (antigen-binding molecule display library) comprising first polypeptides having common amino acid sequences and second polypeptides differing in amino acid sequence can be prepared by preparing a bacterium population capable of expressing a plurality of second polypeptides differing in amino acid sequence and infecting the bacterium population with the helper phage capable of expressing the first polypeptide. The present inventor has further found that an antigen-binding molecule specifically binding to a desired antigen can be obtained from the antigen-binding molecule display library thus prepared. Moreover, the present inventor has found that antigen-binding molecules specifically binding to a plurality of antigens can each be obtained from the antigen-binding molecule display library, whereby a multispecific antigen-binding molecule specifically binding to the plurality of antigens can be prepared such that the multispecific antigen-binding molecule comprises antigen-binding molecules having common first polypeptides.

The present invention has been completed on the basis of these findings and specifically relates to, for example, the following embodiments:

[1] A method for preparing a bacteriophage displaying an antigen-binding molecule, comprising contacting a helper phage capable of expressing a first polypeptide with a bacterium capable of expressing a second polypeptide, wherein the first polypeptide and the second polypeptide associate with each other to form the antigen-binding molecule.

[2] The method according to [1], wherein a polynucleotide encoding the first polypeptide is inserted in the genome of the helper phage.

[3] The method according to [1] or [2], wherein the polynucleotide encoding the first polypeptide is functionally linked to a promoter.

[4] The method according to any one of [1] to [3], wherein the first polypeptide is fused with a phage coat protein.

[5] The method according to any one of [1] to [4], wherein the helper phage is M13KO7.

[6] The method according to any one of [1] to [5], wherein the bacterium comprises a polynucleotide encoding the second polypeptide.

[7] The method according to any one of [1] to [6], wherein the polynucleotide encoding the second polypeptide is inserted in a phagemid vector.

[8] The method according to any one of [1] to [7], wherein the second polypeptide is fused with a phage coat protein.

[9] The method according to any one of [1] to [8], wherein the antigen-binding molecule has antibody variable region(s).

[10] The method according to [9], wherein the first polypeptide and the second polypeptide are each selected from the group consisting of a polypeptide comprising an L chain variable region and a polypeptide comprising an H chain variable region, and differ from each other.

[11] The method according to [10], wherein the polypeptide comprising an L chain variable region is the polypeptide further comprising an L chain constant region, and/or the polypeptide comprising an H chain variable region is the polypeptide further comprising an H chain constant region.

[12] A method for preparing an antigen-binding molecule display library comprising common first polypeptides, wherein the method comprises:

(a) carrying out a method according to any one of [1] to [11] a plurality of times, wherein a plurality of bacteria used in the step are a bacterium population capable of expressing a plurality of second polypeptides differing in amino acid sequence, and helper phages used in the step are helper phages capable of expressing first polypeptides having identical amino acid sequences; and (b) recovering a plurality of bacteriophages displaying antigen-binding molecules prepared in (a).

[13] An antigen-binding molecule display library prepared by a method according to [12].

[14] A method for obtaining an antigen-binding molecule specifically binding to a predetermined antigen, wherein the method comprises:

(a) contacting the antigen with an antigen-binding molecule display library according to [13]; and (b) selecting an antigen-binding molecule binding to the antigen from the antigen-binding molecule display library.

[15] A method for preparing a multispecific antigen-binding molecule comprising common first polypeptides, wherein the method comprises:

(a) carrying out a method according to [14] for a plurality of antigens; and (b) preparing a multispecific antigen-binding molecule using a plurality of first polypeptides having identical amino acid sequences and a plurality of second polypeptides having different amino acid sequences, contained in a plurality of antigen-binding molecules obtained in (a), wherein the first polypeptides associate with the plurality of second polypeptides, respectively, to form the plurality of antigen-binding molecules specifically binding to the plurality of antigens.

[16] A method for preparing a multispecific antigen-binding molecule comprising common first polypeptides, wherein the method comprises:

(a) carrying out a method according to [14] for a plurality of antigens;

(b) for a plurality of first polypeptides having identical amino acid sequences and a plurality of second polypeptides having different amino acid sequences, contained in a plurality of antigen-binding molecules obtained in (a), separately preparing polynucleotides encoding the first polypeptides and polynucleotides encoding the plurality of second polypeptides;

(c) transferring each the polynucleotide prepared in (b) to a host cell; and (d) culturing the host cell of (c) to recover a multispecific antigen-binding molecule, wherein the first polypeptides associate with the plurality of second polypeptides, respectively, to form the plurality of antigen-binding molecules specifically binding to the plurality of antigens.

[17] The method according to [15] or [16], wherein the multispecific antigen-binding molecule is a bispecific antigen-binding molecule.

[18] A method for producing an antigen-binding molecule, wherein the method comprises:

(a) contacting helper phages capable of expressing first polypeptides having amino acid sequences identical to the amino acid sequence of a first polypeptide of a reference antigen-binding molecule (parent antigen-binding molecule), which comprises the first polypeptide and a second polypeptide associated with each other and is capable of specifically binding to a predetermined antigen, with a bacterium population capable of expressing second polypeptides having amino acid sequences different from the amino acid sequence of the second polypeptide of the parent antigen-binding molecule to prepare an antigen-binding molecule display library comprising a plurality of bacteriophages displaying antigen-binding molecules (child antigen-binding molecules) comprising the common first polypeptides associated with the second polypeptides differing in amino acid sequence, respectively; and (b) contacting the antigen with the antigen-binding molecule display library prepared in (a) to select a child antigen-binding molecule capable of specifically binding to the antigen.

[19] The method according to [18], wherein the method further comprises:

(d) contacting helper phages capable of expressing second polypeptides having amino acid sequences identical to the amino acid sequence of the second polypeptide of the child antigen-binding molecule obtained in (b) described in [18] with a bacterium population capable of expressing first polypeptides having amino acid sequences different from the amino acid sequence of the first polypeptide of the child antigen-binding molecule to prepare an antigen-binding molecule display library comprising a plurality of bacteriophages displaying antigen-binding molecules (grandchild antigen-binding molecules) comprising the common second polypeptides associated with the first polypeptides differing in amino acid sequence, respectively; and (e) contacting the antigen with the antigen-binding molecule display library prepared in (d) to select a grandchild antigen-binding molecule capable of specifically binding to the antigen.

[20] A combination of an altered helper phage and a bacterium infectible by the helper phage, wherein the helper phage is a helper phage capable of expressing a first polypeptide and the bacterium is a bacterium capable of expressing a second polypeptide, and the first polypeptide and the second polypeptide associate with each other to form an antigen-binding molecule.

[21] An altered helper phage capable of expressing a certain polypeptide, wherein the polypeptide is any one of two polypeptides that associate with each other to form an antigen-binding molecule.

[22] Those skilled in the art should understand that one of or any combination of two or more of the aspects described above is also included in the present invention unless a technical contradiction arises on the basis of the common technical knowledge of those skilled in the art.

DESCRIPTION OF EMBODIMENTS

Figure 1:
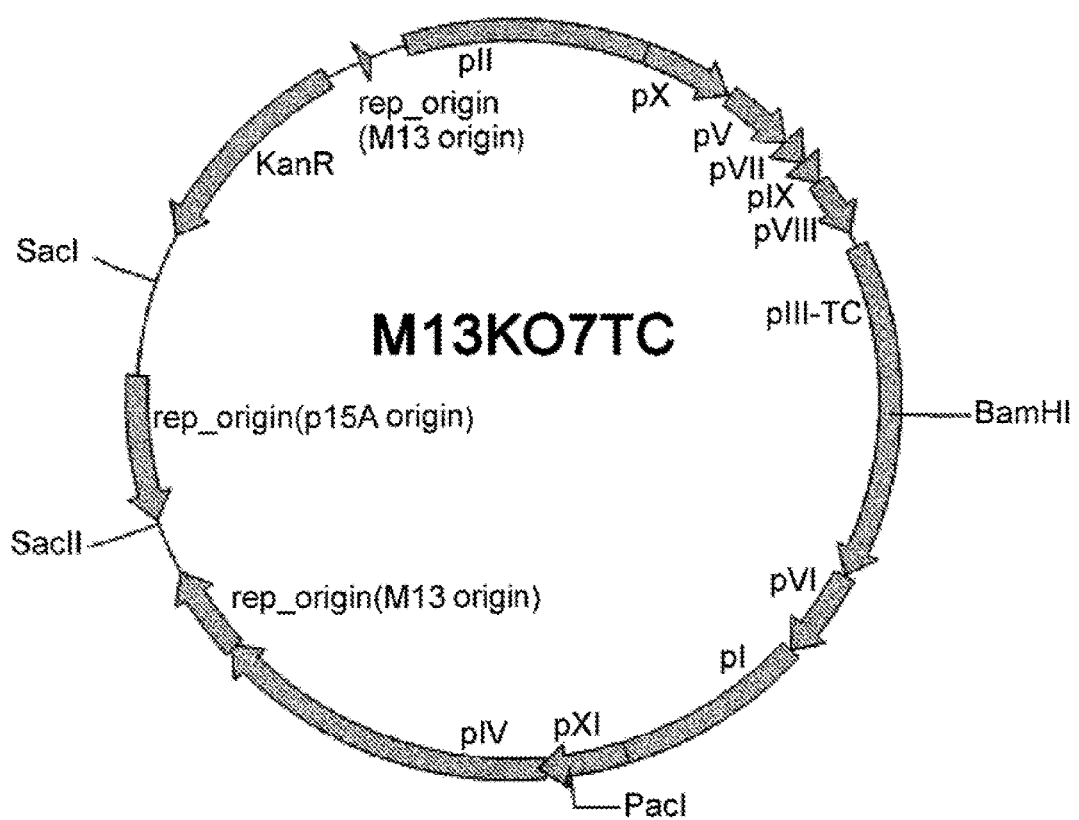
FIG. 1 is a schematic diagram of the genome of a helper phage M13KO7TC. An L chain expression unit was inserted to the SacI site shown in the diagram.

Hereinafter, preferred embodiments of the present invention will be described.

In one aspect, the present invention relates to a method for preparing a bacteriophage displaying an antigen-binding molecule, the method comprising the step of contacting a helper phage capable of expressing a first polypeptide with a bacterium capable of expressing a second polypeptide.

The first polypeptide and the second polypeptide according to the present invention associate with each other to form one antigen-binding molecule. It is desirable that the helper phage should infect the bacterium as a result of contacting the helper phage with the bacterium.

The helper phage is one kind of bacteriophage (also simply referred to as a phage) and refers to a bacteriophage having the function of helping other bacteriophages replicate. When wild-type bacteriophages infect host cells so that their genomes exist within the host cells, all proteins necessary for bacteriophage replication can usually be produced therefrom. Therefore, phage particles (virions) of the bacteriophages are constructed within the host cells. The genomes are further packaged in the phage particles so that bacteriophages are reconstructed and eventually released from the cells. However, in the case of an incomplete phage DNA that is derived from a bacteriophage genome and fails to produce all proteins necessary for bacteriophage replication due to the deletion, inactivation, or the like of a portion of the genome, such a DNA cannot reconstruct a bacteriophage in itself if present within host cells. When such host cells are infected with the helper phage, all proteins necessary for bacteriophage replication become able to be produced together with proteins derived from the genome of the helper phage. Therefore, phage particles can be constructed in the host cells to reconstruct bacteriophages. In this respect, a feature of the helper phage is that the genome of the helper phage has a defect in the replication origin of the genome or a packaging signal and is therefore less likely to be packaged in a phage particle than the genome of a wild-type bacteriophage (Methods Enzymol (1987) 153, 3-11). Therefore, even the incomplete phage DNA as mentioned above can be preferentially packaged in a phage particle rather than the genome of the helper phage as long as the incomplete phage DNA has usual packaging ability (e.g., phagemid vector). As a result, even the phage DNA that cannot reconstruct a bacteriophage in itself becomes able to reconstruct a bacteriophage in a form containing it in the inside.

The helper phages usually used belong to filamentous phages that infect gram-negative bacteria. Among them, Ff phage (f1, fd, M13, etc.), which infects E. coli having F factor, is widely used. The genome of the Ff phage is composed of circular single-stranded DNA and known to encode 11 proteins. These proteins are classified into phage particle structural proteins (g3p (also called gene 3 protein or pIII; the same holds true for the description below), g6p, g7p, g8p, and g9p), proteins involved in phage DNA replication (g2p, g5p, and g10p), and proteins involved in phage particle construction and secretion (g1p, g4p, and g11p), all of which are reportedly necessary for phage growth.

In one embodiment, the genome of the helper phage according to the present invention may encode unmutated 11 proteins, as in the wild-type genome, or may carry some mutation in these proteins. Such a mutation is usually introduced for the purpose of enhancing display efficiency in the preparation of an antigen-binding molecule display library mentioned later or for the purpose of enhancing selection efficiency in the selection (picking) of a desired antigen-binding molecule from the antigen-binding molecule display library. Examples of such a mutation include the partial or complete deletion of a g3p-encoding gene (gene 3 or III), the introduction of an amber mutation to gene 3, the introduction of a rare codon to gene 3, the introduction of a mutation to the ribosomal binding site of gene 3, the introduction of an amber mutation to a g9p-encoding gene (gene 9 or IX), and the introduction of a protease (e.g., trypsin) cleavage site to g3p.

In one embodiment, examples of the helper phage used in the present invention can include M13KO7, R408, VCSM13, KM13 (Res Microbiol (2001) 152, 187-191), M13MDD3.2 (FEMS Microbiol Lett (1995) 125, 317-321), R408d3 (Gene (1997) 198, 99-103), VCSM13d3 (Gene (1997) 198, 99-103), Hyperphage (Nat Biotechnol (2001) 19, 75-78), CT helper phage (Nucleic Acids Res (2003) 31, e59), Ex-phage (Nucleic Acids Res (2002) 30, e18), Phaberge (J Immunol Methods (2003) 274, 233-244), XP5 (J Immunol Methods (2012) 376, 46-54), and DeltaPhage (Nucleic Acids Res (2012) 40, e120). In general M13-series helper phages are preferred. Particularly preferred examples thereof can include M13KO7.

In one embodiment, the bacterium according to the present invention is not particularly limited as long as the cell can be infected by the helper phage. The bacterium according to the present invention is usually a gram-negative bacterium and is preferably E. coli (e.g., TG1, XL1-Blue, XL1-Blue MRF', and ER2738). The Ff phage (including M13-series helper phages) can infect any E. coli having F factor.

In one embodiment, the helper phage or the bacterium capable of expressing a first polypeptide or a second polypeptide according to the present invention means a helper phage or a bacterium having the ability to express the polypeptide under certain conditions. The helper phage, for example, needs only to have the ability to express the polypeptide when infecting the bacterium, and is not necessarily required to express the polypeptide when existing alone. Also, the bacterium may always express the polypeptide or may not express the polypeptide under usual growth conditions in the absence of a certain expression-inducing substance as long as the bacterium has the ability to express the polypeptide under conditions in the presence of the expression-inducing substance.

The helper phage capable of expressing a first polypeptide infects the bacterium capable of expressing a second polypeptide. As a result, the first polypeptide and the second polypeptide contained therein are expressed in the bacterium so that the first polypeptide and the second polypeptide associate with each other to form an antigen-binding molecule. At the same time, the antigen-binding molecule is incorporated in a phage particle reconstructed from the helper phage. Finally, a bacteriophage displaying the antigen-binding molecule is produced. Preferably, a polynucleotide encoding the second polypeptide derived from the bacterium is packaged in the reconstructed phage particle to transduce gene information on the second polypeptide to the newly formed bacteriophage. For this purpose, the polynucleotide encoding the second polypeptide preferably has the property of being packaged more efficiently, through insertion in a phagemid vector or the like, in the phage particle than the genome of the helper phage, though the polynucleotide according to the present invention is not limited thereto.

In one embodiment, for the helper phage according to the present invention, it is preferred that a polynucleotide encoding the first polypeptide should be inserted in the genome thereof.

The position at which the polynucleotide encoding the first polypeptide is inserted in the genome of the helper phage is not particularly limited. Preferably, the polynucleotide encoding the first polypeptide is inserted in a noncoding region, which does not encode phage proteins, in the genome without influencing the original functions of the helper phage. When the helper phage is M13KO7, specific examples of such a preferred position can include a SacI site positioned between a kanamycin resistance gene and p15A ori, and a SacII site positioned between p15A ori and M13 ori. Alternatively, when the first polypeptide is fused with a phage coat protein as mentioned later, the polynucleotide encoding the first polypeptide may be inserted at a position that allows this polynucleotide to be linked in frame with a polynucleotide encoding the phage coat protein in the genome.

In one embodiment, preferably, the polynucleotide encoding the first polypeptide according to the present invention is functionally linked to a promoter. The promoter refers to a polynucleotide sequence that can bind to RNA polymerase in a cell to start the transcription of the downstream (3' direction) sequence. In the present specification, the phrase "functionally linked to a promoter" may mean that the promoter is located at a position appropriate for a certain sequence so as to be capable of controlling the transcription of the sequence. The position of the promoter may be a position physically distant from the sequence. The promoter used in the present invention may be a constitutive promoter or may be an inducible promoter. A wide range of promoters can be used. Examples of the promoter suitable for prokaryotic cells can include: β-lactamase (bla) promoter, lactose (lac) promoter, tryptophan (trp) promoter, hybrid promoters such as tac promoter; tetracycline (tet) promoter, arabinose promoter, λ phage promoter, T7 phage promoter, and T5 phage promoter.

In one embodiment, the polynucleotide encoding the first polypeptide according to the present invention is preferably linked to a ribosomal binding site (RBS) such as a Shine-Dalgarno (SD) sequence. The ribosomal binding site located at an appropriate position promotes the translation of a polynucleotide positioned downstream thereof. The ribosomal binding site can be located between the promoter and the polynucleotide sequence placed under the control of the promoter.

In one embodiment, the first polypeptide according to the present invention is preferably linked to a signal sequence. The signal sequence refers to a peptide chain that is involved in the localization of a protein after intracellular expression of the protein. A sequence encoding the signal sequence can be located adjacent to a sequence encoding the protein. The signal sequence used in the present invention preferably localizes the protein to the periplasmic space of the host bacterium. Examples of such a signal sequence can include pelB signal sequence, gene III signal sequence, OmpA signal sequence, phoA signal sequence, malE signal sequence, dsbA signal sequence, E. coli heat-stable enterotoxin signal sequence, and beta lactamase signal sequence.

In one embodiment, the first polypeptide according to the present invention may be fused with a phage coat protein. The fusion of the first polypeptide with the phage coat protein can be carried out by linking the polynucleotide encoding the first polypeptide in frame with a polynucleotide encoding the phage coat protein. The phage coat protein may be a structural protein such as g3p, g6p, g7p, g8p, or g9p. In the present invention, the coat protein to be fused with the first polypeptide is preferably g3p or g8p, more preferably g3p.

The fusion with the coat protein is carried out for the purpose of displaying the first polypeptide on the surface of a phage particle. Therefore, the first polypeptide is preferably fused at the N terminus or C terminus of the coat protein. The coat protein may have a full length or may lack a portion such as the N terminus or C terminus. Also, the fusion may be carried out directly or may be carried out via an arbitrary linker peptide. In this context, the linker peptide can contain a tag sequence such as 6×His tag, Myc tag, or FLAG tag. Alternatively, the linker peptide may contain a protease recognition sequence for a protease such as trypsin or chymotrypsin. The tag sequence is useful for the detection, etc., of the fusion protein. The protease recognition sequence is useful because the antigen-binding molecule formed by the association of the first polypeptide with the second polypeptide can be separated and recovered from the phage coat protein by the digestion of the fusion protein with the protease.

In one embodiment, the number or type of the first polypeptide that can be expressed by the helper phage in the present invention is not particularly limited and can be usually only one type. In some cases, the helper phage may be capable of expressing two or more types of first polypeptides differing in amino acid sequence. The helper phage of the present invention is usually capable of expressing only one (first polypeptide) of the polypeptides constituting the antigen-binding molecule. In some cases, the helper phage of the present invention may be capable of expressing the first polypeptide with the other polypeptide (second polypeptide).

In one embodiment, the bacterium according to the present invention preferably comprises a polynucleotide encoding the second polypeptide. In this context the bacterium comprising a polynucleotide desirably means the bacterium transformed with the polynucleotide. Preferably, the polynucleotide is functionally linked to a promoter. The promoter may be a constitutive promoter or may be an inducible promoter. A wide range of promoters can be used. Examples of the promoter suitable for prokaryotic cells can include: β-lactamase (bla) promoter, lactose (lac) promoter, tryptophan (trp) promoter, hybrid promoters such as tac promoter; tetracycline (tet) promoter, arabinose promoter, λ phage promoter, T7 phage promoter, and T5 phage promoter. The transcription of the polynucleotide encoding the first polypeptide and the polynucleotide encoding the second polypeptide may be controlled in different manners by using different types of promoters as the promoter to be linked to the polynucleotide encoding the first polypeptide and the promoter to be linked to the polynucleotide encoding the second polypeptide in such a way that, for example, the expression of one of the polynucleotides is promoted while the expression of the other polynucleotide is suppressed.

In one embodiment, the polynucleotide encoding the second polypeptide according to the present invention is preferably linked to a ribosomal binding site (RBS) such as a Shine-Dalgarno (SD) sequence. The ribosomal binding site located at an appropriate position promotes the translation of a polynucleotide positioned downstream thereof. The ribosomal binding site can be located between the promoter and the polynucleotide sequence placed under the control of the promoter.

In one embodiment, the second polypeptide according to the present invention is preferably linked to a signal sequence. A sequence encoding the signal sequence can be located adjacent to a sequence encoding the protein. The signal sequence used in the present invention preferably localizes the protein to the periplasmic space of the host bacterium. Examples of such a signal sequence can include pelB signal sequence, gene III signal sequence, OmpA signal sequence, phoA signal sequence, malE signal sequence, dsbA signal sequence, E. coli heat-stable enterotoxin signal sequence, and beta lactamase signal sequence.

In one embodiment, the polynucleotide encoding the second polypeptide according to the present invention is preferably inserted in a phagemid vector. The phagemid vector is a plasmid vector prepared so as to contain a portion of a phage genome, and contains a replication origin (e.g., ColE1) for bacteria and a replication origin derived from the genome of a bacteriophage (e.g., M13, f1, and fd). The phagemid vector has the property of being amplified in the host bacterium, as with plasmid vectors, and also has the property of being packaged in the phage particle of a bacteriophage. Accordingly, when a bacterium transformed with the phagemid vector is infected with the helper phage, the phagemid vector can be preferentially packaged in a reconstructed phage particle rather than the original genome of the helper phage. Examples of the phagemid vector can include pHEN1, pComb3, pCANTAB5E, and pCES1.

In one embodiment, the second polypeptide according to the present invention may be fused with a phage coat protein. The fusion of the second polypeptide with the phage coat protein can be carried out by linking the polynucleotide encoding the second polypeptide in frame with a polynucleotide encoding the phage coat protein. The phage coat protein may be a structural protein such as g3p, g6p, g7p, g8p, or g9p. In the present invention, the coat protein to be fused with the second polypeptide is preferably g3p or g8p, more preferably g3p.

The fusion with the coat protein is carried out for the purpose of displaying the second polypeptide on the surface of a phage particle. Therefore, the second polypeptide is preferably fused at the N terminus or C terminus of the coat protein. The coat protein may have a full length or may lack a portion such as the N terminus or C terminus. Also, the fusion may be carried out directly or may be carried out via an arbitrary linker peptide. In this context, the linker peptide can contain a tag sequence such as 6×His tag or Myc tag. Alternatively, the linker peptide may contain a protease recognition sequence for a protease such as trypsin or chymotrypsin. The tag sequence is useful for the detection, etc., of the fusion protein. The protease recognition sequence is useful because the antigen-binding molecule formed by the association of the first polypeptide with the second polypeptide can be separated and recovered from the phage coat protein by the digestion of the fusion protein with the protease.

For displaying the antigen-binding molecule formed from the first polypeptide and the second polypeptide on the bacteriophage, it is preferred that at least one of the first polypeptide and the second polypeptide should be fused with a phage coat protein. When both of the first polypeptide and the second polypeptide are fused with phage coat proteins, the coat proteins are preferably selected from the same types of coat proteins (e.g., g3p, g6p, g7p, g8p, and g9p).

In one embodiment, as for the insertion position of the phage coat protein, a gene in which the polynucleotide encoding the first polypeptide is linked to the end (which corresponds to the N terminus or C terminus) of a gene encoding the phage coat protein such as g3p or g8p may be inserted to the helper phage, while the polynucleotide encoding the second polypeptide may be inserted to the phagemid vector without being linked to a gene encoding the phage coat protein; or the polynucleotide encoding the first polypeptide may be inserted to the helper phage without being linked to a gene encoding the phage coat protein, while a gene in which the polynucleotide encoding the second polypeptide is linked to the end (which corresponds to the N terminus or C terminus) of a gene encoding the phage coat protein such as g3p or g8p may be inserted to the phagemid vector.

In the present invention, the phrase "displaying X on Y" means that X is bound with the surface of Y with the original functions of X maintained. For example, the phrase "displaying an antigen-binding molecule on a bacteriophage" may mean that the antigen-binding molecule is bound with the surface of the bacteriophage particle while its ability to bind to the antigen is maintained. This binding may be carried out through a covalent bond or may be carried out through a noncovalent bond. When both of X and Y are polypeptides, X can be preferably bound with Y by preparing a fusion protein of X and Y. In the present invention, at least one of the first polypeptide and the second polypeptide is preferably fused with a phage coat protein. Alternatively, a method for displaying an antigen-binding molecule on a bacteriophage via a disulfide bond is also known (WO01/005950). The display may be carried out by use of such a method.

In one embodiment, the number or type of the second polypeptide that can be expressed by the bacterium in the present invention is not particularly limited. As mentioned later, the present invention relates to an antigen-binding molecule display library comprising a large number of antigen-binding molecules having common first polypeptides and different second polypeptides. Thus, a plurality of bacteria capable of expressing different types of second polypeptides are necessary for preparing such an antigen-binding molecule display library. Specifically, the individual bacteria used in the present invention are preferably a population of bacteria capable of expressing second polypeptides differing in amino acid sequence from each other and capable of expressing a plurality of diverse second polypeptides when viewed as a whole. Also, the bacterium of the present invention is usually capable of expressing only one (second polypeptide) of the polypeptides constituting the antigen-binding molecule. In some cases, the bacterium of the present invention may be capable of expressing the second polypeptide with the other polypeptide (first polypeptide).

In one embodiment, the antigen-binding molecule according to the present invention is not particularly limited as long as the molecule is formed in a form comprising two polypeptides (first polypeptide and second polypeptide) and has the ability to specifically bind to a certain antigen. The first polypeptide and the second polypeptide are preferably polypeptides differing in amino acid sequence from each other. Preferred examples of the antigen-binding molecule can include antibodies, Fab, F(ab')$_2$, diabody (Nature Nanotechnology (2007) 2, pp. 751-760), antibody variable regions, antibody fragments containing antibody variable regions, receptor proteins, Fc proteins, antibody fragments containing Fc proteins, Fc fusion proteins, and functional fragments thereof (fragments having antigen-binding sites and having functions thereof) and functional equivalents thereof (equivalents having antigen-binding sites and functions thereof, such as sugar chain-modified forms thereof).

The antigen-binding molecule according to the present specification may be derived from any animal species (e.g., humans; or non-human animals such as mice, rats, hamsters, rabbits, monkeys, cynomolgus monkeys, rhesus monkeys, hamadryas baboon, chimpanzees, goats, sheep, dogs, cattle, and camels) or any bird.

When the antigen-binding molecule according to the present specification is an antibody (immunoglobulin) or a molecule derived from therefrom, the antibody or the molecule may be of any isotype (e.g., IgG, IgM, IgA, IgD, and IgE) and subclass (e.g., human IgG1, IgG2, IgG3, IgG4, IgA1, and IgA2, and mouse IgG1, IgG2a, IgG2b, and IgG3) or may be derived therefrom. The H chains of the antibody or the molecule derived therefrom may be, for example, any of γ chain, μ chain, α chain, δ chain, and ε chain or may be derived therefrom. Also, the L chains of the antibody or the molecule derived therefrom may be, for example, any of κ chain and λ chain or may be derived therefrom. The antibody or the molecule derived therefrom may be an engineered antibody, for example, a chimeric antibody, a humanized antibody, or an affinity-matured antibody, or a molecule derived therefrom.

In one embodiment, when the antigen-binding molecule according to the present invention is an antibody, preferably, the antibody comprises first polypeptides which are two identical polypeptides comprising (or consisting of) L chains, and second polypeptides which are two identical polypeptides comprising (or consisting of) H chains; or comprises first polypeptides which are two identical polypeptides comprising (or consisting of) H chains, and second polypeptides which are two identical polypeptides comprising (or consisting of) L chains. Specifically, the first polypeptide and the second polypeptide are each preferably selected from the group consisting of the two polypeptides comprising (or consisting of) L chains and the two polypeptides comprising (or consisting of) H chains, and differ from each other. A phage library using such antibodies (IgG phage display) is generally known to those skilled in the art, as described in, for example, FEBS J. 2010 May; 277 (10): 2291-303 and WO2011062859. Those skilled in the art should understand that the antibody can be used as the antigen-binding molecule of the present invention.

The F(ab')$_2$ is known as an antigen-binding molecule that can be prepared by digestion of an IgG antibody with pepsin. The F(ab')$_2$ is a divalent molecule having two antigen-binding sites and having a structure in which two Fab' molecules are linked through two disulfide bonds without the Fc regions of the antibody (two Fab' molecules+hinge regions).

In one embodiment, when the antigen-binding molecule according to the present invention is F(ab')$_2$, preferably, the F(ab')$_2$ comprises first polypeptides which are two identical polypeptides comprising L chain variable regions, and second polypeptides which are two identical polypeptides comprising H chain variable regions; or comprises first polypeptides which are two identical polypeptides comprising H chain variable regions, and second polypeptides which are two identical polypeptides comprising L chain variable regions. Specifically, the first polypeptide and the second polypeptide are each preferably selected from the group consisting of the two polypeptides comprising L chain variable regions and the two polypeptides comprising H chain variable regions, and differ from each other. A phage library using such F(ab')$_2$ molecules is generally known to those skilled in the art, as described in, for example, J Immunol Methods. 2004 January; 284 (1-2): 119-32. Those skilled in the art should understand that the F(ab')$_2$ can be used as the antigen-binding molecule of the present invention. In the literature, "Fab'-zip-" was displayed on a phage by the insertion of a dimerization domain, consisting of an IgG1 hinge region and a homodimerizing leucine zipper, between Fab and M13 bacteriophage g3p (gene 3 protein) so that F(ab')$_2$ was formed on the phage ("Fab'-zip-phage") to construct a phage library displaying divalent Fab with high avidity similar to that of an IgG antibody.

The diabody is a dimer prepared by the binding of two fragments each containing a variable region and a variable region linked via a linker or the like (e.g., single-chain antibodies (scFvs)) (hereinafter, referred to as diabody-constituting fragments). The diabody usually comprises two H chain variable regions and two L chain variable regions and has two antigen-binding sites (P. Holliger et al., Proc. Natl. Acad. Sci. USA, 90, 6444-6448 (1993); EP404097; WO93/11161; Johnson et al., Method in Enzymology, 203, 88-98, (1991); Holliger et al., Protein Engineering, 9, 299-305, (1996); Perisic et al., Structure, 2, 1217-1226, (1994); John et al., Protein Engineering, 12 (7), 597-604, (1999); Holliger et al., Proc. Natl. Acad. Sci. USA., 90, 6444-6448, (1993); and Atwell et al., Mol. Immunol. 33, 1301-1312, (1996)).

Each diabody-constituting fragment is preferably an H chain variable region (or its fragment) and an L chain variable region (or its fragment) linked. In the diabody-constituting fragment, the linker that links the variable region and the variable region is not particularly limited. A linker short enough not to cause a noncovalent bond between the variable regions in the same fragment is preferably used. The length of such a linker can be appropriately determined by those skilled in the art and is usually 2 to 14 amino acids, preferably 3 to 9 amino acids, particularly preferably 4 to 6 amino acids. In this case, the H chain variable region (or its fragment) and the L chain variable region (or its fragment) encoded on the same fragment do not cause a noncovalent bond therebetween on the same chain because of the short linker between the H chain variable region (or its fragment) and the L chain variable region (or its fragment). Thus, this diabody-constituting fragment can form a dimer with another fragment without forming a single-chain V region fragment. For the formation of the dimer, the binding between the diabody-constituting fragments may be a noncovalent bond (e.g., hydrogen bond, electrostatic interaction, or van der Waals force) or a covalent bond (e.g., disulfide bond), or both of a covalent bond and a noncovalent bond.

In one embodiment, when the antigen-binding molecule according to the present invention is diabody, preferably, the first polypeptide is an H chain variable region (or its fragment) and an L chain variable region (or its fragment) linked via a linker, and the second polypeptide is an L chain variable region (or its fragment) and an H chain variable region (or its fragment) linked via a linker; or the first polypeptide is an L chain variable region (or its fragment) and an H chain variable region (or its fragment) linked via a linker, and the second polypeptide is an H chain variable region (or its fragment) and an L chain variable region (or its fragment) linked via a linker. Specifically, the first polypeptide and the second polypeptide are each preferably selected from the group consisting of the H chain variable region (or its fragment) and the L chain variable region (or its fragment) linked via a linker, and the L chain variable region (or its fragment) and the H chain variable region (or its fragment) linked via a linker, and differ from each other. A phage library using such diabodies is generally known to those skilled in the art, as described in, for example, Nat Biotechnol. 1996 September; 14 (9): 1149-54; and US 20070036789. Those skilled in the art should understand that the diabody can be used as the antigen-binding molecule of the present invention.

In one embodiment, a receptor protein that is formed in a form comprising two polypeptides and specifically binds to a certain ligand can also be included in the antigen-binding molecule of the present invention. In this case, the receptor protein is preferably a heteromeric receptor protein constituted by two polypeptides differing in amino acid sequence from each other. The receptor protein may be, for example, an extracellular region of the receptor protein, a ligand-binding region of the receptor protein, or a fusion protein thereof with an antibody Fc region. When the antigen-binding molecule is a receptor protein, the antigen refers to a ligand for the receptor protein. Examples of the heteromeric receptor can include IL-2 receptor, IL-3 receptor, IL-4 receptor, IL-5 receptor, IL-6 receptor, IL-7 receptor, IL-9 receptor, IL-10 receptor, IL-11 receptor, IL-12 receptor, IL-13 receptor, IL-15 receptor, IL-17 receptor, IL-23 receptor, IL-31 receptor, GM-CSF receptor, IFN-α receptor, IFN-β receptor, IFN-γ receptor, CNTF receptor, LIF receptor, OSM receptor, and CT-1 receptor.

In one embodiment, an Fc protein that is formed in a form comprising two polypeptides and specifically binds to a certain Fc receptor can also be included in the antigen-binding molecule of the present invention. The Fc protein refers to a region composed of hinges or a portion thereof and CH2 and CH3 domains of an antibody molecule and generally referred to an amino acid sequence from EU numbering position 226 to the C terminus or from EU numbering position 230 to the C terminus. Alternatively, the Fc protein may be composed of CH2 and CH3 domains, or only CH3 domains. In this case, the Fc protein is preferably an altered Fc protein having some amino acid mutation added to a naturally occurring Fc protein and is preferably constituted by two polypeptides differing in amino acid sequence from each other. Examples of such a heteromeric Fc protein can include Fc proteins described in, for example, WO98/50431, WO2006/106905, WO2007/114325, WO2011/078332, and WO2013/002362. Particularly, WO98/50431 states that the amino acid sequence of one of the polypeptides constituting the heteromeric Fc protein is fixed, and the amino acid sequence of the other polypeptide is altered, whereby a combination of two polypeptides most compatible with each other can be selected (picked) from among diverse sequences. When the antigen-binding molecule is an Fc protein, the antigen refers to any of various Fc receptors (e.g., FcγRI, FcγRIIa, FcγRIIb, FcγRIII, and FcRn). For example, an amino acid in the antibody Fc region can be altered to thereby enhance binding to FcRn (neonatal Fc receptor) under neutral pH conditions (WO2011/122011) or enhance binding to an Fcγ receptor under neutral pH conditions (WO2013/047752). As a result, the antigen can reportedly be removed rapidly from blood.

In another embodiment, an Fc fusion protein in which the Fc protein is fused with a protein (e.g., a cytokine or a receptor extracellular domain) or a peptide can also be included in the antigen-binding molecule of the present invention. The Fc fusion protein may contain an antibody hinge region and/or a linker. Soluble Fc fusion proteins are widely used in in vitro and in vivo experiments and can have many advantages over non-fusion proteins (Meg L et al., Methods in Molecular Biology 378: 33-52, 2007). In addition, the soluble Fc fusion proteins can eliminate many immunological problems in the production of human antibody preparations, while maintaining antigen specificity. Typical examples of the soluble Fc fusion human antibody preparations include Etanercept (Amgen Inc.), a therapeutic drug for autoimmune disease, which has been produced by fusing soluble TNF receptor 2 with Fc of human IgG1. Those skilled in the art understand that the Fc fusion protein can be appropriately produced by use of a method generally known to those skilled in the art, as described in, for example, WO2009/136568, WO2007/048122, and WO2011/115323, and used in a phage library.

In one embodiment, when the antigen-binding molecule according to the present invention has antibody variable regions, preferably, the first polypeptide is a polypeptide comprising (or consisting of) an L chain variable region, and the second polypeptide is a polypeptide comprising (or consisting of) an H chain variable region; or the first polypeptide is a polypeptide comprising (or consisting of) an H chain variable region, and the second polypeptide is a polypeptide comprising (or consisting of) an L chain variable region. Specifically, the first polypeptide and the second polypeptide are preferably each selected from the group consisting of the polypeptide comprising (or consisting of) an L chain variable region and the polypeptide comprising (or consisting of) an H chain variable region, and differ from each other.

In one aspect, an object of the present invention is to provide a combination of a helper phage suitable for preparing a plurality of antigen-binding molecules comprising common first polypeptides, and a bacterium infectible by the helper phage. A polypeptide having an arbitrary amino acid sequence can be selected as such a first polypeptide as long as the first polypeptide is one of the polypeptides constituting each antigen-binding molecule. For example, when the antigen-binding molecule has antibody variable regions and the first polypeptide is a polypeptide comprising an L chain variable region or a polypeptide comprising an H chain variable region, the L chain variable region or the H chain variable region can be selected from among L chain variable regions or H chain variable regions having arbitrary amino acid sequences. In short, even if an L chain variable region or an H chain variable region having any amino acid sequence is selected, a plurality of antigen-binding molecules (here, antibody variable regions) comprising the selected one as common first polypeptides can be prepared. The L chain variable region or the H chain variable region may be selected from among L chain variable regions or H chain variable regions contained in antibodies binding to particular antigens, or may be selected from among L chain variable regions or H chain variable regions contained in naive antibodies before immunization with the particular antigens.

The antibody binding to a particular antigen can be prepared by a hybridoma method (Nature (1975) 256, 495) or a phage antibody library method (Nature (1991) 352, 624-628, J Mol Biol (1991) 222, 581-597) generally known to those skilled in the art. The amino acid sequence of the L chain variable region or the H chain variable region of the antibody prepared by the hybridoma method can be identified by amplifying a gene encoding the L chain or the H chain contained in a hybridoma producing the antibody by PCR using primers specific for the antibody gene, and analyzing the sequence (J Mol Biol (1991) 222, 581-597; and Mol Immunol (1992) 29, 193-203). Also, the amino acid sequence of the L chain variable region or the H chain variable region of the antibody prepared by the phage antibody library method can be identified by isolating a vector contained in a phage displaying the antibody, and analyzing the sequence of the gene encoding the L chain or the H chain inserted therein.

The amino acid sequence of the L chain variable region or the H chain variable region contained in the naive antibody before immunization with the particular antigen can be identified at a large scale by: preparing, for example, peripheral blood mononuclear cells, bone marrow cells, or spleen cells producing such antibodies from humans or other animals, etc., amplifying genes encoding L chains or H chains contained in these cells by PCR using primers specific for the antibody gene, and analyzing the sequences. Therefore, the L chain variable region or the H chain variable region can be arbitrarily selected, for use, from among the L chain variable regions or the H chain variable regions thus identified (J Mol Biol (1991) 222, 581-597; and Mol Immunol (1992) 29, 193-203).

In one embodiment, when the first polypeptide or the second polypeptide according to the present invention is a polypeptide comprising an L chain variable region or a polypeptide comprising an H chain variable region, the polypeptide may further comprise an L chain constant region or an H chain constant region. If the first polypeptide comprises no constant region, it is preferred that the second polypeptide should comprise no constant region. If the first polypeptide comprises a constant region, it is preferred that the second polypeptide should also comprise a constant region. The H chain constant region is particularly preferably an H chain constant region CH1 domain. In this context, the H chain constant region CH1 domain refers to a region from the beginning of the H chain constant region to immediately before the hinge region and generally refers to an amino acid sequence from EU numbering positions 118 to 225. Usually, these constant regions are contained in a form linked immediately after the variable regions. The L chain constant region may be a constant region derived from any of κ chain and λ chain. The H chain constant region may be a constant region derived from any of γ chain, μ chain, α chain, δ chain, and ε chain. Furthermore, these constant regions may have a full length or may lack a portion. Also, these constant regions may be altered by the substitution, deletion, insertion, etc., of a portion of their amino acids. When the first polypeptide and the second polypeptide comprise constant regions, a preferred example of the antigen-binding molecule is Fab.

In an alternative aspect, the present invention relates to a method for preparing an antigen-binding molecule display library comprising common first polypeptides, wherein the method comprises:

(a) carrying out the method for preparing a bacteriophage displaying an antigen-binding molecule according to the present invention a plurality of times, wherein a plurality of bacteria used in the step are a bacterium population capable of expressing a plurality of second polypeptides differing in amino acid sequence, and helper phages used in the step are helper phages capable of expressing first polypeptides having identical amino acid sequences; and (b) recovering a plurality of bacteriophages displaying antigen-binding molecules prepared in (a).

The plurality of bacteria are preferably a bacterium population in which the individual bacteria are bacteria capable of expressing second polypeptides differing in amino acid sequence from each other and are capable of expressing a plurality of diverse second polypeptides when viewed as a whole. Such a plurality of bacteria can be infected with the helper phages, respectively, capable of expressing first polypeptides having identical amino acid sequences to prepare a plurality of bacteriophages displaying antigen-binding molecules. All of these antigen-binding molecules comprise the common first polypeptides and the second polypeptides differing from each other. A plurality of bacteriophages displaying the antigen-binding molecules thus prepared can be recovered and mixed to prepare an antigen-binding molecule display library comprising the common first polypeptides.

In the present specification, the library means an assembly of a plurality of components having diverse repertoires. In the present invention, the library mainly refers to a bacteriophage library (phage library) constituted by an assembly of a plurality of bacteriophages. The antigen-binding molecule display library means a library having, as components, bacteriophages displaying antigen-binding molecules on their surface. The antigen-binding molecules contained therein preferably have diverse repertoires. A larger number of components in the library (larger size of the library) is more preferred. The library size is preferably, for example, $10^6$ or more, $10^7$ or more, $10^8$ or more, $10^9$ or more, $10^{10}$ or more, $10^{11}$ or more, $10^{12}$ or more, $10^{13}$ or more, or $10^{14}$ or more. In the method for preparing an antigen-binding molecule display library according to the present invention, the number of a plurality of bacteria capable of expressing second polypeptides, used in the step, is equal to the number of components in the library. Therefore, the bacterium population used in the step preferably contains, for example, $10^6$ or more, $10^7$ or more, $10^8$ or more, $10^9$ or more, $10^{10}$ or more, $10^{11}$ or more, $10^{12}$ or more, $10^{13}$ or more, or $10^{14}$ or more bacteria.

In order to carry out the infection a plurality of times as described above, usually, a bacterium population capable of expressing a plurality of second polypeptides is cultured in a mixed state, while a plurality of helper phages capable of expressing identical first polypeptides can be allowed to collectively infect the bacterium population. Alternatively, each helper phage may be allowed to individually infect a small scale of a bacterium population containing one or more bacteria. Since the prepared bacteriophages are usually released into the culture supernatant of the bacteria, the bacteriophages may be recovered by merely separating the culture supernatant by the centrifugation or the like of the culture solution of the bacteria after the helper phage infection, or may be recovered by an additional step of isolating and purifying the bacteriophages, for example, by a method for precipitating the bacteriophages by the addition of polyethylene glycol (PEG) thereto (PEG precipitation method).

When the antigen-binding molecule has antibody variable regions and the second polypeptide is a polypeptide comprising an L chain variable region or a polypeptide comprising an H chain variable region, genes encoding a plurality of L chain variable regions or H chain variable regions differing in amino acid sequence from each other can be obtained, for example, by isolating a large number of naturally occurring antibody genes (e.g., antibody genes found in vivo). For example, antibody-producing cells such as peripheral blood mononuclear cells, bone marrow cells, or spleen cells are prepared from humans or other animals, etc. On the basis of RNAs obtained from these cells, reverse transcription-polymerase chain reaction (RT-PCR) can be carried out using primers specific for the L chain variable regions or the H chain variable regions to amplify genes encoding the L chain variable regions or the H chain variable regions. In this case, naive antibody-producing cells before immunization with a particular antigen are preferably used from the viewpoint of obtaining high diversity. In some cases, biased antibody-producing cells after immunization with the particular antigen may be used. Alternatively, the genes can also be obtained by synthesizing a large number of genes diversified, for example, by the artificial mutation of a gene encoding a certain L chain variable region or H chain variable region. Such genes may be prepared by artificially inducing a mutation using an approach, for example, Error prone PCR or may be prepared by the total synthesis of genes having sequences designed so as to have desired diversity.

In an alternative aspect, the present invention also encompasses an antigen-binding molecule display library prepared by the method for preparing an antigen-binding molecule display library according to the present invention.

In an alternative aspect, the present invention relates to a method for obtaining an antigen-binding molecule specifically binding to a predetermined antigen, wherein the method comprises:

(a) contacting the antigen with the antigen-binding molecule display library of the present invention; and (b) selecting an antigen-binding molecule binding to the antigen from the antigen-binding molecule display library.

In one embodiment, the antigen-binding molecule display library of the present invention comprises a plurality of diverse antigen-binding molecules differing in sequence from each other, and is therefore a population of antigen-binding molecules capable of binding to various types of antigens when viewed as a whole. Accordingly, the antigen-binding molecule display library of the present invention can be screened to select (pick) an antigen-binding molecule specifically binding to the desired antigen. Specifically, the antigen is contacted with the antigen-binding molecule display library of the present invention so that an antigen-binding molecule capable of specifically binding to the antigen in the library binds to the antigen to form a complex. Then, the antigen-binding molecule complexed with the antigen, among a plurality of antigen-binding molecules contained in the library, can be separated from antigen-unbound antigen-binding molecules by some method generally known to those skilled in the art to select (pick) only the antigen-binding molecule specifically binding to the antigen. The method for separating the antigen-binding molecule complexed with the antigen can involve, for example, contacting the antigen biotinylated in advance with the antigen-binding molecule display library, and then allowing the biotinylated antigen to bind to avidin or streptavidin immobilized on a carrier such as beads or a plate to recover only the antigen-binding molecule complexed with the antigen onto the beads or the plate. Then, the beads or the plate is washed so that antigen-unbound antigen-binding molecules can be removed from the antigen-binding molecule display library to separate the antigen-binding molecule complexed with the antigen from the antigen-unbound antigen-binding molecules.

The aforementioned operation of selecting an antigen-binding molecule specifically binding to the antigen may be repeated a plurality of times. Specifically, antigen-binding molecules having the weak ability to bind to the antigen and antigen-binding molecules having the strong ability to bind to the antigen seem to coexist in an antigen-binding molecule group separated by the first selecting operation. Therefore, the abundance of the antigen-binding molecules having the strong ability to bind to the antigen can be gradually enhanced by repeating the selecting operation. In one embodiment, bacteriophages displaying the antigen-binding molecules separated by the first selecting operation are allowed to temporarily infect host bacteria, followed by the culture of the bacteria for growth. Since polynucleotide encoding the second polypeptides are usually packaged in the bacteriophages prepared in the present invention, the polynucleotides encoding the second polypeptides are present in the bacteria infected with the bacteriophages. In short, the bacteria in this state are bacteria capable of expressing the second polypeptides. Therefore, the bacteria are infected with the same helper phages (i.e., the helper phages capable of expressing the same first polypeptides) as in the preparation of the initial antigen-binding molecule display library. As a result, bacteriophages displaying the same antigen-binding molecules as those separated by the first selection operation can be reproduced with the number thereof increased. The thus-obtained bacteriophages displaying the antigen-binding molecules can be used as starting materials again in the repeated selection operation to form an antigen-binding molecule population comprising a large number of only antigen-binding molecules having the strong ability to bind to the antigen.

The antigen-binding molecules contained in the antigen-binding molecule display library are present in a state displayed on the bacteriophages. Only the antigen-binding molecules may be obtained by some method. For example, when each antigen-binding molecule is fused with a phage coat protein via protease (e.g., trypsin) cleavage site introduced therebetween, the antigen-binding molecule can be separated from the bacteriophage through the reaction of the protease with the bacteriophage displaying the antigen-binding molecule to isolate only the antigen-binding molecule. When the polynucleotide encoding the second polypeptide is packaged in the phage particle of the bacteriophage prepared by the method of the present invention, sequence information on the antigen-binding molecule can be identified from this polynucleotide and the polynucleotide encoding the first polypeptide contained in the helper phage of the present invention. The antigen-binding molecule can be separately prepared by a genetic engineering approach.

In one embodiment, the antigen according to the present invention is not particularly limited as long as the antigen is a compound containing a structure that can serve as an antigenic determinant (epitope). The antigen may be a low-molecular compound or may be a high-molecular compound. General examples of the antigen can include polypeptides, polynucleotides, sugar chains, lipids, and molecules composed of combinations thereof. These antigens may be prepared by isolation from naturally occurring materials or may be prepared by artificial synthesis. When the antigen is, for example, a polypeptide, the polypeptide can be prepared by a genetic engineering approach. Specifically, a polynucleotide encoding the amino acid sequence of the polypeptide is prepared by an approach generally known to those skilled in the art, such as a gene cloning method or a nucleic acid synthesis method, and this polynucleotide can be inserted to an expression vector or the like known in the art, which is then transferred to appropriate host cells to prepare the polypeptide. The expressed polypeptide can be purified by a usual method such as ion chromatography or affinity chromatography.

In the present specification, the "antigen-binding molecule specifically binding to the antigen" means that the binding activity of the antigen-binding molecule against the particular antigen is, for example, preferably 2 or more times, 3 or more times, or 5 or more times, more preferably 10 or more times, 20 or more times, or 30 or more times, further preferably 50 or more times or 100 or more times higher than its binding activity against other antigens. The binding activity of the antigen-binding molecule against the antigen can be measured and compared by a method generally known to those skilled in the art, such as ELISA, FACS, or Biacore. The antigen defined above may be used interchangeably with an epitope. In short, the antigen-binding molecule specifically binding to the antigen means that the binding activity of the antigen-binding molecule against the particular epitope is, for example, preferably 2 or more times, 3 or more times, or 5 or more times, more preferably 10 or more times, 20 or more times, or 30 or more times, further preferably 50 or more times or 100 or more times higher than its binding activity against other epitopes.

In an alternative aspect, the present invention relates to a method for preparing a multispecific antigen-binding molecule comprising common first polypeptides, wherein the method comprises:

(a) carrying out the method for obtaining an antigen-binding molecule specifically binding to a predetermined antigen according to the present invention for a plurality of antigens; and (b) preparing a multispecific antigen-binding molecule using a plurality of first polypeptides having identical amino acid sequences and a plurality of second polypeptides having different amino acid sequences, contained in a plurality of antigen-binding molecules obtained in (a), wherein the first polypeptides associate with the plurality of second polypeptides, respectively, to form the plurality of antigen-binding molecules specifically binding to the plurality of antigens.

In an alternative embodiment, the aforementioned method of the present invention may be a method for preparing a multispecific antigen-binding molecule comprising common first polypeptides, wherein the method comprises:

(a) carrying out the method for obtaining an antigen-binding molecule specifically binding to a predetermined antigen according to the present invention for a plurality of antigens;

(b) for a plurality of first polypeptides having identical amino acid sequences and a plurality of second polypeptides having different amino acid sequences, contained in a plurality of antigen-binding molecules obtained in (a), separately preparing polynucleotides encoding the first polypeptides and polynucleotides encoding the plurality of second polypeptides;

(c) transferring each the polynucleotide prepared in (b) to a host cell; and (d) culturing the host cell of (c) to recover a multispecific antigen-binding molecule, wherein the first polypeptides associate with the plurality of second polypeptides, respectively, to form the plurality of antigen-binding molecules specifically binding to the plurality of antigens.

The antigen-binding molecule obtained by the method for obtaining an antigen-binding molecule specifically binding to a predetermined antigen according to the present invention absolutely comprises the first polypeptide. Therefore, all of the plurality of antigen-binding molecules obtained as a result of carrying out the method for a plurality of antigens comprise the common first polypeptides and the second polypeptides differing from each other. The first polypeptides and the plurality of second polypeptides thus obtained are combined such that the plurality of second polypeptides associate with the first polypeptides, respectively, to form the plurality of antigen-binding molecules. Thus, the plurality of antigen-binding molecules thus prepared are reconstructed so as to form one molecule in which the antigen-binding molecules are linked. In this way, the multispecific antigen-binding molecule comprising the common first polypeptides can be easily prepared. In this respect, the multispecific antigen-binding molecule may be prepared by use of a genetic engineering approach. Specifically, polynucleotides encoding the first polypeptides and polynucleotides encoding the plurality of second polypeptides are separately prepared. These polynucleotides are transferred to a host cell, and the host cell is cultured under conditions that permit expression of the polynucleotides. The plurality of second polypeptides expressed from the polynucleotides associate with the first polypeptides, respectively, to form the plurality of antigen-binding molecules. Thus, the plurality of antigen-binding molecules thus prepared are reconstructed so as to form one molecule in which the antigen-binding molecules are linked. In this way, the multispecific antigen-binding molecule comprising the common first polypeptides can be easily expressed. The multispecific antigen-binding molecule extracellularly expressed by the host cell may be recovered by recovering the culture supernatant by the centrifugation of the culture solution of the host cell or may be recovered by preparing the cell extract of the host cell. The step of isolating and purifying the multispecific antigen-binding molecule therefrom may be further added to the method (Nat Biotechnol. 1998 July; 16 (7): 677-81).

The polynucleotides encoding the first polypeptides and the polynucleotides encoding the plurality of second polypeptides are preferably inserted in some expression vector. Each polynucleotide may be individually inserted to the expression vector, or these polynucleotides may be collectively inserted to the same expression vector. Examples of the expression vector can include pET for *E. coli* and pcDNA3 for mammalian cells.

Examples of the host cell to which the polynucleotides encoding the first polypeptides and the polynucleotides encoding the plurality of second polypeptides are transferred can include *E. coli* cells JM109, DH5a, HB101, and XL1-Blue, and mammalian cells CHO, COS, and HEK293.

The transfer of the polynucleotides to the host cell can be carried out by use of an approach generally known to those skilled in the art, such as a calcium phosphate method, a DEAE dextran method, an electroporation method, a lipofection method, or a microinjection method.

The multispecific antigen-binding molecule recovered from the host cell may be isolated and purified by a method known in the art, for example, centrifugation, ammonium sulfate fractionation, salting out, dialysis, ultrafiltration, affinity chromatography, ion-exchange chromatography, or gel filtration chromatography.

In one embodiment, the multispecific antigen-binding molecule according to the present invention means a molecule containing, in one molecule, a plurality of antigen-binding molecules specifically binding to a plurality of antigens, respectively. The antigen-binding molecules can be linked to each other in some manner to form one molecule. This linking may be carried out through a covalent bond (e.g., peptide bond or disulfide bond) or may be carried out through a noncovalent bond. The antigen-binding molecules may be connected directly or may be connected via a linker molecule such as a linker peptide. When the antigen-binding molecules are antibody variable regions, examples of the multispecific antigen-binding molecule can include a molecule in which a plurality of H chain variable regions and L chain variable regions are connected either directly or through a peptide bond via a linker peptide, and a plurality of antibody variable regions are formed by the appropriate intramolecular association between the H chain variable regions and the L chain variable regions (e.g., diabody, triabody, and single-chain diabody). Another example thereof can include a molecule in which H chain variable regions and L chain variable regions are connected to H chain constant regions and L chain constant regions, respectively, through a peptide bond, while these H chain constant regions are connected through a disulfide bond or the like, and a plurality of antibody variable regions are formed by the appropriate intramolecular association between the H chain variable regions and the L chain variable regions (e.g., antibody (immunoglobulin) molecules such as IgG, IgM, IgA, IgD, and IgE). The respective antigen-binding molecules contained in the multispecific antigen-binding molecule may be antigen-binding molecules binding to their distinctive antigens or may be antigen-binding molecules binding to different antigenic determinants (epitopes) contained in the same antigen. In some cases, the respective antigen-binding molecules contained in the multispecific antigen-binding molecule may be antigen-binding molecules binding to identical epitopes in identical antigens. The number of the antigen-binding molecules contained in the multispecific antigen-binding molecule can be increased to 2, 3, 4, etc., to thereby prepare a bispecific antigen-binding molecule, a trispecific antigen-binding molecule, a tetraspecific antigen-binding molecule, etc., respectively. The multispecific antigen-binding molecule according to the present invention is preferably a bispecific antigen-binding molecule (e.g., bispecific antibody).

The multispecific antigen-binding molecule can be used for various purposes. It has already been known that the multispecific antigen-binding molecule can be used as an active ingredient for a pharmaceutical composition in the treatment of a disease for one of the purposes. For example, in the treatment of a cancer, a bispecific antigen-binding molecule comprising an antigen-binding molecule binding to a tumor antigen and an antigen-binding molecule binding to a molecule inducing cytotoxic activity is useful as a molecule that can induce cytotoxicity specific for the tumor cells. Examples of the tumor antigen include CD15, p185 (HER2), p97, OVCAR-3, L-D1, EGFR, CAMA1, CD19, MoV18, NCAM, FBP, AMOC-31, Id-1, CD22, CD7, CD38, CEA, and CD30. Examples of the molecule inducing cytotoxic activity include FcγRI, FcγRIII (CD16), and CD3. Also, in the treatment of an infectious disease, a bispecific antigen-binding molecule comprising an antigen-binding molecule binding to a virus and an antigen-binding molecule binding to a molecule inducing cytotoxic activity is useful as a molecule that can induce cytotoxicity specific for the virus-infected cells. Examples of the virus can include herpes simplex virus (HSV), influenza virus, and human immunodeficiency virus (HIV). In addition, a bispecific antigen-binding molecule comprising an antigen-binding molecule binding to fibrin and an antigen-binding molecule binding to a plasminogen activator is useful as a thrombolytic drug. Examples of the plasminogen activator can include tissue plasminogen activator (tPA) and urokinase plasminogen activator (uPA). Furthermore, an agonist molecule of a cytokine can be obtained from among bispecific antigen-binding molecules each comprising antigen-binding molecules binding to polypeptide chains constituting a heteromeric receptor for the cytokine, respectively (WO2004/060919). Examples of the cytokine having a heteromeric receptor can include IL-2, IL-3, IL-4, IL-5, IL-6, IL-7, IL-9, IL-10, IL-11, IL-12, IL-13, IL-15, IL-17, IL-23, IL-31, GM-CSF, IFN-α, IFN-β, IFN-γ, CNTF, LIF, OSM, and CT-1. Also, a functional molecule that can serve as an alternative to the effects of a cofactor enhancing enzymatic reaction can be obtained from among bispecific antigen-binding molecules each comprising an antigen-binding molecule binding to the enzyme and an antigen-binding molecule binding to a substrate of the enzyme (WO2005/035754). Examples of such an enzyme-substrate-cofactor combination can include blood coagulation factor IX (FIXa)-blood coagulation factor X (FX)-blood coagulation factor VIII (FVIII/FVIIIa) combination, protein Z-dependent protein inhibitor (ZPI)-blood coagulation factor X (FX/FXa)-protein Z (PZ) combination, and thrombin-thrombin-activatable fibrinolysis inhibitor (TAFI)-Thrombomodulin™ combination.

In addition to those described above, the multispecific antigen-binding molecule can reportedly be used in antifungal therapy (Japanese Patent Laid-Open No. 5-199894), immune response induction (National Publication of International Patent Application No. 1998-511085), immunochemistry (R. R. Suresh et al., (1986) Proc. Natl. Acad. Sci. USA 83: 7989-7993; and C. Milstein and A. C. Cuello (1983) Nature 305: 537-540), etc.

In one embodiment, when the multispecific antigen-binding molecule according to the present invention is a bispecific antibody (e.g., IgG) having common L chains, it is preferred to add various alterations or the like for promoting the heterodimerization of two types of H chains. For example, alteration to introduce structures sterically complementary to each other to the CH3 domains of two types of H chains (Ridgway et al., (1996) Protein Eng. 9: 617-21; and WO96/27011), alteration to convert the CH3 domains of two types of H chains to a heterodimer by interdigitating an IgG-derived sequence and an IgA-derived sequence (SEED-bodies: Protein Eng Des Sel. 2010 April; 23 (4): 195-202), and alteration to introduce a mutation so as to cause charge interaction between the CH3 domains of two types of H chains (WO2006/106905) have already been known as such alterations.

In an alternative aspect, the present invention relates to a method for producing an antigen-binding molecule, wherein the method comprises:

(a) contacting helper phages capable of expressing first polypeptides having amino acid sequences identical to the amino acid sequence of a first polypeptide of a reference antigen-binding molecule (parent antigen-binding molecule), which comprises the first polypeptide and a second polypeptide associated with each other and is capable of specifically binding to a predetermined antigen, with a bacterium population capable of expressing second polypeptides having amino acid sequences different from the amino acid sequence of the second polypeptide of the parent antigen-binding molecule to prepare an antigen-binding molecule display library comprising a plurality of bacteriophages displaying antigen-binding molecules (child antigen-binding molecules) comprising the common first polypeptides associated with the second polypeptides differing in amino acid sequence, respectively; and (b) contacting the antigen with the antigen-binding molecule display library prepared in (a) to select a child antigen-binding molecule capable of specifically binding to the antigen.

This method may further comprise:

(c) obtaining a child antigen-binding molecule having physical properties different from those of the parent antigen-binding molecule from among the child antigen-binding molecules selected in (b).

In a further embodiment, the method for producing an antigen-binding molecule may be the method further comprising:

(d) contacting helper phages capable of expressing second polypeptides having amino acid sequences identical to the amino acid sequence of the second polypeptide of the child antigen-binding molecule selected in (b) or obtained in (c) with a bacterium population capable of expressing first polypeptides having amino acid sequences different from the amino acid sequence of the first polypeptide of the child antigen-binding molecule to prepare an antigen-binding molecule display library comprising a plurality of bacteriophages displaying antigen-binding molecules (grandchild antigen-binding molecules) comprising the common second polypeptides associated with the first polypeptides differing in amino acid sequence, respectively; and (e) contacting the antigen with the antigen-binding molecule display library prepared in (d) to select a grandchild antigen-binding molecule capable of specifically binding to the antigen.

This method may further comprise:

(f) obtaining a grandchild antigen-binding molecule having physical properties different from those of the child antigen-binding molecule from among the grandchild antigen-binding molecules selected in (e).

In this context, the physical properties in (c) or (f) may mean, but are not limited to, for example, isoelectric points, heat stability, chemical stability, solubility, viscosity, glycosylation status, the homogeneity of the antigen-binding molecule itself, immunogenicity, and/or affinity or binding specificity for the antigen (J Biol Chem 2005; 280: 24880-7).

In one embodiment, the method for producing an antigen-binding molecule provides an antigen-binding molecule having excellent affinity or binding specificity for the antigen, an antigen-binding molecule having excellent heat stability or chemical stability, an antigen-binding molecule having improved solubility, an antigen-binding molecule free from a glycosylated amino acid sequence, a molecule improved in terms of the homogeneity of the antigen-binding molecule itself, an antigen-binding molecule having reduced immunogenicity (or immunogenic risks), and/or an antigen-binding molecule having a changed isoelectric point or viscosity, as compared with the reference antigen-binding molecule. When the method for producing an antigen-binding molecule provides an antigen-binding molecule having excellent affinity for the antigen, this method relates to a method for affinity-maturing an antigen-binding molecule.

This method is advantages because even if an antibody inferior in physical properties has been obtained by the method, this antibody can be used in, for example, the humanization of a non-human animal-derived antibody (J Mol Biol. 2000 Feb. 25; 296 (3): 833-49). For example, human-derived second polypeptides can be obtained by panning operation for an antigen using fixed non-human animal-derived first polypeptides and a human-derived second polypeptide library in combination. Subsequently, a human-derived first polypeptide can be obtained by panning operation for the antigen using the fixed second polypeptides and a human-derived first polypeptide library in combination. In this way, a human antibody can be obtained on the basis of the non-human animal-derived antibody by the sequential replacement with the human antibody libraries.

It has been reported that, for example, at least one amino acid residue exposable on surface among the amino acid residues of an antibody variable region can be substituted for change in charge (pI: isoelectric point), thereby prolonging or shortening the half-life in blood or average residence time in blood of the antibody or reducing or improving its clearance in blood (WO2007/114319; and WO2009/041643).

It has been reported that, for example, an amino acid residue located at the interface between an H chain variable region and an L chain variable region of an antibody can be altered, thereby improving its heat stability (J Mol Biol. 2003 Jan. 17; 325 (3): 531-53).

It has been reported that, for example, a glutamine residue in an antibody variable region can be substituted by a glutamic acid residue, thereby improving its chemical stability (Anticancer Drugs. 2010 November; 21 (10): 907-16).

It has been reported that, for example, a hydrophobic residue in an antibody variable region can be substituted by a low hydrophobic residue, thereby improving its solubility (Protein Sci. 2010 May; 19 (5): 954-66).

It has also been reported that a N-linked glycosylated sequence can be removed from an antibody variable region, thereby reducing the inhomogeneity of the produced antibody (J Mol Biol. 2011 Oct. 14; 413 (1): 261-78).

Thus, those skilled in the art understand that according to a predetermined purpose, the stability, isoelectric point, etc., of an antibody can be changed by the method for producing an antigen-binding molecule, thereby prolonging or shortening the half-life in blood or average residence time in blood of the antibody or reducing or improving its clearance in blood, for example.

In the case of carrying out the step (c) or the step (f), the method for obtaining an antigen-binding molecule is not particularly limited as long as the method is generally known to those skilled in the art.

For example, antigen-binding molecules each capable of specifically binding to the antigen may be selected through contact with this antigen, and then, an antigen-binding molecule group having the desired physical properties can be evaluated (e.g., assayed or predicted) for the physical properties without panning operation (MAbs. 2011 May-June; 3 (3): 243-52). Alternatively, the antigen-binding molecules may be screened for (narrowed down to) candidates by panning operation, and then, the candidates can be evaluated for the physical properties.

When the "different physical properties" are, for example, affinity for the antigen, ELISA, FACS, Biacore based on surface plasmon resonance, or biolayer interferometry (BLI) such as Octet system used in Examples herein may be used.

When the "different physical properties" are, for example, isoelectric points, the isoelectric points can be calculated (predicted) on the basis of the amino acid sequences of the obtained antigen-binding molecules using commercially available software generally known to those skilled in the art, such as Genetyx. In one embodiment, the isoelectric points can be predicted for the amino acid sequences of antigen-binding molecules having the adequate ability to specifically bind to the antigen to select a molecule having the desired isoelectric point. Alternatively, the isoelectric points may be actually measured using isoelectric focusing (IEF) or the like (Protein Eng Des Sel. 2010 May; 23 (5): 385-92).

When the "different physical properties" are, for example, heat stability or chemical stability, heat is applied to the antigen-binding molecules before panning operation or the antigen-binding molecules are denatured, and then, panning operation may be carried out for the antigen (Methods Mol Biol. 2012; 907: 123-44).

In an alternative aspect, the present invention relates to a combination of an altered helper phage and a bacterium infectible by the helper phage, wherein the helper phage is a helper phage capable of expressing a first polypeptide, and the bacterium is a bacterium capable of expressing a second polypeptide.

The first polypeptide and the second polypeptide according to the present invention associate with each other to form one antigen-binding molecule.

In one embodiment, the combination of a helper phage and a bacterium according to the present invention refers to every combination comprising the helper phage and the bacterium as components on the premise that the helper phage is allowed to infect the bacterium. The present invention also encompasses a combination in which the helper phage and the bacterium exist separately before mixing and thus are not yet ready for infection. Furthermore, the present invention also encompasses a combination in which the helper phage and the bacterium exist in a mixture after mixing and are thus ready for infection.

In an alternative aspect, the present invention also encompasses a method for producing the combination of an altered helper phage and a bacterium infectible by the helper phage according to the present invention. The altered helper phage of the present invention can be prepared by inserting the polynucleotide encoding the first polypeptide to the genomic DNA of a helper phage through the use of a restriction site, and transferring the genomic DNA of the altered helper phage thus prepared to a host bacterium. Examples of the restriction site preferred for the helper phage M13KO7 can include a SacI site positioned between a kanamycin resistance gene and p15A ori, and a SacII site positioned between p15A ori and M13 ori. The bacterium thus harboring the genomic DNA of the altered helper phage produces a phage particle, and the genomic DNA of the altered helper phage is further packaged therein to reconstruct the altered helper phage. Also, the bacterium infectible by the helper phage can be prepared by transferring the polynucleotide encoding the second polypeptide to a bacterium.

In an alternative aspect, the present invention also encompasses an altered helper phage which is included in the combination of an altered helper phage and a bacterium infectible by the helper phage according to the present invention. Specifically, the present invention relates to an altered helper phage capable of expressing a certain polypeptide, wherein the polypeptide is any one of two polypeptides that associate with each other to form an antigen-binding molecule. The present invention also relates to an altered helper phage capable of expressing a first polypeptide, wherein the first polypeptide is capable of associating with a different second polypeptide to form one antigen-binding molecule.

In an alternative aspect, the present invention also encompasses a kit comprising the altered helper phage of the present invention. Specifically, the present invention relates to a kit comprising an altered helper phage capable of expressing a certain polypeptide, wherein the polypeptide is any one of two polypeptides that associate with each other to form an antigen-binding molecule. The present invention also relates to a kit comprising an altered helper phage capable of expressing a first polypeptide, wherein the first polypeptide is capable of associating with a different second polypeptide to form one antigen-binding molecule. These kits can each be a kit for preparing a bacteriophage displaying an antigen-binding molecule, a kit for preparing an antigen-binding molecule display library comprising common first polypeptides, a kit for obtaining an antigen-binding molecule specifically binding to a predetermined antigen, a kit for preparing a multispecific antigen-binding molecule comprising common first polypeptides, or a kit for producing an antigen-binding molecule having physical properties different from those of a reference antigen-binding molecule. The kit of the present invention may further comprise a bacterium infectible by the helper phage, wherein the bacterium is capable of expressing the remaining one polypeptide of the two polypeptides that form an antigen-binding molecule, or a bacterium infectible by the helper phage, wherein the bacterium is capable of expressing the second polypeptide.

Those skilled in the art should understand one of or any combination of two or more of the aspects described herein is also included in the present invention unless a technical contradiction arises on the basis of the common technical knowledge of those skilled in the art.

All prior technical literatures cited herein are incorporated herein by reference.

Terms such as "first" or "second" are used for expressing various factors. However, these factors are understood to be not limited by these terms. These terms are used merely for differentiating one factor from the other factors. For example, the first factor may be described as the second factor, and vice versa, without departing from the scope of the present invention.

The terms used herein are used for illustrating particular embodiments and are not intended to limit the invention by any means. The terms (including technical terms and scientific terms) used herein are interpreted to have the same meanings as those understood in a broad sense by those skilled in the art to which the present invention belongs, unless otherwise defined. These terms should not be interpreted in an idealized or excessively formal sense.

The term "comprising" used herein means that described items (members, steps, factors, numbers, etc.) are present and the presence of the other items (members, steps, factors, numbers, etc.) is not excluded therefrom, unless the context evidently requires different interpretation.

The embodiments of the present invention may be described with reference to a schematic diagram, which may be exaggerated for the purpose of clear illustration.

The numeric values described herein are understood as values having given ranges according to the common technical knowledge of those skilled in the art, unless inconsistent to the context. For example, the term "1 mg" is understood to represent "approximately 1 mg" and is understood to include a given variation. For example, the term "1 to 5" described herein is understood to concretely describe the individual values of "1, 2, 3, 4, and 5", unless inconsistent to the context.

EXAMPLES

The present invention will be further illustrated with reference to Examples described below. However, the present invention is not intended to be limited by Examples below.

Example 1

Establishment of Method for Producing Fab-Displaying Phage by Combination of H Chain-Expressing Phagemid Vector and L Chain-Expressing Helper Phage (1-1) Construction of L Chain-Expressing Helper Phage Carrying L Chain Expression Unit A promoter, a signal sequence gene, an antibody L chain gene, etc., were incorporated to the genome of a helper phage to construct an L chain-expressing helper phage. The antibody L chain can be expressed from *E. coli* infected with this helper phage.

Specifically, an *E. coli* strain XL1-Blue was infected with a helper phage (M13KO7; Invitrogen Corp.) and shake-cultured overnight, followed by the genome extraction of the helper phage (QIAprep Spin Miniprep Kit; Qiagen N.V.). The helper phage genome has a BamHI site at the N2 domain of gene 3 and a PacI site at gene 1. The obtained helper phage genome was cleaved with BamHI and PacI, then electrophoresed on 0.6% agarose gel, and purified by gel extraction (Wizard SV Gel and PCR Clean-Up system; Promega Corp.) to prepare each of a DNA fragment from gene 3 to gene 1 and a DNA fragment of the remaining genome. The prepared DNA fragment from gene 3 to gene 1 was used as a template in PCR to newly prepare a DNA fragment having an insert of a DNA encoding a trypsin cleavage sequence between the N2 domain and the CT domain of gene 3. The amino acid sequence encoded by the gene 3 before the alteration is shown in SEQ ID NO: 1, and the amino acid sequence encoded by the altered gene 3 is shown in SEQ ID NO: 2. This DNA fragment was religated with the preliminarily prepared DNA fragment of the remaining genome to construct a helper phage M13KO7TC having an insert of the trypsin cleavage sequence between the N2 domain and the CT domain of the pIII protein on the helper phage (see National Publication of International Patent Application No. 2002-514413).

An *E. coli* strain ER2738 was infected with the helper phage M13KO7TC and shake-cultured overnight, followed by the genome extraction of the helper phage M13KO7TC from the infected *E. coli* (NucleoBond Xtra Midi Plus). A SacI site positioned between a kanamycin resistance gene and p15A ori was selected as the site to which the L chain expression unit was inserted (FIG. 1). The insertion site is not limited to this site and may be, for example, a SacII site positioned between p15A ori and M13 ori without problems. The genome of the helper phage M13KO7TC purified by the aforementioned method was cleaved with SacI, then electrophoresed on 0.6% agarose gel, and purified by gel extraction (Wizard SV Gel and PCR Clean-Up system; Promega Corp.) to obtain the DNA fragment (M13KO7TC/SacI) of interest.

The L chain of an anti-human IL-6R antibody PF1 was used as the antibody L chain (VL and CL) to be introduced. In this respect, the substitution of the C-terminal Cys of the L chain constant region by Ala is known to be advantageous for Fab expression in *E. coli* (J Biol Chem. 2003 Oct. 3; 278 (40): 38194-38205). Therefore, such a sequence was used. lac promoter—pelB signal sequence gene—PF1 L chain gene was inserted to M13KO7TC/SacI by the in-fusion method (In-Fusion HD Cloning Kit; Clontech Laboratories, Inc.), which was then transferred to an *E. coli* strain ER2738 by the electroporation method. The nucleic acid sequence of the lac promoter is shown in SEQ ID NO: 3. The amino acid sequence of the pelB signal sequence and the nucleic acid sequence encoding it are shown in SEQ ID NO: 4 and SEQ ID NO: 5, respectively. The amino acid sequence of the PF1 L chain and the nucleic acid sequence encoding it are shown in SEQ ID NO: 6 and SEQ ID NO: 7, respectively.

The obtained *E. coli* was cultured. 2.5 M NaCl/10% PEG was added to the culture supernatant, and the helper phage was purified by the PEG precipitation method. The titer of the obtained helper phage M13KO7TC-PF1L was confirmed by the general plaque formation method.

(1-2) Construction of H Chain-Expressing Phagemid Vector

A phagemid vector for expressing an antibody H chain on phage surface was constructed. The phagemid vector was prepared by functionally inserting a packaging signal gene for phage particles, a promoter, a signal sequence gene, an antibody H chain gene, a linker gene, gene 3, etc., to a plasmid vector. The antibody H chain was fused with the gene 3 protein (g3p) via the linker peptide. The H chain of an anti-human IL-6R antibody PF1 was used as the antibody H chain (Fd consisting of VH and CH1) to be introduced. The amino acid sequence of the PF1 H chain is shown in SEQ ID NO: 8. The constructed phagemid vector was transferred to an *E. coli* strain ER2738 by the electroporation method to construct *E. coli* ER2738/pAG-PF1H carrying the PF1 H chain-expressing phagemid vector.

(1-3) Production of Fab-Displaying Phage by Combination of H Chain-Expressing Phagemid Vector and L Chain-Expressing Helper Phage The *E. coli* ER2738/pAG-PF1H was cultured until OD reached around 0.5, and then infected with the helper phage M13KO7TC-PF1L or M13KO7TC. After medium replacement, the *E. coli* was cultured overnight at 30° C., and the culture supernatant was recovered. 2.5 M NaCl/10% PEG was added to the *E. coli* culture solution containing the produced phage to precipitate the phage, which was then dissolved in TBS to obtain a phage solution. The titer of the obtained phage was confirmed by the general colony formation method.

(1-4) Confirmation of Fab Display on Phage by Phage ELISA Method

The phage ELISA method was carried out to confirm Fab display on the produced phage and to confirm the ability to bind to the antigen. StreptaWell 96-well microtiter plate (F. Hoffmann-La Roche, Ltd.) was coated by the addition of 100 µL of PBS containing Goat anti-Human Kappa Biotin antibody (EY Laboratories, Inc.) or biotinylated human IL-6R. Each well of the plate was washed with 0.1×TBST (0.1× TBS containing 0.1% Tween 20) to remove the antigen. Then, the plate was blocked for 1 hour or longer by the addition of 250 µL of 0.02% skim milk-0.1×TBS (0.1×TBS containing 0.02% skim milk) to the well. After removal of the 0.02% skim milk-0.1×TBS, the phage solution diluted with 0.02% skim milk-0.1×TBS was added to each well, and the plate was left standing at 37° C. for 1 hour so that the antibody displayed on the phage bound to the Goat anti-Human Kappa Biotin antibody or the biotinylated human IL-6R. After washing with 0.1×TBST, an HRP-conjugated anti-M13 antibody (Amersham Pharmacia Biotech) diluted with 0.1×TBST was added to each well, and the plate was incubated for 1 hour. After washing with 0.1×TBST, TMB single solution (Zymed Laboratories Inc.) was added to each well. The color reaction of the solution was further terminated by the addition of sulfuric acid. Then, the absorbance was measured at 450 nm.

Figure 2:
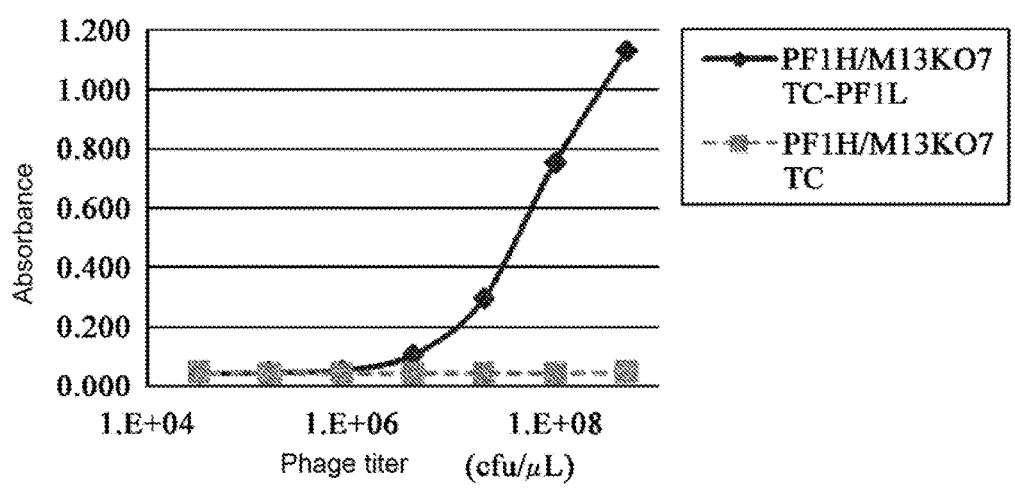
FIG. 2 is a diagram showing results of conducting ELISA using an anti-human κ chain antibody for a phage produced by a combination of an H chain (PF1H)-expressing phagemid vector and an L chain (PF1L)-expressing helper phage. In the case of using the L chain-expressing helper phage (M13KO7TC-PF1L), Fab was confirmed to be displayed on the phage. On the other hand, in the case of using a negative control helper phage (M13KO7TC), no Fab was confirmed to be displayed on the phage.
Figure 3:
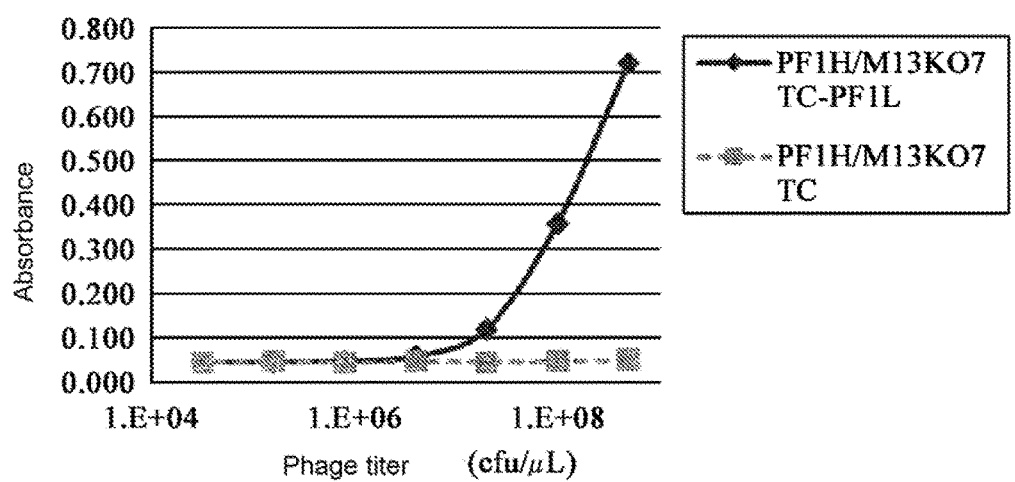
FIG. 3 is a diagram showing results of conducting ELISA using human IL-6R as an antigen for a phage produced by a combination of an H chain (PF1H)-expressing phagemid vector and an L chain (PF1L)-expressing helper phage. In the case of using the L chain-expressing helper phage (M13KO7TC-PF1L), the Fab-displaying phage was confirmed to have the ability to bind to the antigen. On the other hand, in the case of using a negative control helper phage (M13KO7TC), its binding to the antigen was not observed.

As a result, it was confirmed that: Fab was displayed on the phage only when the phage was produced by the combination of the H chain-expressing phagemid vector and the L chain-expressing helper phage M13KO7TC-PF1L (FIG. 2); and Fab displayed on the phage maintained the ability to bind to the antigen (FIG. 3).

Example 2

Construction of Phagemid Library Comprising Naive H Chains and Production of Fab Phage Library Comprising Naive H Chains and PF1 L Chains Naive H chain variable region genes were amplified by PCR using poly-A RNA prepared form human peripheral blood mononuclear cells (PBMCs), commercially available human poly-A RNA, or the like as a template. These genes were inserted to phagemid vectors, and the constructed phagemid vectors were transferred to an *E. coli* strain ER2738 by the electroporation method. Consequently, approximately $1.1 \times 10^{10}$ colonies were obtained.

These *E. coli* colonies were infected with the helper phage M13KO7TC-PF1L constructed in Example 1 and cultured to construct a human antibody phage display library (NH-PF1L library) displaying Fabs comprising naive H chains and PF1 L chains.

Example 3

Obtainment of Fabs Having PF1 L Chains and being Capable of Binding to Various Antigens (3-1) Preparation of Biotinylated Human Plexin A1

The extracellular region of a single-pass transmembrane protein human Plexin A1 (hPlexin A1) was prepared as follows: hPlexin A1 gene synthesized on the basis of the amino acid sequence of NCBI Reference Sequence NP_115618 (SEQ ID NO: 9) was altered to encode a protein lacking the presumed transmembrane region starting at alanine at position 1245 and subsequent regions and instead having an added FLAG tag sequence (SEQ ID NO: 13). The signal peptide (SEQ ID NO: 14) from positions 1 to 26 was further substituted by an artificial signal peptide HMM+38 (SEQ ID NO: 15). The prepared gene encoding the altered hPlexin A1 (SEQ ID NO: 10) was integrated into an expression vector for animal cells, which was then transferred to FreeStyle 293 cells (Invitrogen Corp.) using 293Fectin (Invitrogen Corp.). In this operation, the cells were cotransfected with the expression vector and a gene encoding EBNA1 (SEQ ID NO: 17) in order to improve the expression efficiency of the gene of interest. The cells transfected according to the aforementioned procedures were cultured at 37° C. for 6 days in an 8% $CO_2$ environment so that the protein of interest was secreted into the culture supernatant.

The cell culture solution containing the hPlexin A1 of interest was filtered through a 0.22 μm bottle-top filter to obtain a culture supernatant. The culture supernatant was applied to Anti-FLAG Antibody M2 Agarose (Sigma-Aldrich Corp.) equilibrated with D-PBS(−) (Wako Pure Chemical Industries, Ltd.). Then, D-PBS containing a FLAG peptide dissolved therein was added thereto to elute the hPlexin A1 of interest. Next, the fraction containing the hPlexin A1 was separated by gel filtration chromatography using Superdex 200 (GE Healthcare Japan Corp.) equilibrated with D-PBS(−).

EZ-Link NHS-PEG4-Biotin (Thermo Fisher Scientific Inc.) was used for the hPlexin A1 thus prepared to prepare biotinylated hPlexin A1.

(3-2) Preparation of Biotinylated Mouse IgA-Fc Region

For the purpose of biotinylating the C terminus of a mouse IgA Fc region (mIgA-Fc: CH2 and CH3 domains of mouse IgA, SEQ ID NO: 11), a gene fragment encoding a specific sequence (AviTag sequence, SEQ ID NO: 16) for biotin ligase-mediated biotinylation was linked via a linker to downstream of a gene fragment encoding mIgA-Fc. The gene fragment encoding a protein containing the mIgA-Fc and the AviTag sequence linked (mIgA_CH2-CH3-Avitag (SEQ ID NO: 12)) was integrated to a vector for expression in animal cells, and the constructed plasmid vector was transferred to FreeStyle 293 cells (Invitrogen Corp.) using 293Fectin (Invitrogen Corp.). In this operation, the cells were cotransfected with the expression vector and a gene encoding EBNA1 (SEQ ID NO: 17) and a gene encoding biotin ligase (BirA, SEQ ID NO: 18), and biotin was further added for the purpose of biotinylating mIgA-Fc. The cells transfected according to the aforementioned procedures were cultured at 37° C. for 6 days in an 8% $CO_2$ environment so that the protein of interest was secreted into the culture supernatant.

The cell culture solution containing the mIgA-Fc of interest was filtered through a 0.22 μm bottle-top filter to obtain a culture supernatant. The culture supernatant diluted with 20 mM Tris-HCl (pH 7.4) was applied to HiTrap Q HP (GE Healthcare Japan Corp.) equilibrated with 20 mM Tris-HCl (pH 7.4). The mIgA-Fc of interest was eluted by the concentration gradient of NaCl. Next, the HiTrap Q HP eluate diluted with 50 mM Tris-HCl (pH 8.0) was applied to SoftLink Avidin column (Promega Corp.) equilibrated with 50 mM Tris-HCl (pH 8.0). The mIgA-Fc of interest was eluted with 5 mM biotin, 150 mM NaCl, and 50 mM Tris-HCl (pH 8.0). Then, undesired impurities mIgA-Fc associates were removed by gel filtration chromatography using Superdex 200 (GE Healthcare Japan Corp.) to obtain purified mIgA-Fc with the buffer replaced with 20 mM histidine-HCl and 150 mM NaCl (pH 6.0).

(3-3) Preparation of Biotinylated Human IL-6R

For the purpose of biotinylating the C terminus of soluble human IL-6R (hIL-6R, SEQ ID NO: 19), a gene fragment encoding a specific sequence (AviTag sequence, SEQ ID NO: 16) for biotin ligase-mediated biotinylation was linked via a linker to downstream of a gene fragment encoding soluble hIL-6R. The gene fragment encoding a protein containing the soluble hIL-6R and the AviTag sequence linked (shIL6R-Avitag, SEQ ID NO: 20) was integrated to a vector for expression in animal cells, and the constructed plasmid vector was transferred to FreeStyle 293 cells (Invitrogen Corp.) using 293Fectin (Invitrogen Corp.). In this operation, the cells were cotransfected with the expression vector and a gene encoding EBNA1 (SEQ ID NO: 17) and a gene encoding biotin ligase (BirA, SEQ ID NO: 18), and biotin was further added for the purpose of biotinylating soluble hIL-6R. The cells transfected according to the aforementioned procedures were cultured at 37° C. in an 8% $CO_2$ environment so that the protein of interest was secreted into the culture supernatant.

Biotinylated hIL-6R was obtained by purification in the same way as in the paragraph (3-2) from the cell culture solution containing the soluble hIL-6R of interest.

(3-4) Obtainment of Antibody Fragments Binding to Various Antigens (Human Plexin A1, Mouse IgA-Fc, and Human IL-6R) from NH-PF1L Library The antibody library comprising PF1 L chains (NH-PF1L library) constructed in Example 2 was screened for antibody fragments binding to various antigens (hPlexin A1, mIgA-Fc, and hIL-6R) with the ability to bind to each antigen as an index.

The *E. coli* carrying the phagemid vectors having inserts of the human naive H chain genes was infected with the helper phage M13KO7TC-PF1L and cultured to construct a human antibody phage display library (NH-PF1L library) displaying Fabs comprising human antibody H chains and PF1 L chains. 2.5 M NaCl/10% PEG was added to the *E. coli* culture solution containing the produced phages to precipitate the phages, which were then diluted with TBS to obtain a phage library solution. Next, the phage library solution was blocked by the addition of BSA (final concentration: 4%) to the phage library solution. The panning method was used with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2), 212-220; and Mol. Cell Proteomics (2003) 2 (2), 61-69). The magnetic beads used were NeutrAvidin coated beads (Sera-Mag SpeedBeads NeutrAvidin-coated) or Streptavidin coated beads (Dynabeads M-280 Streptavidin). Specifically, each biotinylated antigen (biotinylated hPlexin A1, biotinylated mIgA-Fc, and biotinylated hIL-6R) was added to the prepared phage library solution, and the antigen was contacted with the phage library solution at room temperature for 60 minutes. The biotinylated antigen was used at 250 pmol for the first panning, 40 pmol for the second panning, and 10 pmol for the third panning. The magnetic beads blocked with a BSA solution were added thereto, and the magnetic beads were allowed to bind to the antigen-phage complexes at room temperature for 15 minutes. The recovered beads were washed with 1 mL of TBST (TBS containing 0.1% Tween 20) and 1 mL of TBS. Then, 0.5 mL of a 1 mg/mL trypsin solution was added to the beads. Immediately after suspension at room temperature for 15 minutes, the beads were separated using a magnetic stand to recover the phage solution in the supernatant. The recovered phage solution was added to 10 mL of an *E. coli* strain ER2738 cultured until the logarithmic growth phase (OD600=0.4-0.7). The *E. coli* was cultured by mild stirring at 37° C. for 1 hour and thereby infected with the phage. The infected *E. coli* was inoculated to a 225 mm×225 mm plate. Next, the inoculated *E. coli* was recovered and cultured. Then, the *E. coli* was infected with the helper phage M13KO7TC-PF1L and cultured to produce phages displaying Fabs comprising PF1 L chains. The phages were recovered from the culture solution to prepare a phage library solution. This operation was defined as one round of panning, and a total of 3 rounds of panning was repetitively carried out.

(3-5) Screening for Antibodies Binding to Various Antigens (Human Plexin A1, Mouse IgA-Fc, and Human IL-6R) by Phage ELISA Method Phage production was performed according to a routine method (Methods Mol. Biol. (2002) 178, 133-145) from the *E. coli* single colony obtained after the completion of the 2 or 3 rounds of panning carried out in the paragraph (3-4). A phage-containing culture supernatant was recovered. In this operation, M13KO7TC-PF1L was used as a helper phage. The culture supernatant was subjected to ELISA by the following procedures.

StreptaWell 96-well microtiter plate (F. Hoffmann-La Roche, Ltd.) was coated overnight with 100 µL of PBS containing or not containing each biotinylated antigen (hPlexin A1, mIgA-Fc, and hIL-6R). Each well of the plate was washed with 0.1×TBST (0.1×TBS containing 0.1% Tween 20) to remove the antigen. Then, each well was blocked for 1 hour or longer with 250 µL of 0.02% skim milk-0.1×TBS (0.1×TBS containing 0.02% skim milk). After removal of the 0.02% skim milk-0.1×TBS, the phage culture supernatant was added to each well, and the plate was left standing at 37° C. for 1 hour so that the antibody displayed on the phage bound to the biotinylated antigen present in each well. After washing of each well with 0.1×TBST, an HRP-conjugated anti-M13 antibody (Amersham Pharmacia Biotech) diluted with 0.1×TBST was added to each well, and the plate was incubated for 1 hour. After washing of each well with TBST, TMB single solution (Zymed Laboratories Inc.) was added to each well. The color reaction of the solution was further terminated by the addition of sulfuric acid. Then, the absorbance of each well was measured at 450 nm.

As a result of the phage ELISA, a clone was confirmed to specifically bind to the antigen when the coloring ratio of the antigen-coated plate to the antigen-uncoated plate was 2 or more times and the color developed by the antigen-coated plate was 0.2 or more. The clone confirmed to specifically bind to the antigen was further analyzed for the nucleotide sequence of the antibody fragment gene.

The results of the phage ELISA are shown in Table 1. In the table, R2 represents the results about clones after the completion of 2 rounds of panning, and R3 represents the results about clones after the completion of 3 rounds of panning. As a result, a plurality of clones specifically binding to each antigen hPlexin A1, mIgA-Fc, or hIL-6R and differing in sequence were obtained.

TABLE 1

|  | hPlexinA1 | | mIgA-Fc | | hIL-6R | |
| --- | --- | --- | --- | --- | --- | --- |
|  | R2 | R3 | R2 | R3 | R2 | R3 |
| The number of evaluated clones | 94 | 94 | 94 | 94 | 94 | 94 |
| The number of antigen-specific clones | 39 | 75 | 4 | 34 | 42 | 92 |
| The type of sequence of antigen-specific clone | 7 | 4 | 1 | 2 | 26 | 9 |

Example 4

Evaluation of Various Antigen-Binding Antibodies Having PF1 L Chains for Ability to Bind Through IgG (4-1) Expression and Purification of Obtained Various Antigen (Human Plexin A1, Mouse IgA-Fc, and Human IL-6R)-Binding Antibodies Having PF1 L Chains Four antibodies 6RNH-2_02 (heavy chain: SEQ ID NO: 21), 6RNH-2_37 (heavy chain: SEQ ID NO: 22), 6RNH-3 (2) 32 (heavy chain: SEQ ID NO: 23), and 6RNH-2_42 (heavy chain: SEQ ID NO: 24) among the antibodies obtained as antibodies binding to human IL-6R, three antibodies PANH-2_52 (heavy chain: SEQ ID NO: 25), PANH-2_68 (heavy chain: SEQ ID NO: 26), and PANH-3_10 (heavy chain: SEQ ID NO: 27) among the antibodies obtained as antibodies binding to human plexin A1, and two antibodies mIANH-2_27 (heavy chain: SEQ ID NO: 28) and mIANH-3_79 (heavy chain: SEQ ID NO: 29) among the antibodies obtained as antibodies binding to mouse IgA-Fc in Example 3 were expressed using the method given below, and these antibodies were purified. All of these antibodies are antibodies having PF1 L chains (light chain: SEQ ID NO: 67) as light chains. An anti-IL-6R antibody PF1 antibody (heavy chain: SEQ ID NO: 68; light chain: SEQ ID NO: 67) was also expressed as a control using the method given below, and this antibody was purified. 3 mL of a human embryonic kidney cell-derived FreeStyle 293-F line (Invitrogen Corp.) suspended in FreeStyle 293 Expression Medium (Invitrogen Corp.) was inoculated at a cell density of $1.33 \times 10^6$ cells/mL to each well of a 6-well plate. The prepared plasmids were transferred to the cells by the lipofection method. The cells were cultured for 4 days in a $CO_2$ incubator (37° C., 8% $CO_2$, 90 rpm). Each antibody was purified from the culture supernatant thus obtained by use of a method generally known to those skilled in the art using rProtein A Sepharose™ Fast Flow (Amersham Biosciences Corp.). The absorbance of the purified antibody solution was measured at 280 nm using a spectrophotometer. From the obtained measurement value, the antibody concentration was calculated by use of an extinction coefficient calculated by PACE (Protein Science (1995) 4, 2411-2423).

(4-2) Evaluation of Obtained Antibody for Ability to Bind to Soluble Human IL-6R Each antibody (6RNH-2_02, 6RNH-2_37, 6RNH-3(2)_32, and 6RNH-2_42) obtained in the paragraph (4-1) was evaluated for its binding activity against soluble human IL-6R using Octet RED384 (forteBIO). The binding evaluation was conducted using HBS-EP+ Buffer (GE Healthcare Japan Corp.) as a buffer.

Figure 4:
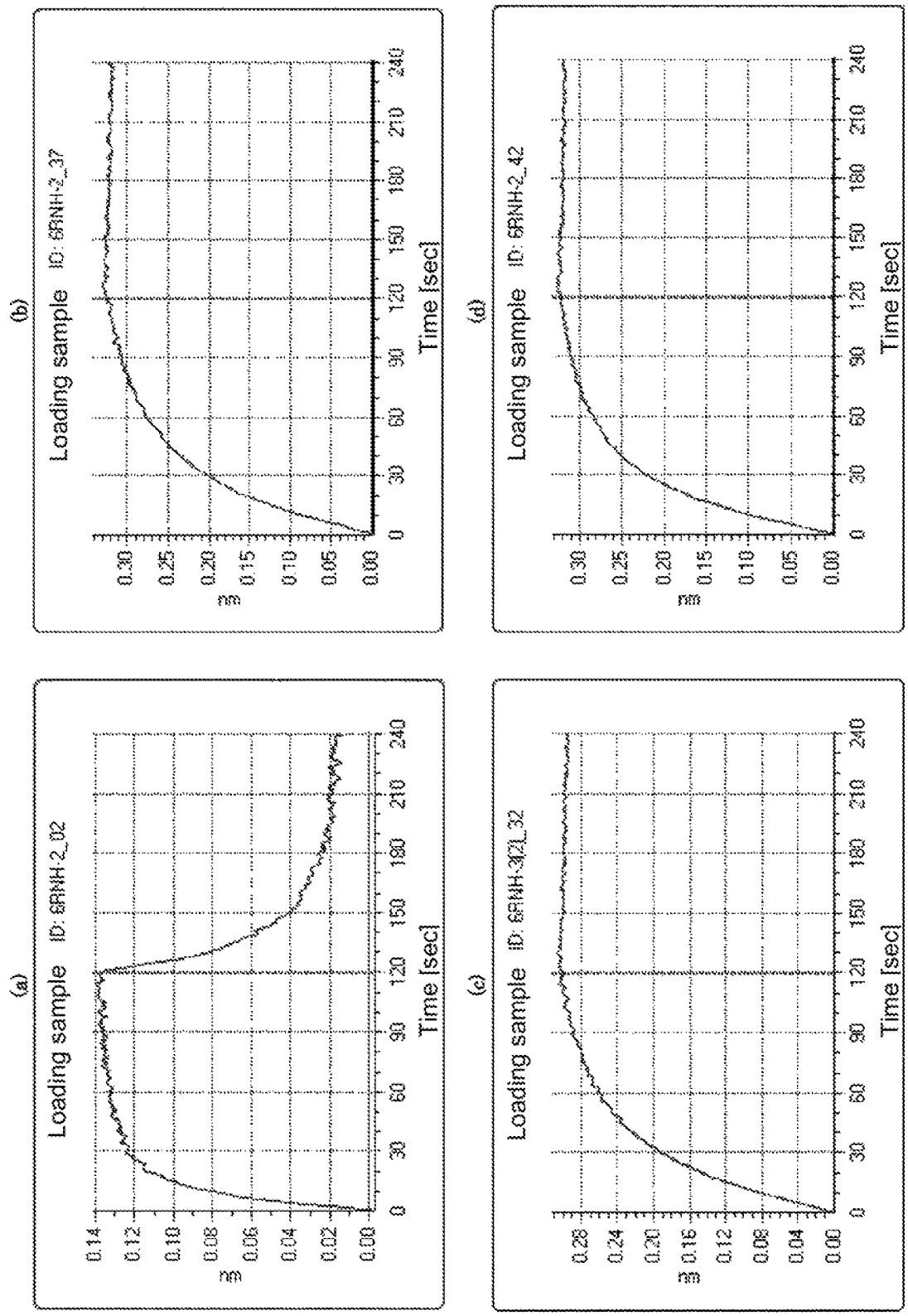
FIG. 4 is a diagram showing results of evaluating obtained antibodies 6RNH-2_02 (FIG. 4(a)), 6RNH-2_37 (FIG. 4(b)), 6RNH-3(2)_32 (FIG. 4(c)), and 6RNH-2_42 (FIG. 4(d)) for their binding activity against soluble human IL-6R using Octet RED384 (forteBIO).

After binding of the antibody to Protein G Biosensors (forteBIO), soluble human IL-6R was allowed to interact with the antibody on the biosensor through contact therebetween for 120 seconds, and subsequently contacted with the buffer for 120 seconds to measure the antibody-antigen interaction. Then, the biosensor was regenerated through contact with 10 mmol/L glycine-HCl (pH 1.5). The measurement was conducted at 30° C. The obtained sensorgram is shown in FIG. 4. All of the antibodies 6RNH-2_02, 6RNH-2_37, 6RNH-3(2)_32, and 6RNH-2_42 were found to bind to soluble human IL-6R.

(4-3) Evaluation of Obtained Antibody for Ability to Bind to Soluble Human Plexin A1

Each antibody (PANH-2_52, PANH-2_68, and PANH-3_10) obtained in the paragraph (4-1) or an anti-human IL-6R antibody PF1 antibody was evaluated for its binding activity against soluble human plexin A1 and soluble human IL-6R using Octet RED384 (forteBIO). The binding evaluation was conducted using HBS-EP+Buffer (GE Healthcare Japan Corp.) as a buffer.

Figure 5:
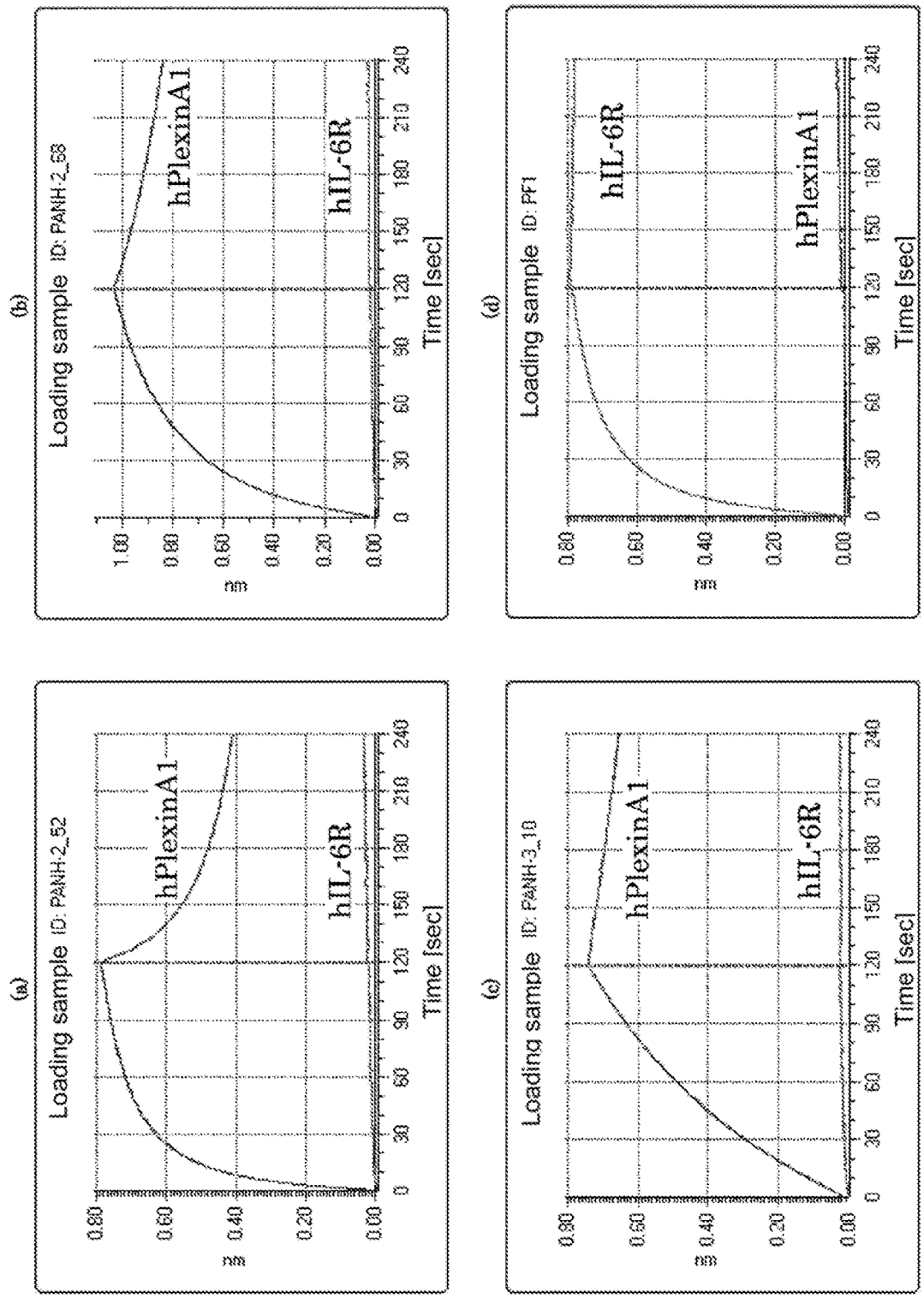
FIG. 5 is a diagram showing results of evaluating obtained antibodies PANH-2_52 (FIG. 5(a)), PANH-2_68 (FIG. 5(b)), PANH-3_10 (FIG. 5(c)), and PF1 antibody (FIG. 5(d)) for their binding activity against soluble human plexin A1 and soluble human IL-6R using Octet RED384 (forteBIO).

After binding of the antibody to Protein G Biosensors (forteBIO), soluble human plexin A1 or soluble human IL-6R was allowed to interact with the antibody on the biosensor through contact therebetween for 120 seconds, and subsequently contacted with the buffer for 120 seconds to measure the antibody-antigen interaction. Then, the biosensor was regenerated through contact with 10 mmol/L glycine-HCl (pH 1.5). The measurement was conducted at 30° C. The obtained sensorgram is shown in FIG. 5. All of the antibodies PANH-2_52, PANH-2_68, and PANH-3_10 were found to bind to soluble human plexin A1 without binding to soluble human IL-6R.

(4-4) Evaluation of Obtained Antibody for Ability to Bind to Mouse IgA

Each antibody (mIANH-2_27 and mIANH-3_79) obtained in the paragraph (4-1) or a PF1 antibody was evaluated for its binding activity against mouse IgA or soluble human IL-6R using Octet RED384 (forteBIO). The binding evaluation was conducted using HBS-EP+Buffer (GE Healthcare Japan Corp.) as a buffer.

Figure 6:
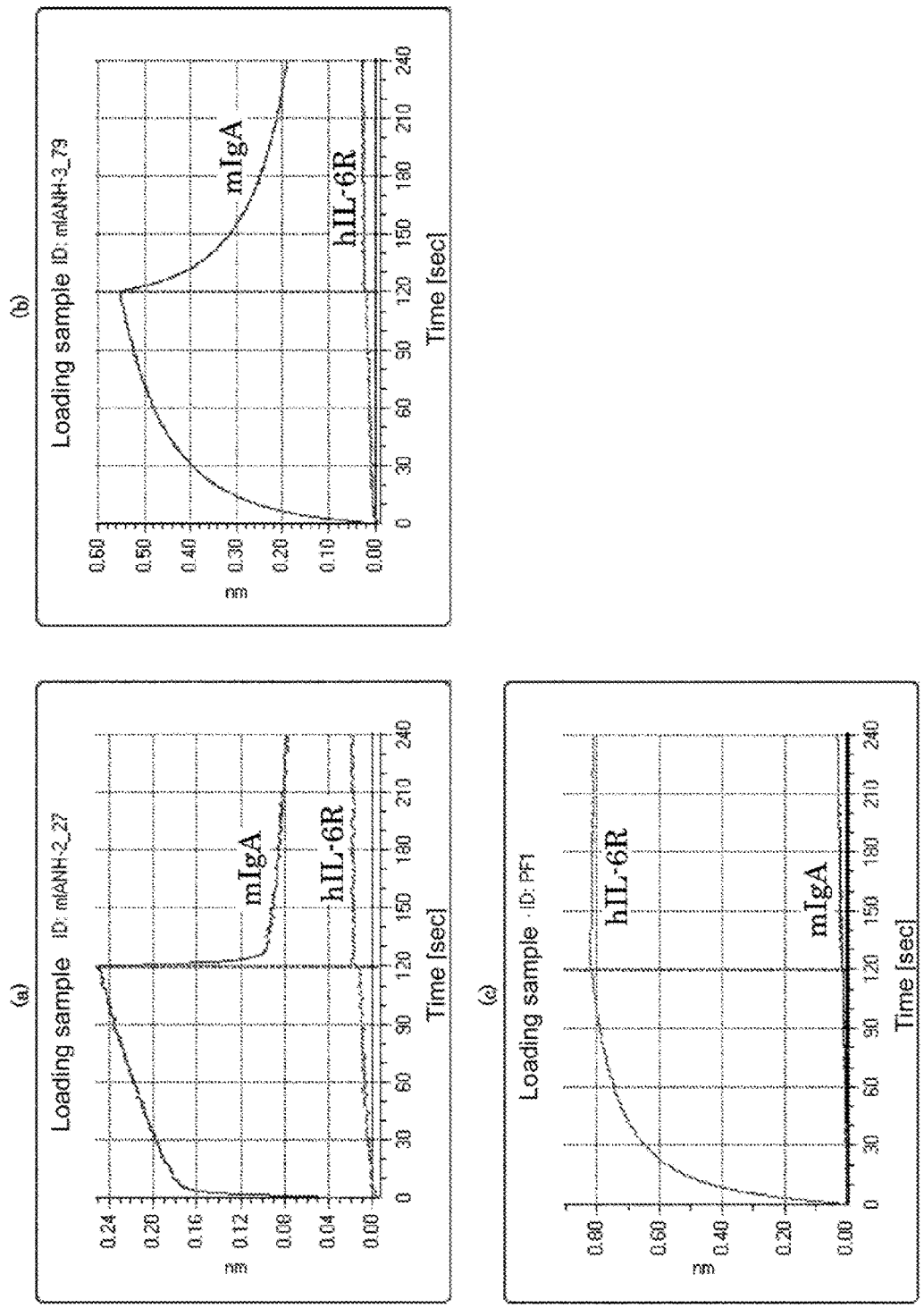
FIG. 6 is a diagram showing results of evaluating obtained antibodies mIANH-2_27 (FIG. 6(a)), mIANH-3_79 (FIG. 6(b)), and PF1 antibody (FIG. 6(c)) for their binding activity against mouse IgA and soluble human IL-6R using Octet RED384 (forteBIO).

After binding of the antibody to Protein G Biosensors (forteBIO), mouse IgA or soluble human IL-6R was allowed to interact with the antibody on the biosensor through contact therebetween for 120 seconds, and subsequently contacted with the buffer for 120 seconds to measure the antibody-antigen interaction. Then, the biosensor was regenerated through contact with 10 mmol/L glycine-HCl (pH 1.5). The measurement was conducted at 30° C. The obtained sensorgram is shown in FIG. 6. All of the antibodies mIANH-2_27 and mIANH-3_79 were found to bind to mouse IgA without binding to soluble human IL-6R.

Example 5

Obtainment of Fabs Having Fixed L Chains and being Capable of Binding to IL-6R (5-1) Production of Fab Phage Library Having Fixed L Chains (L Chains Having Identical Amino Acid Sequences)

The method described in Example 1 was carried out to construct M13KO7TC-PAL as a helper phage expressing the L chain (SEQ ID NO: 30) of an anti-human plexin A1 antibody hPANKB2-3#135, M13KO7TC-IAL as a helper phage expressing the L chain (SEQ ID NO: 31) of an anti-mouse IgA antibody mIANMIgL_095, and M13KO7TC-CEL as a helper phage expressing the L chain L0000 (SEQ ID NO: 32) of a humanized anti-human CD3 antibody CE115.

The *E. coli* harboring the phagemid library comprising naive H chains described in Example 2 was infected with each helper phage described above to construct a human antibody phage display library (NH-PAL library) displaying Fabs comprising naive H chains and anti-plexin A1 antibody L chains, a human antibody phage display library (NH-IAL library) displaying Fabs comprising naive H chains and anti-mouse IgA antibody L chains, and a human antibody phage display library (NH-CEL library) displaying Fabs comprising naive H chains and anti-CD3 antibody L chains. 2.5 M NaCl/10% PEG was added to the *E. coli* culture solutions containing the produced phages to precipitate the phages, which were then diluted with TBS to obtain phage library solutions.

(5-2) Obtainment of Antibody Fragment Binding to IL-6R from Fixed L Chain Antibody Libraries (NH-PAL Library, NH-IAL Library, and NH-CEL Library)

The phage library solution of each fixed L chain antibody library (NH-PAL library, NH-IAL library, and NH-CEL library) constructed in the paragraph (5-1) was screened for antibody fragments binding to human IL-6R with the ability to bind to human IL-6R as an index.

Each phage library solution was blocked by the addition of BSA (final concentration: 4%) to the phage library solution. The panning method was used with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2), 212-220; and Mol. Cell Proteomics (2003) 2 (2), 61-69). The magnetic beads used were NeutrAvidin coated beads (Sera-Mag SpeedBeads NeutrAvidin-coated) or Streptavidin coated beads (Dynabeads M-280 Streptavidin). Specifically, the biotinylated antigen (biotinylated hIL-6R) was added to the prepared phage library solution, and the antigen was contacted with the phage library solution at room temperature for 60 minutes. The biotinylated antigen was used at 250 pmol for the first panning, 40 pmol for the second panning, and 10 pmol for the third panning. The magnetic beads blocked with a BSA solution were added thereto, and the magnetic beads were allowed to bind to the antigen-phage complexes at room temperature for 15 minutes. The recovered beads were washed with 1 mL of TBST (TBS containing 0.1% Tween 20) and 1 mL of TBS. Then, 0.5 mL of a 1 mg/mL trypsin solution was added to the beads. Immediately after suspension at room temperature for 15 minutes, the beads were separated using a magnetic stand to recover the phage solution in the supernatant. The recovered phage solution was added to 10 mL of an E. coli strain ER2738 cultured until the logarithmic growth phase (OD600=0.4-0.7). The E. coli was cultured by mild stirring at 37° C. for 1 hour and thereby infected with the phage. The infected E. coli was inoculated to a 225 mm×225 mm plate. Next, the inoculated E. coli was recovered and cultured. Then, the E. coli was infected with the helper phage (M13KO7TC-PAL, M13KO7TC-IAL, or M13KO7TC-CEL) and cultured to produce phages displaying Fabs comprising anti-plexin A1 antibody L chains, anti-mouse IgA antibody L chains, or anti-CD3 antibody L chains. The phages were recovered from the culture solution to prepare a phage library solution. This operation was defined as one round of panning, and a total of 3 rounds of panning was repetitively carried out.

(5-3) Screening for Antibody Binding to Antigen (Human IL-6R) by Phage ELISA Method Phage production was performed according to a routine method (Methods Mol. Biol. (2002) 178, 133-145) from the E. coli single colony obtained after the completion of the 2 or 3 rounds of panning carried out in the paragraph (5-2). A phage-containing culture supernatant was recovered. In this operation, M13KO7TC-PAL, M13KO7TC-IAL, or M13KO7TC-CEL was used as a helper phage according to the phage library used. The culture supernatant was subjected to ELISA by the following procedures.

StreptaWell 96-well microtiter plate (F. Hoffmann-La Roche, Ltd.) was coated overnight with 100 μL of PBS containing or not containing the biotinylated antigen (biotinylated hIL-6R). Each well of the plate was washed with 0.1×TBST (0.1×TBS containing 0.1% Tween 20) to remove the antigen. Then, each well was blocked for 1 hour or longer with 250 of 0.02% skim milk-0.1×TBS (0.1×TBS containing 0.02% skim milk). After removal of the 0.02% skim milk-0.1×TBS, the phage culture supernatant was added to each well, and the plate was left standing for 1 hour so that the antibody displayed on the phage bound to the biotinylated antigen present in each well. After washing of each well with 0.1×TBST, an HRP-conjugated anti-M13 antibody (Amersham Pharmacia Biotech) diluted with 0.1× TBST was added to each well, and the plate was incubated for 1 hour. After washing of each well with TBST, TMB single solution (Zymed Laboratories Inc.) was added to each well. The color reaction of the solution was further terminated by the addition of sulfuric acid. Then, the absorbance of each well was measured at 450 nm.

As a result of the phage ELISA, a clone was confirmed to specifically bind to the antigen when the coloring ratio of the antigen-coated plate to the antigen-uncoated plate was 2 or more times and the color developed by the antigen-coated plate was 0.2 or more. The clone confirmed to specifically bind to the antigen was further analyzed for the nucleotide sequence of the antibody fragment gene.

The results of the phage ELISA are shown in Table 2. In the table, R2 represents the results about clones after the completion of 2 rounds of panning, and R3 represents the results about clones after the completion of 3 rounds of panning. As a result, a plurality of clones specifically binding to hIL-6R and differing in sequence were obtained from each phage library.

TABLE 2

|  | NH-PAL | | NH-IAL | | NH-CEL | |
| --- | --- | --- | --- | --- | --- | --- |
|  | R2 | R3 | R2 | R3 | R2 | R3 |
| The number of evaluated clones | 96 | 96 | 96 | 96 | 96 | 96 |
| The number of antigen-specific clones | 0 | 10 | 43 | 87 | 5 | 13 |
| The type of sequence of antigen-specific clone | 0 | 1 | 23 | 25 | 3 | 4 |

Example 6

Evaluation of Antibody Capable of Binding to Human IL-6R Through Fixed L Chain for Ability to Bind Through IgG (6-1) Preparation of Human CD3e (hCD3e)

The extracellular region of human CD3e (hCD3e) was prepared as follows: hCD3e gene synthesized on the basis of the amino acid sequence of NCBI Reference Sequence NP 000724 (SEQ ID NO: 33) was altered to encode a protein lacking the presumed transmembrane region starting at valine at position 130 and subsequent regions and instead having an added FLAG tag sequence (SEQ ID NO: 13). An expression vector having an insert of the prepared gene encoding the altered hCD3e (SEQ ID NO: 34) was prepared.

The prepared expression vector was transferred to FreeStyle 293-F cells (Invitrogen Corp.) to transiently express hCD3e. The obtained culture supernatant was added to Q Sepharose FF column (GE Healthcare Japan Corp.) equilibrated with 20 mM Tris-HCl (pH 7.4), and the column was washed, followed by elution with the concentration gradient of sodium chloride. The fraction containing hCD3e was added to macro-Prep Ceramic Hydroxyapatite Type-I, 20 μm column (Bio-Rad Laboratories, Inc.) equilibrated with a 10 mM sodium phosphate buffer solution (pH 7.4), and the column was washed, followed by elution with the concentration gradient of a sodium phosphate buffer solution. The fraction containing hCD3e was concentrated through an ultrafiltration membrane. Then, the concentrate was added to Superdex 200 column (GE Healthcare Japan Corp.) equilibrated with D-PBS(−). Only the hCD3e fraction was recovered from the eluate to obtain purified hCD3e.

(6-2) Expression and Purification of Obtained Various Human IL-6R-Binding Antibodies Having Fixed L Chains Three antibodies 6RmIAB3(2)_02 (heavy chain: SEQ ID NO: 35; light chain: SEQ ID NO: 65), 6RmIAB3(2)_06 (heavy chain: SEQ ID NO: 36; light chain: SEQ ID NO: 65), and 6RmIAB3(2)_16 (heavy chain: SEQ ID NO: 37; light chain: SEQ ID NO: 65) among the antibodies obtained as human IL-6R-binding antibodies having the L chain of the anti-mouse IgA antibody mIANMIgL_095 in Example 5 were expressed using the method given below, and their culture supernatants were recovered. 0.4 mL of a human embryonic kidney cell-derived FreeStyle 293-F line (Invitrogen Corp.) suspended in FreeStyle 293 Expression Medium (Invitrogen Corp.) was inoculated at a cell density of $8.0 \times 10^5$ cells/mL to each well of a 96-well deep well plate. The prepared plasmids were transferred to the cells by the lipofection method. The cells were cultured for 4 days in a $CO_2$ incubator (37° C., 8% $CO_2$, 450 rpm).

One antibody 6RPAB3_03 (heavy chain: SEQ ID NO: 38; light chain: SEQ ID NO: 64) among the antibodies obtained as human IL-6R-binding antibodies having the L chain of the anti-plexin A1 antibody hPANKB2-3#135, and one antibody 6RhCEB3(2)_10 (heavy chain: SEQ ID NO: 39; light chain: SEQ ID NO: 66) among the antibodies obtained as human IL-6R-binding antibodies having the L chain of the humanized anti-CD3 antibody CE115 in Example 5 were expressed using the method given below, and these antibodies were purified. 3 mL of a human embryonic kidney cell-derived FreeStyle 293-F line (Invitrogen Corp.) suspended in FreeStyle 293 Expression Medium (Invitrogen Corp.) was inoculated at a cell density of $1.33×10^6$ cells/mL to each well of a 6-well plate. The prepared plasmids were transferred to the cells by the lipofection method. The cells were cultured for 4 days in a $CO_2$ incubator (37° C., 8% $CO_2$, 90 rpm). Each antibody was purified from the culture supernatant thus obtained by use of a method generally known to those skilled in the art using rProtein A Sepharose™ Fast Flow (Amersham Biosciences Corp.). The absorbance of the purified antibody solution was measured at 280 nm using a spectrophotometer. From the obtained measurement value, the antibody concentration was calculated by use of an extinction coefficient calculated by PACE (Protein Science (1995) 4, 2411-2423).

(6-3) Evaluation of Obtained Antibody Having Anti-Plexin A1 Antibody L Chain for Ability to Bind to Human IL-6R The antibody (6RPAB3_03) obtained in the paragraph (6-2) or an anti-plexin A1 antibody hPANKB2-3#135 (heavy chain: SEQ ID NO: 40; light chain: SEQ ID NO: 64) was evaluated for its binding activity against soluble human IL-6R and soluble human plexin A1 using Octet RED384 (forteBIO). The binding evaluation was conducted using HBS-EP+Buffer (GE Healthcare Japan Corp.) as a buffer.

Figure 7:
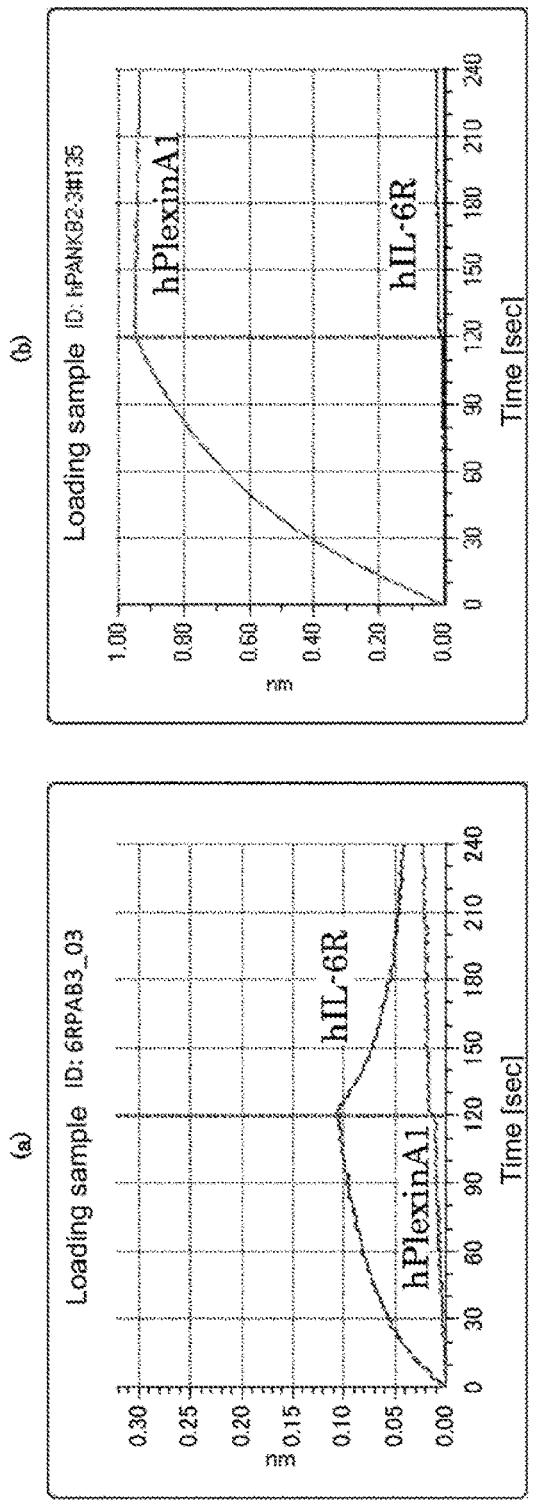
FIG. 7 is a diagram showing results of evaluating obtained antibodies 6RPAB3_03 (FIG. 7(a)) and anti-plexin A1 antibody hPANKB2-3#135 (FIG. 7(b)) for their binding activity against soluble human IL-6R and soluble human plexin A1 using Octet RED384 (forteBIO).

After binding of the antibody to Protein G Biosensors (forteBIO), soluble human IL-6R or soluble human plexin A1 was allowed to interact with the antibody on the biosensor through contact therebetween for 120 seconds, and subsequently contacted with the buffer for 120 seconds to measure the antibody-antigen interaction. Then, the biosensor was regenerated through contact with 10 mmol/L glycine-HCl (pH 1.5). The measurement was conducted at 30° C. The obtained sensorgram is shown in FIG. 7.

The 6RPAB3_03 antibody was found to bind to soluble human IL-6R without binding to soluble human plexin A1.

(6-4) Evaluation of Obtained Antibody Having Anti-Mouse IgA Antibody L Chain for Ability to Bind to Human IL-6R Each antibody (6RmIAB3(2)_02, 6RmIAB3(2)_06, and 6RmIAB3(2)_16) obtained in the paragraph (6-2) or an anti-mouse IgA antibody mIANMIgL_095 (heavy chain: SEQ ID NO: 41; light chain: SEQ ID NO: 65) was evaluated for its binding activity against soluble human IL-6R and mouse IgA using Octet RED384 (forteBIO). The binding evaluation was conducted using HBS-EP+Buffer (GE Healthcare Japan Corp.) as a buffer.

Figure 8:
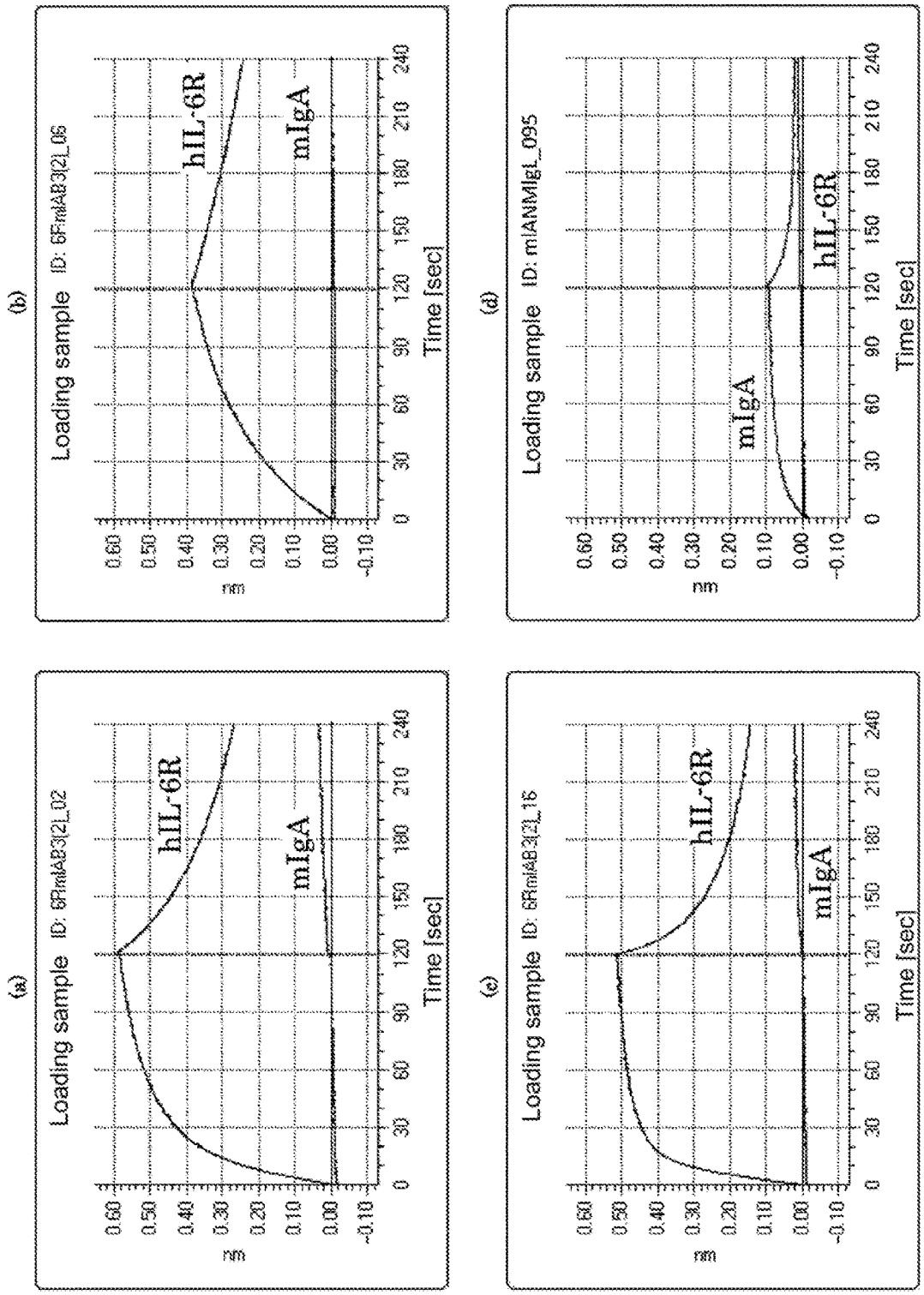
FIG. 8 is a diagram showing results of evaluating obtained antibodies 6RmIAB3(2)_02 (FIG. 8(a)), 6RmIAB3(2)_06 (FIG. 8(b)), 6RmIAB3(2)_16 (FIG. 8(c)), and anti-mouse IgA antibody mIANMIgL_095 (FIG. 8(d)) for their binding activity against soluble human IL-6R and mouse IgA using Octet RED384 (forteBIO).

After binding of the antibody to Protein G Biosensors (forteBIO), soluble human IL-6R or mouse IgA was allowed to interact with the antibody on the biosensor through contact therebetween for 120 seconds, and subsequently contacted with the buffer for 120 seconds to measure the antibody-antigen interaction. Then, the biosensor was regenerated through contact with 10 mmol/L glycine-HCl (pH 1.5). The measurement was conducted at 30° C. The obtained sensorgram is shown in FIG. 8.

All of the antibodies 6RmIAB3(2)_02, 6RmIAB3(2)_06, and 6RmIAB3(2)_16 were found to bind to soluble human IL-6R without binding to mouse IgA.

(6-5) Evaluation of Obtained Antibody Having Anti-CD3 Antibody L Chain for Ability to Bind to Human IL-6R The antibody (6RhCEB3(2)_10) obtained in the paragraph (6-2) or an anti-CD3 antibody hCE115HA/L0000 (heavy chain: SEQ ID NO: 42; light chain: SEQ ID NO: 66) was evaluated for its binding activity against soluble human IL-6R and human CD3e (hCD3e) using Octet RED384 (forteBIO). The binding evaluation was conducted using HBS-EP+Buffer (GE Healthcare Japan Corp.) as a buffer.

Figure 9:
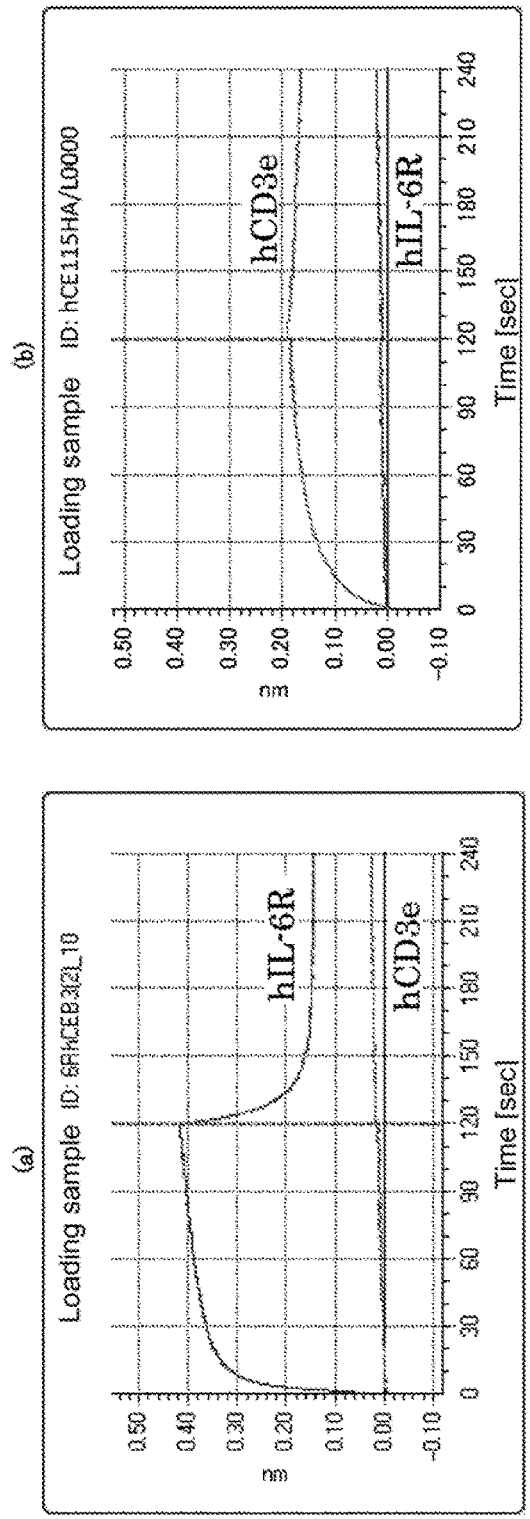
FIG. 9 is a diagram showing results of evaluating obtained antibodies 6RhCEB3(2)_10 (FIG. 9(a)) and anti-CD3 antibody hCE115HA/L0000 (FIG. 9(b)) for their binding activity against soluble human IL-6R and human CD3e using Octet RED384 (forteBIO).

After binding of the antibody to Protein G Biosensors (forteBIO), soluble human IL-6R or human CD3e was allowed to interact with the antibody on the biosensor through contact therebetween for 120 seconds, and subsequently contacted with the buffer for 120 seconds to measure the antibody-antigen interaction. Then, the biosensor was regenerated through contact with 10 mmol/L glycine-HCl (pH 1.5). The measurement was conducted at 30° C. The obtained sensorgram is shown in FIG. 9.

The 6RhCEB3(2)_10 antibody was found to bind to soluble human IL-6R without binding to human CD3e.

Example 7

Establishment of Method for Producing Fab-Displaying Phage by Combination of L Chain-Expressing Phagemid Vector and H Chain-Expressing Helper Phage (7-1) Construction of H Chain-Expressing Helper Phage Carrying H Chain-Gene 3 Fusion Product Expression Unit A promoter, a signal sequence gene, an antibody H chain gene, phage gene 3 etc., were incorporated to the genome of a helper phage to construct an H chain (Fd consisting of VH and CH1)-gene 3-expressing helper phage. The antibody H chain (Fd consisting of VH and CH1)-gene 3 can be expressed from *E. coli* infected with this helper phage.

Specifically, an *E. coli* strain ER2738 was infected with the helper phage M13KO7TC and shake-cultured overnight, followed by the genome extraction of the helper phage M13KO7TC from the infected *E. coli* (NucleoBond Xtra Midi Plus). A SacI site positioned between a kanamycin resistance gene (KanR) and p15A ori was selected as the site to which the H chain-gene 3 expression unit was inserted (FIG. 1). The insertion site is not limited to this site and may be, for example, a SacII site positioned between p15A ori and M13 ori without problems. The genome of the helper phage M13KO7TC purified by the aforementioned method was cleaved with SacI, then electrophoresed on 0.6% agarose gel, and purified by gel extraction (Wizard SV Gel and PCR Clean-Up system; Promega Corp.) to obtain the DNA fragment (M13KO7TC/SacI) of interest.

The H chain of an anti-human IL-6R antibody PF1 was used as the antibody H chain (Fd consisting of VH and CH1) to be introduced. The amino acid sequence of the PF1 H chain is shown in SEQ ID NO: 8, and the nucleotide sequence encoding it is shown in SEQ ID NO: 43. The antibody H chain (Fd consisting of VH and CH1) was fused with the gene 3 protein (g3p) via the linker peptide. araC repressor—araBAD altered promoter—malE signal sequence gene—PF1 H chain gene—gene 3 was inserted to M13KO7TC/SacI by the in-fusion method (In-Fusion HD Cloning Kit; Clontech Laboratories, Inc.), which was then transferred to an *E. coli* strain ER2738 by the electroporation method. The nucleic acid sequence of the araC repressor is shown in SEQ ID NO: 44. The nucleic acid sequence of the araBAD altered promoter is shown in SEQ ID NO: 45. The amino acid sequence of the malE signal sequence and the nucleic acid sequence encoding it are shown in SEQ ID NO: 46 and SEQ ID NO: 47, respectively. The gene 3 used had a nucleic acid sequence (SEQ ID NO: 48) different from that of the gene 3 present in the helper phage.

The obtained *E. coli* was cultured. 2.5 M NaCl/10% PEG was added to the culture supernatant, and the helper phage was purified by the PEG precipitation method. The titer of the obtained helper phage M13KO7AG-PF1H was confirmed by the general plaque formation method.

(7-2) Construction of L Chain-Expressing Phagemid Vector

A phagemid vector for expressing an antibody L chain was constructed. The phagemid vector was prepared by functionally inserting a packaging signal gene for phage particles, a promoter, a signal sequence gene, an antibody L chain gene, etc., to a plasmid vector. In this respect, the substitution of the C-terminal Cys of the L chain constant region by Ala is known to be advantageous for Fab expression in *E. coli* (J Biol Chem. 2003 Oct. 3; 278 (40): 38194-38205). Therefore, such a sequence was used. The constructed phagemid vector was transferred to an *E. coli* strain ER2738 by the electroporation method to construct *E. coli* ER2738/pL-PF1L carrying the PF1 L chain-expressing phagemid vector.

(7-3) Production of Fab-Displaying Phage by Combination of L Chain-Expressing Phagemid Vector and H Chain-Expressing Helper Phage The *E. coli* ER2738/pL-PF1L was cultured until OD reached around 0.5, and then infected with the helper phage M13KO7TC-PF1H or M13KO7TC. After medium replacement with a medium containing 25 μM (micro M) IPTG and 0.2% arabinose, the *E. coli* was cultured overnight at 30° C., and the culture supernatant was recovered. 2.5 M NaCl/10% PEG was added to the *E. coli* culture supernatant solution containing the produced phage to precipitate the phage, which was then dissolved in TBS to obtain a phage solution. The titer of the obtained phage was confirmed by the general colony formation method.

(7-4) Confirmation of Fab Display on Phage by Phage ELISA Method

The phage ELISA method was carried out to confirm Fab display on the produced phage and to confirm the ability to bind to the antigen. StreptaWell 96-well microtiter plate (F. Hoffmann-La Roche, Ltd.) was coated by the addition of 100 μL of PBS containing Goat anti-Human Kappa Biotin antibody (EY Laboratories, Inc.) or biotinylated human IL-6R. Each well of the plate was washed with 0.1×TBST (0.1× TBS containing 0.1% Tween 20) to remove the antigen. Then, the plate was blocked for 1 hour or longer by the addition of 250 μL of 0.02% skim milk-0.1×TBS (0.1×TBS containing 0.02% skim milk) to the well. After removal of the 0.02% skim milk-0.1×TBS, the phage solution diluted with 0.02% skim milk-0.1×TBS was added to each well, and the plate was left standing for 1 hour so that the antibody displayed on the phage bound to the Goat anti-Human Kappa Biotin antibody or the biotinylated human IL-6R. After washing with 0.1×TBST, an HRP-conjugated anti-M13 antibody (Amersham Pharmacia Biotech) diluted with 0.1×TBST was added to each well, and the plate was incubated for 1 hour. After washing with 0.1×TBST, TMB single solution (Zymed Laboratories Inc.) was added to each well. The color reaction of the solution was further terminated by the addition of sulfuric acid. Then, the absorbance was measured at 450 nm.

Figure 10:
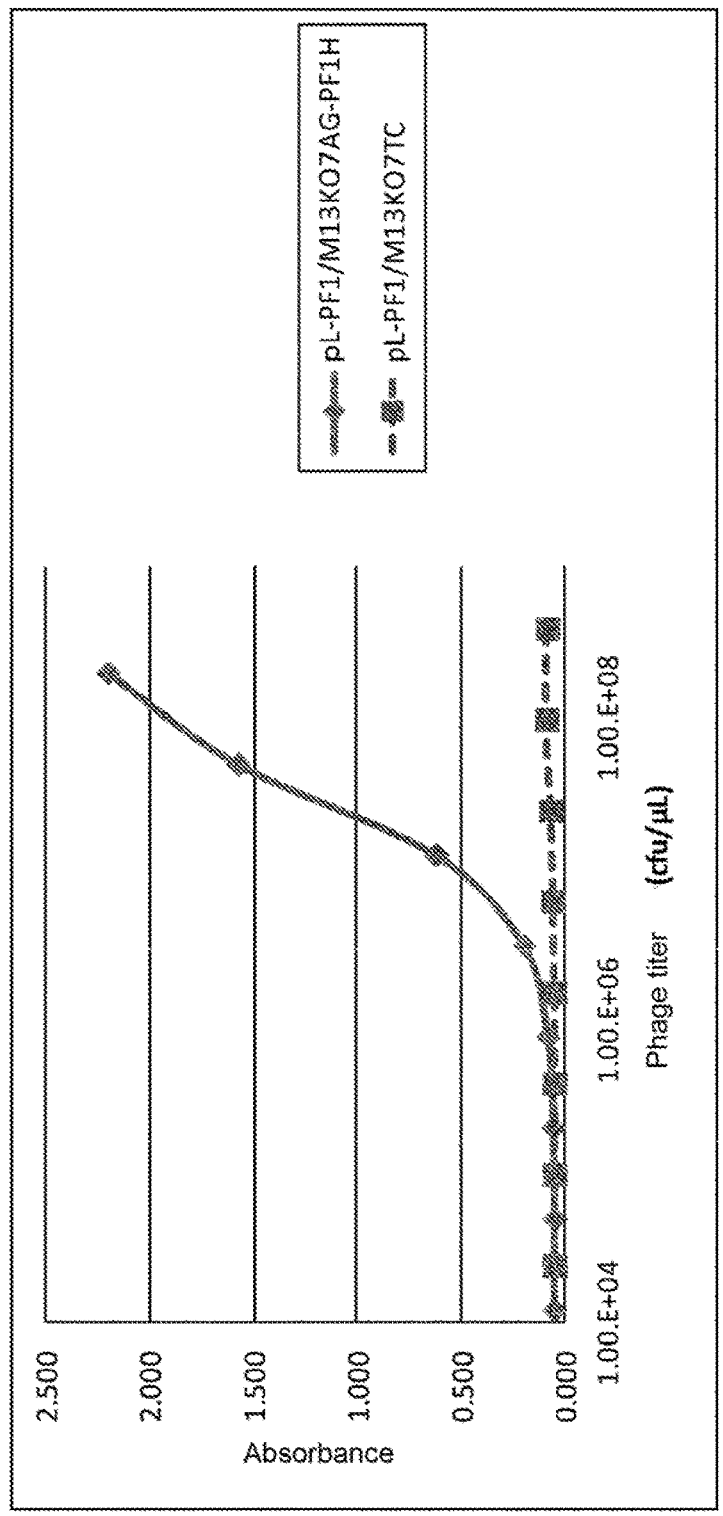
FIG. 10 is a diagram showing results of conducting ELISA using an anti-human κ chain antibody for a phage produced by a combination of an L chain (PF1L)-expressing phagemid vector and an H chain (PF1H)-expressing helper phage. In the case of using the H chain-expressing helper phage (M13KO7AG-PF1H), Fab was confirmed to be displayed on the phage. On the other hand, in the case of using a negative control helper phage (M13KO7TC), no Fab was confirmed to be displayed on the phage.
Figure 11:
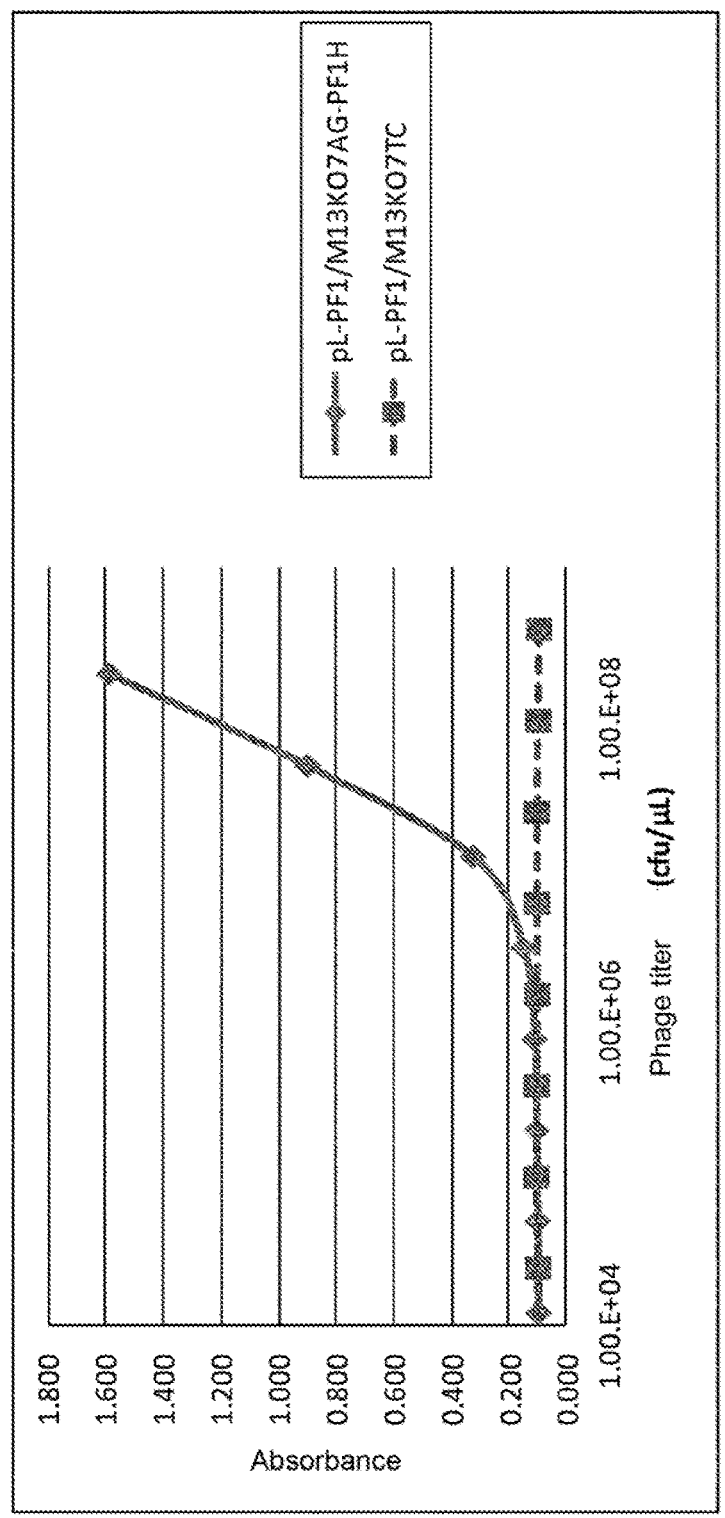
FIG. 11 is a diagram showing results of conducting ELISA using human IL-6R as an antigen for a phage produced by a combination of an L chain (PF1L)-expressing phagemid vector and an H chain (PF1H)-expressing helper phage. In the case of using the H chain-expressing helper phage (M13KO7AG-PF1H), the Fab-displaying phage was confirmed to have the ability to bind to the antigen. On the other hand, in the case of using a negative control helper phage (M13KO7TC), its binding to the antigen was not observed.

As a result, it was confirmed that: Fab was displayed on the phage only when the phage was produced by the combination of the L chain-expressing phagemid vector and the H chain-expressing helper phage M13KO7AG-PF1H (FIG. 10); and Fab displayed on the phage maintained the ability to bind to the antigen (FIG. 11).

Example 8

Construction of Phagemid Library Comprising Naive L Chains and Production of Fab Phage Library Comprising Naive L Chains and Anti-Plexin A1 Antibody H Chains (8-1) Construction of Phagemid Library Comprising Naive L Chains Naive L chain genes were amplified by PCR using poly-A RNA prepared from human peripheral blood mononuclear cells (PBMCs), commercially available human poly-A RNA, or the like as a template. These genes were inserted to phagemid vectors, and the constructed phagemid vectors were transferred to an *E. coli* strain ER2738 by the electroporation method. Consequently, approximately $6.5 \times 10^6$ colonies were obtained.

(8-2) Production of Fab Phage Library Comprising Naive L Chains and Anti-Plexin A1 Antibody H Chains Helper phages (M13KO7AG-hPNL264H, M13KO7AG-hPNL342H, and M13KO7AG-hPNL359H) expressing the H chain (SEQ ID NO: 49) of an anti-plexin A1 antibody hPANLB2-3_264, the H chain (SEQ ID NO: 50) of an anti-plexin A1 antibody hPANLB2-3_342, and the H chain (SEQ ID NO: 51) of an anti-plexin A1 antibody hPANLB2-3_359, respectively, were each constructed by the method described in Example 7.

The *E. coli* harboring the phagemid library comprising naive L chains described in the paragraph (8-1) was infected with each helper phage (M13KO7AG-hPNL264H, M13KO7AG-hPNL342H, and M13KO7AG-hPNL359H) described above to construct human antibody phage display libraries (264H-NL library, 342H-NL library, and 359H-NL library) displaying Fabs comprising naive L chains and their respective anti-plexin A1 antibody H chains. 2.5 M NaCl/10% PEG was added to the *E. coli* culture solutions containing the produced phages to precipitate the phages, which were then diluted with TBS to obtain phage library solutions.

Example 9

Obtainment of Fab Having Enhanced Ability of Anti-Plexin A1 Antibody to Bind to Antigen (9-1) Obtainment of Antibody Fragment Strongly Binding to Human Plexin A1 Using Fixed H Chain Antibody Library The phage library solution of each fixed H chain antibody library (264H-NL library, 342H-NL library, and 359H-NL library) constructed in Example 8 was screened for antibody fragments binding to human plexin A1 with the ability to bind to human plexin A1 as an index.

Each phage library solution was blocked by the addition of BSA (final concentration: 4%) to the phage library solution. The panning method was used with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2), 212-220; and Mol. Cell Proteomics (2003) 2 (2), 61-69). The magnetic beads used were NeutrAvidin coated beads (Sera-Mag SpeedBeads NeutrAvidin-coated) or Streptavidin coated beads (Dynabeads M-280 Streptavidin). Specifically, the biotinylated antigen (biotinylated hPlexin A1) was added to the prepared phage library solution, and the antigen was contacted with the phage library solution at room temperature for 60 minutes. The biotinylated antigen was used at 10 pmol for the first panning and 1 pmol for the second or later panning. Then, an unlabeled antigen (soluble human plexin A1) was added in an amount of 100 times the amount of the biotinylated antigen used, and allowed to compete therewith for 10 minutes. The magnetic beads blocked with a BSA solution were added thereto, and the magnetic beads were allowed to bind to the antigen-phage complexes at room temperature for 15 minutes. The recovered beads were washed with 1 mL of TBST (TBS containing 0.1% Tween 20) and 1 mL of TBS. Then, 0.5 mL of a 1 mg/mL trypsin solution was added to the beads. Immediately after suspension at room temperature for 15 minutes, the beads were separated using a magnetic stand to recover the phage solution in the supernatant. The recovered phage solution was added to 10 mL of an *E. coli* strain ER2738 cultured until the logarithmic growth phase (OD600=0.4-0.7). The *E. coli* was cultured by mild stirring at 37° C. for 1 hour and thereby infected with the phage. The infected *E. coli* was inoculated to a 225 mm×225 mm plate. Next, the inoculated *E. coli* was recovered and cultured. Then, the *E. coli* was infected with each helper phage carrying the anti-plexin A1 antibody H chain gene constructed in the paragraph (8-2), and cultured to produce phages displaying Fabs comprising various anti-plexin A1 antibody H chains. The phages were recovered from the culture solution to prepare a phage library solution. This operation was defined as one round of panning, and a total of 4 rounds of panning was repetitively carried out.

(9-2) Screening for Antibody Binding to Antigen (Human Plexin A1) by Phage ELISA Method Phage production was performed according to a standard method (Methods Mol. Biol. (2002) 178, 133-145) from the *E. coli* single colony obtained after the completion of the 2, 3, or 4 rounds of panning carried out in the paragraph (9-1). A phage-containing culture supernatant was recovered. In this operation, M13KO7AG-hPNL264H, M13KO7AG-hPNL342H, or M13KO7AG-hPNL359H was used as a helper phage according to the phage library used. The culture supernatant was subjected to ELISA by the following procedures.

StreptaWell 96-well microtiter plate (F. Hoffmann-La Roche, Ltd.) was coated overnight with 100 µL of PBS containing or not containing the biotinylated antigen (biotinylated hPlexin A1). Each well of the plate was washed with 0.1×TBST (0.1×TBS containing 0.1% Tween 20) to remove the antigen. Then, each well was blocked for 1 hour or longer with 250 µL of 0.02% skim milk-0.1×TBS (0.1×TBS containing 0.02% skim milk). After removal of the 0.02% skim milk-0.1×TBS, the phage culture supernatant was added to each well, and the plate was left standing for 1 hour so that the antibody displayed on the phage bound to the biotinylated antigen present in each well. After washing of each well with 0.1×TBST, an HRP-conjugated anti-M13 antibody (Amersham Pharmacia Biotech) diluted with 0.1× TBST was added to each well, and the plate was incubated for 1 hour. After washing of each well with TBST, TMB single solution (Zymed Laboratories Inc.) was added to each well. The color reaction of the solution was further terminated by the addition of sulfuric acid. Then, the absorbance of each well was measured at 450 nm.

As a result of the phage ELISA, a clone was confirmed to specifically bind to the antigen when the coloring ratio of the antigen-coated plate to the antigen-uncoated plate was 2 or more times and the color developed by the antigen-coated plate was 0.2 or more. The clone confirmed to specifically bind to the antigen was further analyzed for the nucleotide sequence of the antibody fragment gene.

The results of the phage ELISA are shown in Table 3. In the table, R2 represents the results about clones after the completion of 2 rounds of panning; R3 represents the results about clones after the completion of 3 rounds of panning; and R4 represents the results about clones after the completion of 4 rounds of panning. As a result, a plurality of clones specifically binding to hPlexin A1 and differing in sequence were obtained from each phage library (264H-NL library, 342H-NL library, and 359H-NL library).

TABLE 3

|  | 264H-NL library | | | 342H-NL library | | | 359H-NL library | | |
| --- | --- | --- | --- | --- | --- | --- | --- | --- | --- |
|  | R2 | R3 | R4 | R2 | R3 | R4 | R2 | R3 | R4 |
| The number of evaluated clones | 96 | 96 | 96 | 96 | 96 | 96 | 96 | 96 | 96 |
| The number of antigen-specific clones | 5 | 25 | 94 | 38 | 68 | 92 | 74 | 65 | 93 |
| The type of sequence of antigen-specific clone | 3 | 18 | 86 | 36 | 66 | 71 | 66 | 57 | 71 |

Example 10

Evaluation of Affinity Maturation Product of Anti-Plexin A1 Antibody for Ability to Bind Through IgG (10-1) Expression and Purification of Obtained Human Plexin A1-Binding Antibody Three antibodies PLR2H264#002 (heavy chain: SEQ ID NO: 58; light chain: SEQ ID NO: 52), PLR4H264#061 (heavy chain: SEQ ID NO: 58; light chain: SEQ ID NO: 53), and PLR3H264#022 (heavy chain: SEQ ID NO: 58; light chain: SEQ ID NO: 54) among the antibodies obtained as antibodies binding to human plexin A1 from the 264H-NL library, one antibody PLR2H342#009 (heavy chain: SEQ ID NO: 59; light chain: SEQ ID NO: 55) among the antibodies obtained as antibodies binding to human plexin A1 from the 342H-NL library, and two antibodies PLR2H359#087 (heavy chain: SEQ ID NO: 60; light chain: SEQ ID NO: 56) and PLR2H359#062 (heavy chain: SEQ ID NO: 60; light chain: SEQ ID NO: 57) among the antibodies obtained as antibodies binding to human plexin A1 from the 359H-NL library in Example 9 were expressed using the method given below, and these antibodies were purified. The parent antibodies hPANLB2-3_264 (heavy chain: SEQ ID NO: 58, light chain: SEQ ID NO: 61), hPANLB2-3_342 (heavy chain: SEQ ID NO: 59, light chain: SEQ ID NO: 62), and hPANLB2-3_359 (heavy chain: SEQ ID NO: 60, light chain: SEQ ID NO: 63) were also expressed as controls by the method given below, and these antibodies were purified. 3 mL of a human embryonic kidney cell-derived FreeStyle 293-F line (Invitrogen Corp.) suspended in FreeStyle 293 Expression Medium (Invitrogen Corp.) was inoculated at a cell density of 1.33×10⁶ cells/mL to each well of a 6-well plate. The prepared plasmids were transferred to the cells by the lipofection method. The cells were cultured for 4 days in a $CO_2$ incubator (37° C., 8% $CO_2$, 90 rpm). Each antibody was purified from the culture supernatant thus obtained by use of a method generally known to those skilled in the art using rProtein A Sepharose™ Fast Flow (Amersham Biosciences Corp.). The absorbance of the purified antibody solution was measured at 280 nm using a spectrophotometer. From the obtained measurement value, the antibody concentration was calculated by use of an extinction coefficient calculated by PACE (Protein Science (1995) 4, 2411-2423).

(10-2) Evaluation of Obtained Anti-Plexin A1 Antibody for Ability to Bind

Each antibody obtained in the paragraph (10-1) was evaluated for its binding activity against the antigen by surface plasmon resonance (SPR) analysis.

In the SPR analysis, the antibody was analyzed using Biacore T200 (GE Healthcare Japan Corp.). The anti-human plexin A1 antibody was immobilized onto the surface of Sensor Chip CM4 using Recombinant Protein A/G (Thermo Fisher Scientific Inc.) and Amine Coupling Kit (GE Healthcare Japan Corp.). The antigen used was a human plexin A1 protein sema domain (from glutamic acid at position 28 to serine at position 514) tagged at the C terminus of the protein with FLAG tag. The antigen was prepared as follows: an expression vector carrying a cDNA corresponding to the human plexin A1 sema domain was transferred to FreeStyle 293 cells. After culture, the obtained culture solution was passed through an anti-FLAG-M2 antibody-immobilized affinity column. A fraction eluted with the FALG peptide was purified by gel filtration. The obtained antigen was serially diluted with 20 mM ACES, 150 mM NaCl, 0.05% polysorbate 20, and 1.2 mM $CaCl_2$ (pH 7.4) and added to the sensor chip at a flow rate of 30 μL/min. In this assay system, the dissociation constant (KD) between the human plexin A1 protein and the anti-human plexin A1 antibody was calculated using data analysis software (BIA T200 Evaluation software ver. 2). The results are shown in Table 4.

Antibodies having the enhanced ability to bind were successfully obtained, as compared with the antibodies before the L chain reselection.

In another way to utilize this method, even an antibody whose ability to bind has not been enhanced can be used in the humanization of a non-human animal-derived antibody (J Mol Biol. 2000 Feb. 25; 296 (3): 833-49). Human-derived antibody L chains can be obtained by panning operation for an antigen using fixed H chains of the non-human animal-derived antibody and a human naive-derived L chain antibody library in combination. Subsequently, a human-derived antibody H chain can be obtained by panning operation for the antigen using the fixed L chains and a human naive-derived H chain antibody library in combination. Those skilled in the art would understand that, in this way, a human antibody can be obtained on the basis of the non-human animal-derived antibody by the sequential replacement with the human antibody libraries.

TABLE 4

| Sample Name | KD (M) | Relative KD improvement |
| --- | --- | --- |
| hPANLB2-3_264 | 1.73E−07 | 1.0 (control) |
| PLR2H264#002 | 1.38E−07 | 1.3 |
| PLR4H264#061 | 4.10E−08 | 4.2 |
| PLR3H264#022 | 5.69E−08 | 3.0 |
| hPANLB2-3_342 | 3.45E−08 | 1.0 (control) |
| PLR2H342#009 | 1.82E−09 | 19.0 |
| hPANLB2-3_359 | 1.35E−08 | 1.0 (control) |
| PLR2H359#087 | 4.62E−09 | 2.9 |
| PLR2H359#062 | 3.93E−09 | 3.4 |

In Table 4, Relative KD improvement represents a value showing how many times the ability to bind was enhanced in terms of KD as compared with the parent antibody. The antibodies having the enhanced affinity relative to their parent antibodies were obtained.

INDUSTRIAL APPLICABILITY

In one aspect, the present invention provides a method for efficiently preparing a plurality of antigen-binding molecules comprising common first polypeptides.

The conventional phage display technology may also prepare an antigen-binding molecule display library having fixed sequences of first polypeptides. However, it is very difficult to change later the sequences of the first polypeptides in a temporarily prepared library because a library of bacteria each capable of expressing both of the first polypeptide and a second polypeptide at the same time is prepared. In addition, it is very difficult to prepare a plurality of libraries having fixed sequences of the first polypeptides because the conventional preparation of the antigen-binding molecule display library usually requires enormous time and energy.

On the other hand, in the present invention, once a library of bacteria capable of expressing second polypeptides is prepared, an antigen-binding molecule display library having fixed sequences of first polypeptides can be conveniently prepared one after another by changing only the first polypeptides contained in helper phages. Therefore, operational efficiency can be drastically increased. The present invention is very useful as novel phage display technology. One example of the application of the present invention can include the development of a multispecific antibody comprising common L chains or H chains.

SEQUENCE LISTING

<160> NUMBER OF SEQ ID NOS: 68

<210> SEQ ID NO 1
<211> LENGTH: 423
<212> TYPE: PRT
<213> ORGANISM: Enterobacteria phage M13

<400> SEQUENCE: 1

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

```
Asn Ser Phe Thr Asn Val Trp Lys Asp Asp Lys Thr Leu Asp Arg Tyr
         35                  40                  45

Ala Asn Tyr Glu Gly Cys Leu Trp Asn Ala Thr Gly Val Val Val Cys
 50                  55                  60

Thr Gly Asp Glu Thr Gln Cys Tyr Gly Thr Trp Val Pro Ile Gly Leu
 65                  70                  75                  80

Ala Ile Pro Glu Asn Glu Gly Gly Ser Glu Gly Gly Ser Glu
                 85                  90                  95

Gly Gly Gly Ser Glu Gly Gly Thr Lys Pro Pro Glu Tyr Gly Asp
                100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
        130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Ser Glu Gly Gly Gly
                245                 250                 255

Ser Glu Gly Gly Gly Ser Gly Gly Ser Gly Gly Ser Gly
                260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
        355                 360                 365

Ser Val Glu Cys Arg Pro Phe Val Phe Gly Ala Gly Lys Pro Tyr Glu
370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu
            420

<210> SEQ ID NO 2
<211> LENGTH: 419
<212> TYPE: PRT
```

<213> ORGANISM: Artificial Sequence
<220> FEATURE:
<223> OTHER INFORMATION: modified sequence of gene 3 of Enterobacteria phage M13

<400> SEQUENCE: 2

```
Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Ser Glu
                85                  90                  95

Gly Gly Gly Ser Glu Gly Gly Gly Thr Lys Pro Pro Glu Tyr Gly Asp
                100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Val Asn Ala Gly Gly Gly Pro Ala
225                 230                 235                 240

Gly Leu Ser Glu Gly Ser Thr Ile Glu Gly Arg Gly Ala His Glu Gly
                245                 250                 255

Gly Gly Val Pro Gly Ser Gly Gly Ser Gly Ser Gly Asp Phe Asp
            260                 265                 270

Tyr Glu Lys Met Ala Asn Ala Asn Lys Gly Ala Met Thr Glu Asn Ala
        275                 280                 285

Asp Glu Asn Ala Leu Gln Ser Asp Ala Lys Gly Lys Leu Asp Ser Val
    290                 295                 300

Ala Thr Asp Tyr Gly Ala Ala Ile Asp Gly Phe Ile Gly Asp Val Ser
305                 310                 315                 320

Gly Leu Ala Asn Gly Asn Gly Ala Thr Gly Asp Phe Ala Gly Ser Asn
                325                 330                 335

Ser Gln Met Ala Gln Val Gly Asp Gly Asp Asn Ser Pro Leu Met Asn
            340                 345                 350

Asn Phe Arg Gln Tyr Leu Pro Ser Leu Pro Gln Ser Val Glu Cys Arg
        355                 360                 365

Pro Phe Val Phe Gly Ala Gly Lys Pro Tyr Glu Phe Ser Ile Asp Cys
370                 375                 380
```

```
Asp Lys Ile Asn Leu Phe Arg Gly Val Phe Ala Phe Leu Leu Tyr Val
385                 390                 395                 400

Ala Thr Phe Met Tyr Val Phe Ser Thr Phe Ala Asn Ile Leu Arg Asn
                405                 410                 415

Lys Glu Ser

<210> SEQ ID NO 3
<211> LENGTH: 122
<212> TYPE: DNA
<213> ORGANISM: Escherichia coli

<400> SEQUENCE: 3
gcgcaacgca attaatgtga gttagctcac tcattaggca ccccaggctt tacactttat      60
gcttccggct cgtatgttgt gtggaattgt gagcggataa caatttcaca caggaaacag     120
ct                                                                   122

<210> SEQ ID NO 4
<211> LENGTH: 22
<212> TYPE: PRT
<213> ORGANISM: Escherichia coli

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 5
<211> LENGTH: 66
<212> TYPE: DNA
<213> ORGANISM: Escherichia coli

<400> SEQUENCE: 5
atgaaatacc tattgcctac ggcagccgct ggattgttat tactcgcggc ccagccggcc      60
atggcg                                                                66

<210> SEQ ID NO 6
<211> LENGTH: 214
<212> TYPE: PRT
<213> ORGANISM: Artificial Sequence
<220> FEATURE:
<223> OTHER INFORMATION: amino acid sequence of PF1 light chain;
      sequence in which Cys at the C-terminus of the light chain
      constant region in SEQ ID NO:67 is substituted with Ala

<400> SEQUENCE: 6

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
                20                  25                  30

Leu Asn Trp Tyr Gln Gln Lys Pro Gly Lys Ala Pro Glu Leu Leu Ile
            35                  40                  45

Tyr Tyr Gly Ser Glu Leu His Ser Gly Val Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
```

```
            100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
        210

<210> SEQ ID NO 7
<211> LENGTH: 648
<212> TYPE: DNA
<213> ORGANISM: Artificial Sequence
<220> FEATURE:
<223> OTHER INFORMATION: nucleic acid sequence of PF1 light chain of SEQ
      ID NO:6

<400> SEQUENCE: 7
gacatccaga tgacccagag cccaagcagc ctgagcgcca gcgtgggtga cagcgtgacc      60
atcacctgtc aagccagcca ggacatcagc agttacctga attggtacca gcagaagcca     120
ggaaaggctc cagagctgct gatctactac ggctccgaac tgcactctgg tgtgccaagc     180
agattcagcg gtagcggtag cggtaccgac ttcaccttca ccatcagcag cctcgaggca     240
gaggacgccg ctacctacta ctgcgggcag ggtaaccggc ttccatacac gttcggccaa     300
gggaccaagg tggaaatcga acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcgt gcgaagtcac ccatcagggc     600
ctgagctcgc ccgtcacaaa gagcttcaac aggggagagg cttgataa                  648

<210> SEQ ID NO 8
<211> LENGTH: 216
<212> TYPE: PRT
<213> ORGANISM: Artificial Sequence
<220> FEATURE:
<223> OTHER INFORMATION: amino acid sequence of PF1 heavy chain (Fd)

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
```

```
                65                  70                  75                  80
Leu Lys Leu Ser Ser Val Thr Ala Ala Asp Thr Ala Ala Tyr Tyr Cys
                    85                  90                  95

Ala Arg Val Leu Ala Arg Ile Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys
            210                 215

<210> SEQ ID NO 9
<211> LENGTH: 1896
<212> TYPE: PRT
<213> ORGANISM: Homo sapiens

<400> SEQUENCE: 9

Met Pro Leu Pro Pro Arg Ser Leu Gln Val Leu Leu Leu Leu Leu Leu
1               5                   10                  15

Leu Leu Leu Leu Leu Pro Gly Met Trp Ala Glu Ala Gly Leu Pro Arg
                20                  25                  30

Ala Gly Gly Gly Ser Gln Pro Pro Phe Arg Thr Phe Ser Ala Ser Asp
            35                  40                  45

Trp Gly Leu Thr His Leu Val His Glu Gln Thr Gly Glu Val Tyr
50                  55                  60

Val Gly Ala Val Asn Arg Ile Tyr Lys Leu Ser Gly Asn Leu Thr Leu
65                  70                  75                  80

Leu Arg Ala His Val Thr Gly Pro Val Glu Asp Asn Glu Lys Cys Tyr
                85                  90                  95

Pro Pro Pro Ser Val Gln Ser Cys Pro His Gly Leu Gly Ser Thr Asp
                100                 105                 110

Asn Val Asn Lys Leu Leu Leu Asp Tyr Ala Ala Asn Arg Leu Leu
            115                 120                 125

Ala Cys Gly Ser Ala Ser Gln Gly Ile Cys Gln Phe Leu Arg Leu Asp
            130                 135                 140

Asp Leu Phe Lys Leu Gly Glu Pro His His Arg Lys Glu His Tyr Leu
145                 150                 155                 160

Ser Ser Val Gln Glu Ala Gly Ser Met Ala Gly Val Leu Ile Ala Gly
                165                 170                 175

Pro Pro Gly Gln Gly Gln Ala Lys Leu Phe Val Gly Thr Pro Ile Asp
            180                 185                 190

Gly Lys Ser Glu Tyr Phe Pro Thr Leu Ser Ser Arg Arg Leu Met Ala
            195                 200                 205

Asn Glu Glu Asp Ala Asp Met Phe Gly Phe Val Tyr Gln Asp Glu Phe
            210                 215                 220
```

```
Val Ser Ser Gln Leu Lys Ile Pro Ser Asp Thr Leu Ser Lys Phe Pro
225                 230                 235                 240

Ala Phe Asp Ile Tyr Tyr Val Tyr Ser Phe Arg Ser Glu Gln Phe Val
                245                 250                 255

Tyr Tyr Leu Thr Leu Gln Leu Asp Thr Gln Leu Thr Ser Pro Asp Ala
            260                 265                 270

Ala Gly Glu His Phe Phe Thr Ser Lys Ile Val Arg Leu Cys Val Asp
        275                 280                 285

Asp Pro Lys Phe Tyr Ser Tyr Val Glu Phe Pro Ile Gly Cys Glu Gln
    290                 295                 300

Ala Gly Val Glu Tyr Arg Leu Val Gln Asp Ala Tyr Leu Ser Arg Pro
305                 310                 315                 320

Gly Arg Ala Leu Ala His Gln Leu Gly Leu Ala Glu Asp Glu Asp Val
                325                 330                 335

Leu Phe Thr Val Phe Ala Gln Gly Gln Lys Asn Arg Val Lys Pro Pro
            340                 345                 350

Lys Glu Ser Ala Leu Cys Leu Phe Thr Leu Arg Ala Ile Lys Glu Lys
        355                 360                 365

Ile Lys Glu Arg Ile Gln Ser Cys Tyr Arg Gly Glu Gly Lys Leu Ser
    370                 375                 380

Leu Pro Trp Leu Leu Asn Lys Glu Leu Gly Cys Ile Asn Ser Pro Leu
385                 390                 395                 400

Gln Ile Asp Asp Phe Cys Gly Gln Asp Phe Asn Gln Pro Leu Gly
                405                 410                 415

Gly Thr Val Thr Ile Glu Gly Thr Pro Leu Phe Val Asp Lys Asp Asp
            420                 425                 430

Gly Leu Thr Ala Val Ala Ala Tyr Asp Tyr Arg Gly Arg Thr Val Val
        435                 440                 445

Phe Ala Gly Thr Arg Ser Gly Arg Ile Arg Lys Ile Leu Val Asp Leu
    450                 455                 460

Ser Asn Pro Gly Gly Arg Pro Ala Leu Ala Tyr Glu Ser Val Val Ala
465                 470                 475                 480

Gln Glu Gly Ser Pro Ile Leu Arg Asp Leu Val Leu Ser Pro Asn His
                485                 490                 495

Gln Tyr Leu Tyr Ala Met Thr Glu Lys Gln Val Thr Arg Val Pro Val
            500                 505                 510

Glu Ser Cys Val Gln Tyr Thr Ser Cys Glu Leu Cys Leu Gly Ser Arg
        515                 520                 525

Asp Pro His Cys Gly Trp Cys Val Leu His Ser Ile Cys Ser Arg Arg
    530                 535                 540

Asp Ala Cys Glu Arg Ala Asp Glu Pro Gln Arg Phe Ala Ala Asp Leu
545                 550                 555                 560

Leu Gln Cys Val Gln Leu Thr Val Gln Pro Arg Asn Val Ser Val Thr
                565                 570                 575

Met Ser Gln Val Pro Leu Val Leu Gln Ala Trp Asn Val Pro Asp Leu
            580                 585                 590

Ser Ala Gly Val Asn Cys Ser Phe Glu Asp Phe Thr Glu Ser Glu Ser
        595                 600                 605

Val Leu Glu Asp Gly Arg Ile His Cys Arg Ser Pro Ser Ala Arg Glu
    610                 615                 620

Val Ala Pro Ile Thr Arg Gly Gln Gly Asp Gln Arg Val Val Lys Leu
625                 630                 635                 640

Tyr Leu Lys Ser Lys Glu Thr Gly Lys Lys Phe Ala Ser Val Asp Phe
```

-continued

```
                645                 650                 655
    Val Phe Tyr Asn Cys Ser Val His Gln Ser Cys Leu Ser Cys Val Asn
                    660                 665                 670
    Gly Ser Phe Pro Cys His Trp Cys Lys Tyr Arg His Val Cys Thr His
                    675                 680                 685
    Asn Val Ala Asp Cys Ala Phe Leu Glu Gly Arg Val Asn Val Ser Glu
                    690                 695                 700
    Asp Cys Pro Gln Ile Leu Pro Ser Thr Gln Ile Tyr Val Pro Val Gly
    705                 710                 715                 720
    Val Val Lys Pro Ile Thr Leu Ala Ala Arg Asn Leu Pro Gln Pro Gln
                    725                 730                 735
    Ser Gly Gln Arg Gly Tyr Glu Cys Leu Phe His Ile Pro Gly Ser Pro
                    740                 745                 750
    Ala Arg Val Thr Ala Leu Arg Phe Asn Ser Ser Leu Gln Cys Gln
                    755                 760                 765
    Asn Ser Ser Tyr Ser Tyr Glu Gly Asn Asp Val Ser Asp Leu Pro Val
                    770                 775                 780
    Asn Leu Ser Val Val Trp Asn Gly Asn Phe Val Ile Asp Asn Pro Gln
    785                 790                 795                 800
    Asn Ile Gln Ala His Leu Tyr Lys Cys Pro Ala Leu Arg Glu Ser Cys
                    805                 810                 815
    Gly Leu Cys Leu Lys Ala Asp Pro Arg Phe Glu Cys Gly Trp Cys Val
                    820                 825                 830
    Ala Glu Arg Arg Cys Ser Leu Arg His His Cys Ala Ala Asp Thr Pro
                    835                 840                 845
    Ala Ser Trp Met His Ala Arg His Gly Ser Ser Arg Cys Thr Asp Pro
    850                 855                 860
    Lys Ile Leu Lys Leu Ser Pro Glu Thr Gly Pro Arg Gln Gly Gly Thr
    865                 870                 875                 880
    Arg Leu Thr Ile Thr Gly Glu Asn Leu Gly Leu Arg Phe Glu Asp Val
                    885                 890                 895
    Arg Leu Gly Val Arg Val Gly Lys Val Leu Cys Ser Pro Val Glu Ser
                    900                 905                 910
    Glu Tyr Ile Ser Ala Glu Gln Ile Val Cys Glu Ile Gly Asp Ala Ser
                    915                 920                 925
    Ser Val Arg Ala His Asp Ala Leu Val Glu Val Cys Val Arg Asp Cys
                    930                 935                 940
    Ser Pro His Tyr Arg Ala Leu Ser Pro Lys Arg Phe Thr Phe Val Thr
    945                 950                 955                 960
    Pro Thr Phe Tyr Arg Val Ser Pro Ser Arg Gly Pro Leu Ser Gly Gly
                    965                 970                 975
    Thr Trp Ile Gly Ile Glu Gly Ser His Leu Asn Ala Gly Ser Asp Val
                    980                 985                 990
    Ala Val Ser Val Gly Gly Arg Pro Cys Ser Phe Ser Trp Arg Asn Ser
                    995                 1000                1005
    Arg Glu Ile Arg Cys Leu Thr Pro Pro Gly Gln Ser Pro Gly Ser
                    1010                1015                1020
    Ala Pro Ile Ile Ile Asn Ile Asn Arg Ala Gln Leu Thr Asn Pro
                    1025                1030                1035
    Glu Val Lys Tyr Asn Tyr Thr Glu Asp Pro Thr Ile Leu Arg Ile
                    1040                1045                1050
    Asp Pro Glu Trp Ser Ile Asn Ser Gly Gly Thr Leu Leu Thr Val
                    1055                1060                1065
```

-continued

```
Thr Gly Thr Asn Leu Ala Thr Val Arg Glu Pro Arg Ile Arg Ala
    1070            1075            1080

Lys Tyr Gly Gly Ile Glu Arg Glu Asn Gly Cys Leu Val Tyr Asn
    1085            1090            1095

Asp Thr Thr Met Val Cys Arg Ala Pro Ser Val Ala Asn Pro Val
    1100            1105            1110

Arg Ser Pro Pro Glu Leu Gly Glu Arg Pro Asp Glu Leu Gly Phe
    1115            1120            1125

Val Met Asp Asn Val Arg Ser Leu Leu Val Leu Asn Ser Thr Ser
    1130            1135            1140

Phe Leu Tyr Tyr Pro Asp Pro Val Leu Glu Pro Leu Ser Pro Thr
    1145            1150            1155

Gly Leu Leu Glu Leu Lys Pro Ser Ser Pro Leu Ile Leu Lys Gly
    1160            1165            1170

Arg Asn Leu Leu Pro Pro Ala Pro Gly Asn Ser Arg Leu Asn Tyr
    1175            1180            1185

Thr Val Leu Ile Gly Ser Thr Pro Cys Thr Leu Thr Val Ser Glu
    1190            1195            1200

Thr Gln Leu Leu Cys Glu Ala Pro Asn Leu Thr Gly Gln His Lys
    1205            1210            1215

Val Thr Val Arg Ala Gly Gly Phe Glu Phe Ser Pro Gly Thr Leu
    1220            1225            1230

Gln Val Tyr Ser Asp Ser Leu Leu Thr Leu Pro Ala Ile Val Gly
    1235            1240            1245

Ile Gly Gly Gly Gly Gly Leu Leu Leu Val Ile Val Ala Val
    1250            1255            1260

Leu Ile Ala Tyr Lys Arg Lys Ser Arg Asp Ala Asp Arg Thr Leu
    1265            1270            1275

Lys Arg Leu Gln Leu Gln Met Asp Asn Leu Glu Ser Arg Val Ala
    1280            1285            1290

Leu Glu Cys Lys Glu Ala Phe Ala Glu Leu Gln Thr Asp Ile His
    1295            1300            1305

Glu Leu Thr Asn Asp Leu Asp Gly Ala Gly Ile Pro Phe Leu Asp
    1310            1315            1320

Tyr Arg Thr Tyr Ala Met Arg Val Leu Phe Pro Gly Ile Glu Asp
    1325            1330            1335

His Pro Val Leu Lys Glu Met Glu Val Gln Ala Asn Val Glu Lys
    1340            1345            1350

Ser Leu Thr Leu Phe Gly Gln Leu Leu Thr Lys Lys His Phe Leu
    1355            1360            1365

Leu Thr Phe Ile Arg Thr Leu Glu Ala Gln Arg Ser Phe Ser Met
    1370            1375            1380

Arg Asp Arg Gly Asn Val Ala Ser Leu Ile Met Thr Ala Leu Gln
    1385            1390            1395

Gly Glu Met Glu Tyr Ala Thr Gly Val Leu Lys Gln Leu Leu Ser
    1400            1405            1410

Asp Leu Ile Glu Lys Asn Leu Glu Ser Lys Asn His Pro Lys Leu
    1415            1420            1425

Leu Leu Arg Arg Thr Glu Ser Val Ala Glu Lys Met Leu Thr Asn
    1430            1435            1440

Trp Phe Thr Phe Leu Leu Tyr Lys Phe Leu Lys Glu Cys Ala Gly
    1445            1450            1455
```

-continued

```
Glu Pro Leu Phe Met Leu Tyr Cys Ala Ile Lys Gln Gln Met Glu
    1460                1465                1470
Lys Gly Pro Ile Asp Ala Ile Thr Gly Glu Ala Arg Tyr Ser Leu
    1475                1480                1485
Ser Glu Asp Lys Leu Ile Arg Gln Gln Ile Asp Tyr Lys Thr Leu
    1490                1495                1500
Thr Leu Asn Cys Val Asn Pro Glu Asn Glu Asn Ala Pro Glu Val
    1505                1510                1515
Pro Val Lys Gly Leu Asp Cys Asp Thr Val Thr Gln Ala Lys Glu
    1520                1525                1530
Lys Leu Leu Asp Ala Ala Tyr Lys Gly Val Pro Tyr Ser Gln Arg
    1535                1540                1545
Pro Lys Ala Ala Asp Met Asp Leu Glu Trp Arg Gln Gly Arg Met
    1550                1555                1560
Ala Arg Ile Ile Leu Gln Asp Glu Asp Val Thr Thr Lys Ile Asp
    1565                1570                1575
Asn Asp Trp Lys Arg Leu Asn Thr Leu Ala His Tyr Gln Val Thr
    1580                1585                1590
Asp Gly Ser Ser Val Ala Leu Val Pro Lys Gln Thr Ser Ala Tyr
    1595                1600                1605
Asn Ile Ser Asn Ser Ser Thr Phe Thr Lys Ser Leu Ser Arg Tyr
    1610                1615                1620
Glu Ser Met Leu Arg Thr Ala Ser Ser Pro Asp Ser Leu Arg Ser
    1625                1630                1635
Arg Thr Pro Met Ile Thr Pro Asp Leu Glu Ser Gly Thr Lys Leu
    1640                1645                1650
Trp His Leu Val Lys Asn His Asp His Leu Asp Gln Arg Glu Gly
    1655                1660                1665
Asp Arg Gly Ser Lys Met Val Ser Glu Ile Tyr Leu Thr Arg Leu
    1670                1675                1680
Leu Ala Thr Lys Gly Thr Leu Gln Lys Phe Val Asp Asp Leu Phe
    1685                1690                1695
Glu Thr Ile Phe Ser Thr Ala His Arg Gly Ser Ala Leu Pro Leu
    1700                1705                1710
Ala Ile Lys Tyr Met Phe Asp Phe Leu Asp Glu Gln Ala Asp Lys
    1715                1720                1725
His Gln Ile His Asp Ala Asp Val Arg His Thr Trp Lys Ser Asn
    1730                1735                1740
Cys Leu Pro Leu Arg Phe Trp Val Asn Val Ile Lys Asn Pro Gln
    1745                1750                1755
Phe Val Phe Asp Ile His Lys Asn Ser Ile Thr Asp Ala Cys Leu
    1760                1765                1770
Ser Val Val Ala Gln Thr Phe Met Asp Ser Cys Ser Thr Ser Glu
    1775                1780                1785
His Lys Leu Gly Lys Asp Ser Pro Ser Asn Lys Leu Leu Tyr Ala
    1790                1795                1800
Lys Asp Ile Pro Asn Tyr Lys Ser Trp Val Glu Arg Tyr Tyr Ala
    1805                1810                1815
Asp Ile Ala Lys Met Pro Ala Ile Ser Asp Gln Asp Met Ser Ala
    1820                1825                1830
Tyr Leu Ala Glu Gln Ser Arg Leu His Leu Ser Gln Phe Asn Ser
    1835                1840                1845
Met Ser Ala Leu His Glu Ile Tyr Ser Tyr Ile Thr Lys Tyr Lys
```

```
                     1850                1855                1860
Asp Glu  Ile Leu Ala Ala Leu  Glu Lys Asp Glu Gln  Ala Arg Arg
         1865                1870                1875

Gln Arg  Leu Arg Ser Lys Leu  Glu Gln Val Val Asp  Thr Met Ala
         1880                1885                1890

Leu Ser  Ser
         1895

<210> SEQ ID NO 10
<211> LENGTH: 1247
<212> TYPE: PRT
<213> ORGANISM: Artificial Sequence
<220> FEATURE:
<223> OTHER INFORMATION: modified sequence of extracellular domain of
      hPlexinA1

<400> SEQUENCE: 10

Met Trp Trp Arg Leu Trp Trp Leu Leu Leu Leu Leu Leu Leu Leu Trp
1               5                   10                  15

Pro Met Val Trp Ala Glu Ala Gly Leu Pro Arg Ala Gly Gly Gly Ser
            20                  25                  30

Gln Pro Pro Phe Arg Thr Phe Ser Ala Ser Asp Trp Gly Leu Thr His
        35                  40                  45

Leu Val Val His Glu Gln Thr Gly Glu Val Tyr Val Gly Ala Val Asn
    50                  55                  60

Arg Ile Tyr Lys Leu Ser Gly Asn Leu Thr Leu Leu Arg Ala His Val
65                  70                  75                  80

Thr Gly Pro Val Glu Asp Asn Glu Lys Cys Tyr Pro Pro Pro Ser Val
                85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala
        115                 120                 125

Ser Gln Gly Ile Cys Gln Phe Leu Arg Leu Asp Asp Leu Phe Lys Leu
    130                 135                 140

Gly Glu Pro His His Arg Lys Glu His Tyr Leu Ser Ser Val Gln Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
            180                 185                 190

Phe Pro Thr Leu Ser Ser Arg Arg Leu Met Ala Asn Glu Glu Asp Ala
        195                 200                 205

Asp Met Phe Gly Phe Val Tyr Gln Asp Glu Phe Val Ser Ser Gln Leu
    210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Tyr Leu Thr Leu
                245                 250                 255

Gln Leu Asp Thr Gln Leu Thr Ser Pro Asp Ala Ala Gly Glu His Phe
            260                 265                 270

Phe Thr Ser Lys Ile Val Arg Leu Cys Val Asp Asp Pro Lys Phe Tyr
        275                 280                 285

Ser Tyr Val Glu Phe Pro Ile Gly Cys Glu Gln Ala Gly Val Glu Tyr
    290                 295                 300
```

```
Arg Leu Val Gln Asp Ala Tyr Leu Ser Arg Pro Gly Arg Ala Leu Ala
305                 310                 315                 320

His Gln Leu Gly Leu Ala Glu Asp Glu Asp Val Leu Phe Thr Val Phe
                325                 330                 335

Ala Gln Gly Gln Lys Asn Arg Val Lys Pro Lys Glu Ser Ala Leu
                340                 345                 350

Cys Leu Phe Thr Leu Arg Ala Ile Lys Glu Lys Ile Lys Glu Arg Ile
                355                 360                 365

Gln Ser Cys Tyr Arg Gly Glu Gly Lys Leu Ser Leu Pro Trp Leu Leu
370                 375                 380

Asn Lys Glu Leu Gly Cys Ile Asn Ser Pro Leu Gln Ile Asp Asp Asp
385                 390                 395                 400

Phe Cys Gly Gln Asp Phe Asn Gln Pro Leu Gly Gly Thr Val Thr Ile
                405                 410                 415

Glu Gly Thr Pro Leu Phe Val Asp Lys Asp Asp Gly Leu Thr Ala Val
                420                 425                 430

Ala Ala Tyr Asp Tyr Arg Gly Arg Thr Val Val Phe Ala Gly Thr Arg
                435                 440                 445

Ser Gly Arg Ile Arg Lys Ile Leu Val Asp Leu Ser Asn Pro Gly Gly
450                 455                 460

Arg Pro Ala Leu Ala Tyr Glu Ser Val Val Ala Gln Glu Gly Ser Pro
465                 470                 475                 480

Ile Leu Arg Asp Leu Val Leu Ser Pro Asn His Gln Tyr Leu Tyr Ala
                485                 490                 495

Met Thr Glu Lys Gln Val Thr Arg Val Pro Val Glu Ser Cys Val Gln
                500                 505                 510

Tyr Thr Ser Cys Glu Leu Cys Leu Gly Ser Arg Asp Pro His Cys Gly
                515                 520                 525

Trp Cys Val Leu His Ser Ile Cys Ser Arg Arg Asp Ala Cys Glu Arg
                530                 535                 540

Ala Asp Glu Pro Gln Arg Phe Ala Ala Asp Leu Leu Gln Cys Val Gln
545                 550                 555                 560

Leu Thr Val Gln Pro Arg Asn Val Ser Val Thr Met Ser Gln Val Pro
                565                 570                 575

Leu Val Leu Gln Ala Trp Asn Val Pro Asp Leu Ser Ala Gly Val Asn
                580                 585                 590

Cys Ser Phe Glu Asp Phe Thr Glu Ser Glu Ser Val Leu Glu Asp Gly
                595                 600                 605

Arg Ile His Cys Arg Ser Pro Ser Ala Arg Glu Val Ala Pro Ile Thr
610                 615                 620

Arg Gly Gln Gly Asp Gln Arg Val Val Lys Leu Tyr Leu Lys Ser Lys
625                 630                 635                 640

Glu Thr Gly Lys Lys Phe Ala Ser Val Asp Phe Val Phe Tyr Asn Cys
                645                 650                 655

Ser Val His Gln Ser Cys Leu Ser Cys Val Asn Gly Ser Phe Pro Cys
                660                 665                 670

His Trp Cys Lys Tyr Arg His Val Cys Thr His Asn Val Ala Asp Cys
                675                 680                 685

Ala Phe Leu Glu Gly Arg Val Asn Val Ser Glu Asp Cys Pro Gln Ile
                690                 695                 700

Leu Pro Ser Thr Gln Ile Tyr Val Pro Val Gly Val Val Lys Pro Ile
705                 710                 715                 720

Thr Leu Ala Ala Arg Asn Leu Pro Gln Pro Gln Ser Gly Gln Arg Gly
```

-continued

```
                725                 730                 735
Tyr Glu Cys Leu Phe His Ile Pro Gly Ser Pro Ala Arg Val Thr Ala
            740                 745                 750
Leu Arg Phe Asn Ser Ser Leu Gln Cys Gln Asn Ser Ser Tyr Ser
            755                 760                 765
Tyr Glu Gly Asn Asp Val Ser Asp Leu Pro Val Asn Leu Ser Val Val
            770                 775                 780
Trp Asn Gly Asn Phe Val Ile Asp Asn Pro Gln Asn Ile Gln Ala His
785                 790                 795                 800
Leu Tyr Lys Cys Pro Ala Leu Arg Glu Ser Cys Gly Leu Cys Leu Lys
            805                 810                 815
Ala Asp Pro Arg Phe Glu Cys Gly Trp Cys Val Ala Glu Arg Cys
            820                 825                 830
Ser Leu Arg His His Cys Ala Ala Asp Thr Pro Ala Ser Trp Met His
            835                 840                 845
Ala Arg His Gly Ser Ser Arg Cys Thr Asp Pro Lys Ile Leu Lys Leu
            850                 855                 860
Ser Pro Glu Thr Gly Pro Arg Gln Gly Gly Thr Arg Leu Thr Ile Thr
865                 870                 875                 880
Gly Glu Asn Leu Gly Leu Arg Phe Glu Asp Val Arg Leu Gly Val Arg
                    885                 890                 895
Val Gly Lys Val Leu Cys Ser Pro Val Glu Ser Glu Tyr Ile Ser Ala
            900                 905                 910
Glu Gln Ile Val Cys Glu Ile Gly Asp Ala Ser Ser Val Arg Ala His
            915                 920                 925
Asp Ala Leu Val Glu Val Cys Val Arg Asp Cys Ser Pro His Tyr Arg
            930                 935                 940
Ala Leu Ser Pro Lys Arg Phe Thr Phe Val Thr Pro Thr Phe Tyr Arg
945                 950                 955                 960
Val Ser Pro Ser Arg Gly Pro Leu Ser Gly Gly Thr Trp Ile Gly Ile
                    965                 970                 975
Glu Gly Ser His Leu Asn Ala Gly Ser Asp Val Ala Val Ser Val Gly
                    980                 985                 990
Gly Arg Pro Cys Ser Phe Ser Trp Arg Asn Ser Arg Glu Ile Arg Cys
            995                 1000                1005
Leu Thr Pro Pro Gly Gln Ser Pro Gly Ser Ala Pro Ile Ile Ile
     1010                1015                1020
Asn Ile Asn Arg Ala Gln Leu Thr Asn Pro Glu Val Lys Tyr Asn
     1025                1030                1035
Tyr Thr Glu Asp Pro Thr Ile Leu Arg Ile Asp Pro Glu Trp Ser
     1040                1045                1050
Ile Asn Ser Gly Gly Thr Leu Leu Thr Val Thr Gly Thr Asn Leu
     1055                1060                1065
Ala Thr Val Arg Glu Pro Arg Ile Arg Ala Lys Tyr Gly Gly Ile
     1070                1075                1080
Glu Arg Glu Asn Gly Cys Leu Val Tyr Asn Asp Thr Thr Met Val
     1085                1090                1095
Cys Arg Ala Pro Ser Val Ala Asn Pro Val Arg Ser Pro Pro Glu
     1100                1105                1110
Leu Gly Glu Arg Pro Asp Glu Leu Gly Phe Val Met Asp Asn Val
     1115                1120                1125
Arg Ser Leu Leu Val Leu Asn Ser Thr Ser Phe Leu Tyr Tyr Pro
     1130                1135                1140
```

```
Asp Pro Val Leu Glu Pro Leu Ser Pro Thr Gly Leu Leu Glu Leu
    1145                1150                1155

Lys Pro Ser Ser Pro Leu Ile Leu Lys Gly Arg Asn Leu Leu Pro
    1160                1165                1170

Pro Ala Pro Gly Asn Ser Arg Leu Asn Tyr Thr Val Leu Ile Gly
    1175                1180                1185

Ser Thr Pro Cys Thr Leu Thr Val Ser Glu Thr Gln Leu Leu Cys
    1190                1195                1200

Glu Ala Pro Asn Leu Thr Gly Gln His Lys Val Thr Val Arg Ala
    1205                1210                1215

Gly Gly Phe Glu Phe Ser Pro Gly Thr Leu Gln Val Tyr Ser Asp
    1220                1225                1230

Ser Leu Leu Thr Leu Pro Asp Tyr Lys Asp Asp Asp Asp Lys
    1235                1240                1245

<210> SEQ ID NO 11
<211> LENGTH: 213
<212> TYPE: PRT
<213> ORGANISM: Mus musculus

<400> SEQUENCE: 11

Cys Gln Pro Ser Leu Ser Leu Gln Arg Pro Ala Leu Glu Asp Leu
1               5                   10                  15

Leu Gly Ser Asp Ala Ser Ile Thr Cys Thr Leu Asn Gly Leu Arg Asn
                20                  25                  30

Pro Glu Gly Ala Ala Phe Thr Trp Glu Pro Ser Thr Gly Lys Asp Ala
                35                  40                  45

Val Gln Lys Lys Ala Ala Gln Asn Ser Cys Gly Cys Tyr Ser Val Ser
    50                  55                      60

Ser Val Leu Pro Gly Cys Ala Glu Arg Trp Asn Ser Gly Ala Ser Phe
65                  70                  75                  80

Lys Cys Thr Val Thr His Pro Glu Ser Gly Thr Leu Thr Gly Thr Ile
                    85                  90                  95

Ala Lys Val Thr Val Asn Thr Phe Pro Pro Gln Val His Leu Leu Pro
                100                 105                 110

Pro Pro Ser Glu Glu Leu Ala Leu Asn Glu Leu Leu Ser Leu Thr Cys
            115                 120                 125

Leu Val Arg Ala Phe Asn Pro Lys Glu Val Leu Val Arg Trp Leu His
    130                 135                 140

Gly Asn Glu Glu Leu Ser Pro Glu Ser Tyr Leu Val Phe Glu Pro Leu
145                 150                 155                 160

Lys Glu Pro Gly Glu Gly Ala Thr Thr Tyr Leu Val Thr Ser Val Leu
                165                 170                 175

Arg Val Ser Ala Glu Thr Trp Lys Gln Gly Asp Gln Tyr Ser Cys Met
                180                 185                 190

Val Gly His Glu Ala Leu Pro Met Asn Phe Thr Gln Lys Thr Ile Asp
            195                 200                 205

Arg Leu Ser Gly Lys
    210

<210> SEQ ID NO 12
<211> LENGTH: 233
<212> TYPE: PRT
<213> ORGANISM: Artificial Sequence
<220> FEATURE:
<223> OTHER INFORMATION: Mouse IgA-Fc linked to Avi tag
```

<400> SEQUENCE: 12

```
Cys Gln Pro Ser Leu Ser Leu Gln Arg Pro Ala Leu Glu Asp Leu Leu
1               5                   10                  15

Leu Gly Ser Asp Ala Ser Ile Thr Cys Thr Leu Asn Gly Leu Arg Asn
            20                  25                  30

Pro Glu Gly Ala Ala Phe Thr Trp Glu Pro Ser Thr Gly Lys Asp Ala
        35                  40                  45

Val Gln Lys Lys Ala Ala Gln Asn Ser Cys Gly Cys Tyr Ser Val Ser
    50                  55                  60

Ser Val Leu Pro Gly Cys Ala Glu Arg Trp Asn Ser Gly Ala Ser Phe
65                  70                  75                  80

Lys Cys Thr Val Thr His Pro Glu Ser Gly Thr Leu Thr Gly Thr Ile
                85                  90                  95

Ala Lys Val Thr Val Asn Thr Phe Pro Pro Gln Val His Leu Leu Pro
            100                 105                 110

Pro Pro Ser Glu Glu Leu Ala Leu Asn Glu Leu Leu Ser Leu Thr Cys
        115                 120                 125

Leu Val Arg Ala Phe Asn Pro Lys Glu Val Leu Val Arg Trp Leu His
130                 135                 140

Gly Asn Glu Glu Leu Ser Pro Glu Ser Tyr Leu Val Phe Glu Pro Leu
145                 150                 155                 160

Lys Glu Pro Gly Glu Gly Ala Thr Thr Tyr Leu Val Thr Ser Val Leu
                165                 170                 175

Arg Val Ser Ala Glu Thr Trp Lys Gln Gly Asp Gln Tyr Ser Cys Met
            180                 185                 190

Val Gly His Glu Ala Leu Pro Met Asn Phe Thr Gln Lys Thr Ile Asp
        195                 200                 205

Arg Leu Ser Gly Lys Gly Gly Gly Ser Gly Leu Asn Asp Ile Phe
    210                 215                 220

Glu Ala Gln Lys Ile Glu Trp His Glu
225                 230
```

<210> SEQ ID NO 13
<211> LENGTH: 8
<212> TYPE: PRT
<213> ORGANISM: Artificial Sequence
<220> FEATURE:
<223> OTHER INFORMATION: FLAG tag

<400> SEQUENCE: 13

```
Asp Tyr Lys Asp Asp Asp Asp Lys
1               5
```

<210> SEQ ID NO 14
<211> LENGTH: 26
<212> TYPE: PRT
<213> ORGANISM: Homo sapiens

<400> SEQUENCE: 14

```
Met Pro Leu Pro Pro Arg Ser Leu Gln Val Leu Leu Leu Leu Leu Leu
1               5                   10                  15

Leu Leu Leu Leu Pro Gly Met Trp Ala
            20                  25
```

<210> SEQ ID NO 15
<211> LENGTH: 21
<212> TYPE: PRT

<213> ORGANISM: Artificial Sequence
<220> FEATURE:
<223> OTHER INFORMATION: Artificial signal sequence

<400> SEQUENCE: 15

Met Trp Trp Arg Leu Trp Trp Leu Leu Leu Leu Leu Leu Leu Trp
1               5                   10                  15

Pro Met Val Trp Ala
            20

<210> SEQ ID NO 16
<211> LENGTH: 15
<212> TYPE: PRT
<213> ORGANISM: Artificial Sequence
<220> FEATURE:
<223> OTHER INFORMATION: AviTag

<400> SEQUENCE: 16

Gly Leu Asn Asp Ile Phe Glu Ala Gln Lys Ile Glu Trp His Glu
1               5                   10                  15

<210> SEQ ID NO 17
<211> LENGTH: 641
<212> TYPE: PRT
<213> ORGANISM: Epstein-Barr virus

<400> SEQUENCE: 17

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
            100                 105                 110

Gly Ala Gly Gly Ala Gly Gly Ala Gly Gly Ala Gly Ala Gly Gly Gly
        115                 120                 125

Gly Ala Gly Ala Gly Gly Ala Gly Gly Ala Gly Gly Ala Gly Ala
    130                 135                 140

Gly Gly Gly Ala Gly Ala Gly Gly Ala Gly Gly Ala Gly Ala Gly Gly
145                 150                 155                 160

Gly Gly Ala Gly Gly Ala Gly Gly Ala Gly Gly Gly Ala Gly Gly
                165                 170                 175

Ala Gly Gly Gly Ala Gly Gly Ala Gly Ala Gly Gly Ala Gly Gly
            180                 185                 190

Ala Gly Gly Ala Gly Ala Gly Gly Ala Gly Ala Gly Gly Ala Gly
        195                 200                 205

Gly Ala Gly Gly Ala Gly Ala Gly Gly Ala Gly Ala Gly Gly Ala
    210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Gly Ala Gly Ala Gly

Gly Ala Gly Gly Ala Gly Ala Gly Gly Ala Gly Gly Ala Gly
                245                 250                 255
Gly Gly Ala Gly Gly Ala Gly Ala Gly Gly Ala Gly Gly Ala Gly
            260                 265                 270
Ala Gly Gly Ala Gly Gly Ala Gly Ala Gly Gly Ala Gly Gly Ala Gly
        275                 280                 285
Ala Gly Gly Ala Gly Ala Gly Gly Ala Gly Gly Ala Gly Ala Gly
    290                 295                 300
Ala Gly Gly Ala Gly Gly Ala Gly Ala Gly Gly Ala Gly Ala Gly
305                 310                 315                 320
Gly Ala Gly Ala Gly Gly Gly Arg Gly Arg Gly Gly Ser Gly Gly
                325                 330                 335
Arg Gly Arg Gly Gly Ser Gly Gly Arg Gly Arg Gly Gly Ser Gly Gly
            340                 345                 350
Arg Arg Gly Arg Gly Arg Glu Arg Ala Arg Gly Ser Arg Glu Arg
                355                 360                 365
Ala Arg Gly Arg Gly Arg Gly Arg Gly Glu Lys Arg Pro Arg Ser Pro
    370                 375                 380
Ser Ser Gln Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
        435                 440                 445
Gly Pro Arg Gly Gln Gly Asp Gly Gly Arg Arg Lys Lys Gly Gly Trp
    450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640
Glu

<210> SEQ ID NO 18
<211> LENGTH: 321

<212> TYPE: PRT
<213> ORGANISM: Escherichia coli

<400> SEQUENCE: 18

```
Met Lys Asp Asn Thr Val Pro Leu Lys Leu Ile Ala Leu Leu Ala Asn
1               5                   10                  15

Gly Glu Phe His Ser Gly Glu Gln Leu Gly Thr Leu Gly Met Ser
            20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
        50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Gly Arg Lys Trp Phe Ser Pro Phe Gly
            115                 120                 125

Ala Asn Leu Tyr Leu Ser Met Phe Trp Arg Leu Glu Gln Gly Pro Ala
        130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
            210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

<210> SEQ ID NO 19
<211> LENGTH: 338
<212> TYPE: PRT
<213> ORGANISM: Artificial Sequence
<220> FEATURE:
<223> OTHER INFORMATION: soluble human IL-6R

<400> SEQUENCE: 19

```
Leu Ala Pro Arg Arg Cys Pro Ala Gln Glu Val Ala Arg Gly Val Leu
1               5                   10                  15
```

```
Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln
```

<210> SEQ ID NO 20
<211> LENGTH: 358
<212> TYPE: PRT
<213> ORGANISM: Artificial Sequence
<220> FEATURE:
<223> OTHER INFORMATION: soluble human IL-6R linked to Avi tag

<400> SEQUENCE: 20

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30
```

```
Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
 50                  55                  60

Arg Ser Val Gln Leu His Asp Ser Gly Asn Tyr Ser Cys Tyr Arg Ala
 65                  70                  75                  80

Gly Arg Pro Ala Gly Thr Val His Leu Leu Val Asp Val Pro Pro Glu
                 85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
                180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Gly Gly Gly Ser Gly Leu Asn Asp Ile Phe Glu Ala Gln
                340                 345                 350

Lys Ile Glu Trp His Glu
        355

<210> SEQ ID NO 21
<211> LENGTH: 448
<212> TYPE: PRT
<213> ORGANISM: Artificial Sequence
<220> FEATURE:
<223> OTHER INFORMATION: 6RNH-2_02 heavy chain

<400> SEQUENCE: 21

Gln Val Gln Leu Val Glu Thr Gly Gly Gly Met Val Gln Pro Gly Gly
1               5                   10                  15

Ser Leu Arg Leu Ser Cys Ala Ala Ser Gly Phe Met Phe Ser Thr Tyr
            20                  25                  30
```

```
Ala Met Ser Trp Val Arg Gln Ala Ser Gly Lys Gly Leu Glu Trp Val
             35                  40                  45

Ser Leu Ile Ser Gly Thr Gly Ser Val Thr Lys Tyr Ala Asp Ser Val
 50                  55                  60

Lys Gly Arg Phe Thr Ile Ser Arg Asp Asn Ser Lys Asn Met Val Tyr
 65                  70                  75                  80

Leu Gln Met Asn Asn Leu Gly Ala Asp Asp Thr Ala Val Tyr Tyr Cys
                 85                  90                  95

Ala Asn Ser Asp Tyr Gly Asp Tyr Ala Arg Phe Asp His Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
```

<210> SEQ ID NO 22
<211> LENGTH: 447
<212> TYPE: PRT
<213> ORGANISM: Artificial Sequence
<220> FEATURE:
<223> OTHER INFORMATION: 6RNH-2_37 heavy chain

<400> SEQUENCE: 22

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

```
            370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 23
<211> LENGTH: 447
<212> TYPE: PRT
<213> ORGANISM: Artificial Sequence
<220> FEATURE:
<223> OTHER INFORMATION: 6RNH-3(2)_32 heavy chain

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser His Asp
                20                  25                  30

His Ala Trp Ser Trp Val Arg Gln Pro Pro Gly Glu Gly Leu Glu Trp
                35                  40                  45

Ile Gly His Ile Ser Tyr Ser Gly Ile Thr Asn Tyr Asn Pro His Leu
            50                  55                  60

Gln Asp Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Leu Ala Arg Ile Thr Ala His Asp His Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
```

```
                290             295             300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 24
<211> LENGTH: 447
<212> TYPE: PRT
<213> ORGANISM: Artificial Sequence
<220> FEATURE:
<223> OTHER INFORMATION: 6RNH-2_42 heavy chain

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

His Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
```

```
                        210                 215                 220

Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 25
<211> LENGTH: 450
<212> TYPE: PRT
<213> ORGANISM: Artificial Sequence
<220> FEATURE:
<223> OTHER INFORMATION: PANH-2_52 heavy chaine

<400> SEQUENCE: 25

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Pro Met Glu Trp Leu Phe Trp Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
```

```
                130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
450

<210> SEQ ID NO 26
<211> LENGTH: 443
<212> TYPE: PRT
<213> ORGANISM: Artificial Sequence
<220> FEATURE:
<223> OTHER INFORMATION: PANH-2_68 heavy chain

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
```

```
            35                  40                  45
Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala His Thr Lys Asp Ile Trp Gly Gln Gly Thr Met Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 27
```

```
<211> LENGTH: 456
<212> TYPE: PRT
<213> ORGANISM: Artificial Sequence
<220> FEATURE:
<223> OTHER INFORMATION: PANH-3_10 heavy chain

<400> SEQUENCE: 27
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Val Gln Leu Glu His Ser Arg Tyr Tyr Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
370                 375                 380

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro
    450                 455

<210> SEQ ID NO 28
<211> LENGTH: 450
<212> TYPE: PRT
<213> ORGANISM: Artificial Sequence
<220> FEATURE:
<223> OTHER INFORMATION: mIANH-2_27 heavy chain

<400> SEQUENCE: 28

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Asp Thr Ala Val Tyr Tyr Cys
                85                  90                  95

Ala Arg Asp Asn Ser Gly Trp Gly Gly Phe Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 29
<211> LENGTH: 448
<212> TYPE: PRT
<213> ORGANISM: Artificial Sequence
<220> FEATURE:
<223> OTHER INFORMATION: mIANH-3_79 heavy chain

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Tyr Ser Leu Thr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

<210> SEQ ID NO 30
<211> LENGTH: 219
<212> TYPE: PRT
<213> ORGANISM: Artificial Sequence
<220> FEATURE:
<223> OTHER INFORMATION: light chain of anti-PlexinA1 antibody hPANKB2-
      3#135; sequence in which Cys at the C-terminus of the light chain
      constant region in SEQ ID NO:64 is substituted with Ala

<400> SEQUENCE: 30

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Gln Ile Ser Asn Arg Phe Ser Gly Val Pro
    50                  55                  60

Asp Arg Phe Arg Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

```
Thr His Phe Pro Trp Thr Phe Gly Gln Gly Thr Ser Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Ala
            210                 215
```

<210> SEQ ID NO 31
<211> LENGTH: 212
<212> TYPE: PRT
<213> ORGANISM: Artificial Sequence
<220> FEATURE:
<223> OTHER INFORMATION: light chain of anti-mouse IgA antibody
      mIANMIgL_095; sequence in which Cys and Ser at the C-terminus of
      the light chain constant region in SEQ ID NO:65 are substituted
      with a single Ala

<400> SEQUENCE: 31

```
Ser Tyr Glu Leu Thr Gln Pro Pro Ser Val Ser Val Ser Pro Gly Gln
1               5                   10                  15

Ser Ala Ser Ile Thr Cys Ser Gly Asp Lys Leu Gly Asp Arg Phe Val
            20                  25                  30

Thr Trp Tyr Gln Gln Lys Pro Gly Gln Ser Pro Val Leu Val Met Tyr
            35                  40                  45

Gln Asp Asn Gln Arg Pro Ser Gly Ile Pro Glu Arg Phe Ser Gly Ser
        50                  55                  60

Asn Ser Gly Asn Thr Ala Thr Leu Thr Ile Thr Gly Thr Pro Ala Met
65                  70                  75                  80

Asp Glu Ala Asp Tyr Tyr Cys Gln Thr Trp Asp Ala Gly Thr Gly Val
                85                  90                  95

Val Phe Gly Gly Gly Thr Lys Leu Thr Val Leu Ser Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Ala
    210
```

<210> SEQ ID NO 32
<211> LENGTH: 219
<212> TYPE: PRT
<213> ORGANISM: Artificial Sequence
<220> FEATURE:
<223> OTHER INFORMATION: light chain of humanized anti-CD3 antibody hCE115HA/L0000; sequence in which Cys at the C-terminus of the light chain constant region in SEQ ID NO:66 is substituted with Ala

<400> SEQUENCE: 32

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Ala
    210                 215
```

<210> SEQ ID NO 33
<211> LENGTH: 207
<212> TYPE: PRT
<213> ORGANISM: Artificial Sequence
<220> FEATURE:
<223> OTHER INFORMATION: NCBI Reference Sequence NP_000724

<400> SEQUENCE: 33

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80
```

```
His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 34
<211> LENGTH: 137
<212> TYPE: PRT
<213> ORGANISM: Artificial Sequence
<220> FEATURE:
<223> OTHER INFORMATION: prepared hCD3e

<400> SEQUENCE: 34

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Asp Tyr Lys Asp Asp Asp Lys
130                 135

<210> SEQ ID NO 35
<211> LENGTH: 447
<212> TYPE: PRT
<213> ORGANISM: Artificial Sequence
<220> FEATURE:
<223> OTHER INFORMATION: 6RmIAB3(2)_02 heavy chain

<400> SEQUENCE: 35

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Pro Pro Gly Lys Gly Leu Glu Trp
```

```
                35                  40                  45
Ile Gly Glu Ile Tyr His Gly Gly Ser Thr Asn Tyr Asn Pro Ser Leu
 50                  55                  60
Lys Ser Arg Val Thr Ile Ser Val Asp Arg Ser Lys Asn Gln Phe Ser
 65                  70                  75                  80
Leu Asn Leu Ser Ser Val Thr Ala Ala Asp Thr Ala Val Tyr Tyr Cys
                 85                  90                  95
Ala Arg Ala Pro Arg Gly Ser Tyr Arg Ile Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro
                435                 440                 445

<210> SEQ ID NO 36
```

<211> LENGTH: 448
<212> TYPE: PRT
<213> ORGANISM: Artificial Sequence
<220> FEATURE:
<223> OTHER INFORMATION: 6RmIAB3(2)_06 heavy chain

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Thr Ser
            20                  25                  30

Gly Ile Ser Trp Val Arg Gln Ala Pro Gly Gln Gly Leu Glu Trp Leu
        35                  40                  45

Gly Trp Ile Ser Pro Tyr Asn Ser Arg Thr Asn Ser Ala Gln Lys Leu
    50                  55                  60

Gln Gly Arg Val Asn Met Thr Thr Asp Thr Ser Thr Asn Thr Ala Tyr
65                  70                  75                  80

Leu Glu Leu Arg Ser Leu Thr Ser Asp Asp Thr Ala Val Tyr Tyr Cys
                85                  90                  95

Ala Arg Ala Asn Gly Asp Tyr Arg Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445
```

<210> SEQ ID NO 37
<211> LENGTH: 453
<212> TYPE: PRT
<213> ORGANISM: Artificial Sequence
<220> FEATURE:
<223> OTHER INFORMATION: 6RmIAB3(2)_16 heavy chain

<400> SEQUENCE: 37

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Leu Arg Phe Leu Glu Trp Gly Gly Pro Phe Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300
```

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro
    450

<210> SEQ ID NO 38
<211> LENGTH: 444
<212> TYPE: PRT
<213> ORGANISM: Artificial Sequence
<220> FEATURE:
<223> OTHER INFORMATION: 6RPAB3_03 heavy chain

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Asp Arg Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Gly Glu Trp Trp Gln Gly Asp Ser Trp Gly Gln Gly Thr Thr Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

```
Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
            435                 440

<210> SEQ ID NO 39
<211> LENGTH: 458
<212> TYPE: PRT
<213> ORGANISM: Artificial Sequence
<220> FEATURE:
<223> OTHER INFORMATION: 6RhCEB3(2)_10 heavy chain

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Asp Ile Leu Thr Gly Tyr Pro Asp Pro Thr Tyr
            100                 105                 110

Tyr Tyr Tyr Gly Met Asp Val Trp Gly Gln Gly Thr Met Val Thr Val
        115                 120                 125
```

Ser Ser Ala Ser Thr Lys Gly Pro Ser Val Phe Pro Leu Ala Pro Ser
            130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro
    450                 455

<210> SEQ ID NO 40
<211> LENGTH: 447
<212> TYPE: PRT
<213> ORGANISM: Artificial Sequence
<220> FEATURE:
<223> OTHER INFORMATION: anti-Plexin A1 antibody hPANKB2-3#135 Heavy
      chain

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                    20                  25                  30
Gly Ile Ser Trp Val Arg Gln Ala Pro Gly Gln Gly Leu Glu Trp Met
                35                  40                  45
Gly Trp Ile Ser Ala Tyr Asn Gly Asn Thr Asn Tyr Ala Gln Lys Leu
            50                  55                  60
Gln Gly Arg Val Thr Met Thr Thr Asp Thr Ser Thr Ser Thr Ala Tyr
 65                 70                  75                  80
Met Glu Leu Arg Ser Leu Arg Ser Asp Asp Thr Ala Val Tyr Tyr Cys
                85                  90                  95
Ala Arg Gly Gly Arg Gly Gly Asp Ala Phe Asp Ile Trp Gly Gln Gly
            100                 105                 110
Thr Met Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro
            435                 440                 445
```

<210> SEQ ID NO 41
<211> LENGTH: 451
<212> TYPE: PRT
<213> ORGANISM: Artificial Sequence
<220> FEATURE:
<223> OTHER INFORMATION: anti-mouse IgA antibody mIANMIgL_095 Heavy
      chain

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gln Val Asp Thr Met Ile Thr Asp Asp Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
```

```
                355                 360                 365
Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro
    450

<210> SEQ ID NO 42
<211> LENGTH: 450
<212> TYPE: PRT
<213> ORGANISM: Artificial Sequence
<220> FEATURE:
<223> OTHER INFORMATION: heavy chain of humanized anti-CD3 antibody
      hCE115HA/L0000

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 43
<211> LENGTH: 648
<212> TYPE: DNA
<213> ORGANISM: Artificial Sequence
<220> FEATURE:
<223> OTHER INFORMATION: nucleic acud sequence of PF1 Heavy chain (Fd)

<400> SEQUENCE: 43
caggtccaac tgcaggagag cggtccaggt cttgtgaaac ctagcgagac cctgagcctg      60
acctgcgccg tgtctggcta ctcaattagc gacgatcatg cctggagctg ggttcgccag     120
ccacctggag aaggtcttga gtggattgga tacattagtt atagtggaat cacaaactat     180
aatccatctc tcaaaggcag agtgacaata tcgagagaca ccagcaagaa ccagttcagc     240
ctgaaactca gcagcgtgac agccgccgac accgcggctt attattgtgc aagagtccta     300
gctcggatta cggctatgga ctactggggt gaaggcaccc tcgtcacagt ctcctcagcg     360
tcgaccaagg gcccatcggt attccccctg gcacccctcc tcaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaa                 648

<210> SEQ ID NO 44
<211> LENGTH: 879
<212> TYPE: DNA
<213> ORGANISM: Artificial Sequence
<220> FEATURE:
<223> OTHER INFORMATION: nucleic acid sequence of araC repressor
```

-continued

<400> SEQUENCE: 44

```
atggctgaag cgcaaaatga tccccctgctg ccgggatact cgtttaatgc ccatctggtg      60
gcgggtttaa cgccgattga ggccaacggt tatctcgatt ttttttatcga ccgaccgctg     120
ggaatgaaag gttatattct caatctcacc attcgcggtc aggggggtggt gaaaaatcag     180
ggacgagaat ttgtttgccg accgggtgat attttgctgt tcccgccagg agagattcat     240
cactacggtc gtcatccgga ggcacgcgaa tggtatcacc agtgggttta ctttcgtccg     300
cgtgcctact ggcatgaatg gcttaactgg ccgtcaatat ttgccaatac ggggttcttt     360
cgcccgatg aagcgcacca gccgcatttc agcgacctgt ttgggcaaat cattaacgcc      420
gggcaagggg aagggcgcta ttcggagctg ctggcgataa atctgcttga gcaattgtta     480
ctgcggcgca tggaagcgat taacgagtcg ctccatccac cgatggataa tcgggtacgc     540
gaggcttgtc agtacatcag cgatcacctg gcagacagca ttttgatat cgccagcgtc      600
gcacagcatg tttgcttgtc gccgtcgcgt ctgtcacatc ttttccgcca gcagttaggg     660
attagcgtct taagctggcg cgaggaccaa cgtatcagcc aggcgaagct gcttttgagc     720
accacccgga tgcctatcgc caccgtcggt cgcaatgttg gttttgacga tcaactctat     780
ttctcgcggg tatttaaaaa atgcaccggg gccagcccga gcgagttccg tgccggttgt     840
gaagaaaaag tgaatgatgt agccgtcaag ttgtcataa                             879
```

<210> SEQ ID NO 45
<211> LENGTH: 273
<212> TYPE: DNA
<213> ORGANISM: Artificial Sequence
<220> FEATURE:
<223> OTHER INFORMATION: nucleic acid sequence of modified araBAD promotor

<400> SEQUENCE: 45

```
aaaccaattg tccatattgc atcagacatt gccgtcactg cgtctttttac tggcacttct      60
cgctaaccaa accggtaacc ccgcttatta aaagcattct gtaacaaagc gggaccaaag     120
ccatgacaaa atcgcgtaac aaaagtgtct ataatcacgg cagaaaagtc cacattgatt     180
atttgcacgg cgtcacactt tgctatgcca tagcattttt atccataaga ttagcggatc     240
ctacctgacg cttttttatcg caactctcta ctg                                 273
```

<210> SEQ ID NO 46
<211> LENGTH: 26
<212> TYPE: PRT
<213> ORGANISM: Artificial Sequence
<220> FEATURE:
<223> OTHER INFORMATION: amino acid sequence of MalE signal sequence

<400> SEQUENCE: 46

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 47
<211> LENGTH: 78
<212> TYPE: DNA
<213> ORGANISM: Artificial Sequence
<220> FEATURE:
<223> OTHER INFORMATION: nucleic acid sequence of MalE signal sequence

<400> SEQUENCE: 47
atgaaaataa aaacaggtgc acgcatcctc gcattatccg cattaacgac gatgatgttt 60
tccgcctcgg cgctagcc 78

<210> SEQ ID NO 48
<211> LENGTH: 1221
<212> TYPE: DNA
<213> ORGANISM: Artificial Sequence
<220> FEATURE:
<223> OTHER INFORMATION: gene3 having a nucleic acid sequence different from that of gene3 of the helper phage

<400> SEQUENCE: 48
gctgctaccg tggaaagctg cctggcgaaa ccgcataccg aaaactcatt taccaacgtg 60
tggaaagacg ataaaaccct ggaccgctat gccaactacg aaggctgcct gtggaatgca 120
accggcgtgg ttgtctgcac gggtgatgaa cccaatgtt atggcacgtg ggttccgatt 180
ggtctggcca tcccggaaaa cgaaggcggt ggctccgaag gtggcggttc agaaggcggt 240
ggctcggaag gtggcggtac caaaccgccg aatatggcg ataccccgat tccgggttat 300
acgtacatca cccgctgga tgcacgtac ccgccgggta ccgaacagaa tccggccaac 360
ccgaatccga gtctggaaga tcccagccg ctgaacacct ttatgttcca aaacaatcgt 420
tttcgcaatc gtcagggcgc actgacggtg tataccggca cggttaccca gggtacggat 480
ccggttaaaa cctattacca gtacacgccg gtcagctcta aagcgatgta tgatgcctac 540
tggaacggca aatttcgtga ctgcgctttt catagcggtt caatgaaga tccgttcgtg 600 tgtgaatatc agggtcaaag ttccgacctg ccgcagccgc cggttaatgc aggcggtggc 660
tcaggtggcg gttcgggcgg tggcagcgaa ggtggcggta gcgaaggcgg tggctctgaa 720
ggtggcggta gtgaaggcgg tggctccggt ggcggttcag gttcgggtga ttttgactac 780
gaaaaaatgg caaacgctaa taaggcgcc atgaccgaaa acgcagatga aaatgctctg 840
cagtcagacg ctaaaggcaa actggattcg gtcgcgaccg actatggtgc ggccattgat 900
ggctttatcg gtgacgttag tggtctggcg aacggcaatg gtgccaccgg cgatttcgca 960
ggtagcaact ctcagatggc gcaagttggc gatggtgaca atagcccgct gatgaacaat 1020
ttccgccagt atctgccgtc tctgccgcaa agtgtcgaat gccgtccgtt tgtgttctca 1080
gctggcaaac cgtacgaatt ctctatcgat tgtgacaaaa tcaacctgtt ccgcggtgtg 1140
tttgcgttcc tgctgtatgt cgccaccttc atgtatgtgt tttcaacctt cgccaatatc 1200
ctgcgtaata agaatcata a 1221

<210> SEQ ID NO 49
<211> LENGTH: 219
<212> TYPE: PRT
<213> ORGANISM: Artificial Sequence
<220> FEATURE:
<223> OTHER INFORMATION: heavy chain of anti-PlexinA1 antibody hPANLB2-3_264 (Fd)

<400> SEQUENCE: 49

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Gly Tyr Ser Tyr Gly Phe Asp Tyr Trp
            100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys
    210                 215

<210> SEQ ID NO 50
<211> LENGTH: 216
<212> TYPE: PRT
<213> ORGANISM: Artificial Sequence
<220> FEATURE:
<223> OTHER INFORMATION: heavy chain of anti-PlexinA1 antibody hPANLB2-
      3_342 (Fd)

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Ala Gly Tyr Tyr Tyr Gly Met Asp Val Trp Gly Lys Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro

```
                      195                 200                 205
Ser Asn Thr Lys Val Asp Lys Lys
    210                 215

<210> SEQ ID NO 51
<211> LENGTH: 217
<212> TYPE: PRT
<213> ORGANISM: Artificial Sequence
<220> FEATURE:
<223> OTHER INFORMATION: heavy chain of anti-PlexinA1 antibody hPANLB2-
      3_359 (Fd)

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Pro Gly His Tyr Tyr Gly Met Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys
    210                 215

<210> SEQ ID NO 52
<211> LENGTH: 213
<212> TYPE: PRT
<213> ORGANISM: Artificial Sequence
<220> FEATURE:
<223> OTHER INFORMATION: PLR2H264#002 light chain

<400> SEQUENCE: 52

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Tyr Val
                20                  25                  30

Ser Trp Tyr Gln Arg Arg Pro Gly Gln Ser Pro Val Leu Val Ile Tyr
            35                  40                  45

Gln Asp Ser Lys Arg Pro Ser Gly Ile Pro Glu Arg Phe Ser Gly Ser
    50                  55                  60
```

-continued

```
Asn Ser Gly Asn Thr Ala Thr Leu Thr Ile Ser Gly Thr Gln Ser Met
 65                  70                  75                  80

Asp Glu Ala Asp Tyr Tyr Cys Gln Ala Trp Tyr Ser Ser Val Gly
                 85                  90                  95

Val Phe Gly Gly Gly Thr Arg Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

```
<210> SEQ ID NO 53
<211> LENGTH: 213
<212> TYPE: PRT
<213> ORGANISM: Artificial Sequence
<220> FEATURE:
<223> OTHER INFORMATION: PLR4H264#061 light chain

<400> SEQUENCE: 53
```

```
Ser Tyr Glu Leu Thr Gln Pro Pro Ser Val Ala Val Ser Pro Gly Gln
 1                5                  10                  15

Thr Ala Ser Ile Thr Cys Ser Gly His Lys Leu Gly Glu Lys Tyr Ala
                 20                  25                  30

Ser Trp Tyr Gln Gln Lys Pro Gly Gln Ser Pro Val Leu Val Ile Tyr
            35                  40                  45

Gln Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Val Cys
                 85                  90                  95

Val Phe Gly Thr Gly Thr Lys Val Thr Val Leu Gly Gln Pro Lys Ala
            100                 105                 110

Asn Pro Thr Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Gly Ser Pro Val Lys Ala Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205
```

Pro Thr Glu Cys Ser
    210

<210> SEQ ID NO 54
<211> LENGTH: 213
<212> TYPE: PRT
<213> ORGANISM: Artificial Sequence
<220> FEATURE:
<223> OTHER INFORMATION: PLR3H264#022 light chain

<400> SEQUENCE: 54

Ser Tyr Val Leu Thr Gln Pro Arg Ser Val Ser Val Ser Pro Gly Gln
1               5                   10                  15

Thr Thr Arg Ile Thr Cys Ser Gly Gln Asn Leu Gly Glu Lys Tyr Ile
            20                  25                  30

Ser Trp Tyr Arg Gln Lys Pro Gly Gln Ser Pro Glu Val Leu Ile Tyr
        35                  40                  45

Glu Asp Lys Arg Arg Pro Ser Gly Ile Pro Glu Arg Ile Ser Gly Ala
    50                  55                  60

Asn Ser Gly Gly Thr Ala Thr Leu Thr Ile Ser Gly Thr Gln Ala Met
65                  70                  75                  80

Asp Glu Ala Asp Tyr Phe Cys Gln Ala Trp Val Ser Ser Thr Glu Gly
                85                  90                  95

Val Phe Gly Gly Gly Thr Arg Leu Thr Val Leu Arg Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 55
<211> LENGTH: 214
<212> TYPE: PRT
<213> ORGANISM: Artificial Sequence
<220> FEATURE:
<223> OTHER INFORMATION: PLR2H342#009 light chain

<400> SEQUENCE: 55

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met

```
                65                  70                  75                  80
Asp Glu Ala Asp Tyr Tyr Cys Gln Ala Trp Asp Ser Ser Thr Ala Asp
                    85                  90                  95

Arg Val Phe Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                    165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
210

<210> SEQ ID NO 56
<211> LENGTH: 213
<212> TYPE: PRT
<213> ORGANISM: Artificial Sequence
<220> FEATURE:
<223> OTHER INFORMATION: PLR2H359#087 light chain

<400> SEQUENCE: 56

Ser Ser Glu Leu Thr Gln Pro Pro Ser Met Ser Val Ser Pro Gly Gln
1               5                   10                  15

Thr Ala Ser Ile Ser Cys Ser Gly Asp Arg Leu Gly Glu Lys Tyr Ala
                20                  25                  30

Ser Trp Tyr Gln Gln Lys Pro Gly Gln Ser Pro Val Leu Val Ile Tyr
            35                  40                  45

Gln Asp Asn Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Ile
65                  70                  75                  80

Asp Glu Ala Asp Tyr Tyr Cys Gln Ala Trp Asp Ser Asn Ser Ala Tyr
                    85                  90                  95

Val Phe Gly Thr Gly Thr Lys Val Thr Val Leu Gly Gln Pro Lys Ala
                100                 105                 110

Asn Pro Thr Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
130                 135                 140

Val Thr Val Ala Trp Lys Ala Asp Gly Ser Pro Val Lys Ala Gly Val
145                 150                 155                 160

Glu Thr Thr Lys Pro Ser Lys Gln Ser Asn Asn Lys Tyr Ala Ala Ser
                    165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
                195                 200                 205

Pro Thr Glu Cys Ser
```

-continued

```
<210> SEQ ID NO 57
<211> LENGTH: 214
<212> TYPE: PRT
<213> ORGANISM: Artificial Sequence
<220> FEATURE:
<223> OTHER INFORMATION: PLR2H359#062 light chain

<400> SEQUENCE: 57

Ser Tyr Glu Leu Thr Gln Pro Pro Ser Leu Ser Val Ser Pro Gly Gln
1               5                   10                  15

Thr Ala Ser Ile Thr Cys Ser Gly Asp Lys Leu Gly Glu Lys Tyr Ala
            20                  25                  30

Cys Trp Tyr Gln Gln Lys Pro Gly Gln Ser Pro Ala Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Ser Cys Gln Ala Trp Asp Thr Asn Thr Gly Glu
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 58
<211> LENGTH: 450
<212> TYPE: PRT
<213> ORGANISM: Artificial Sequence
<220> FEATURE:
<223> OTHER INFORMATION: hPANLB2-3_264 heavy chain

<400> SEQUENCE: 58

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80
```

Gln Phe Ser Leu Gln Leu Asn Ser Val Thr Pro Glu Asp Thr Ala Val
                85                  90                  95

Tyr Tyr Cys Ala Arg Asp Arg Gly Tyr Ser Tyr Gly Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
            435                 440                 445

Ser Pro
    450

<210> SEQ ID NO 59
<211> LENGTH: 447
<212> TYPE: PRT
<213> ORGANISM: Artificial Sequence
<220> FEATURE:
<223> OTHER INFORMATION: hPANLB2-3_342 heavy chain

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg His Ala Gly Tyr Tyr Gly Met Asp Val Trp Gly Lys Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                        405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 60
<211> LENGTH: 448
<212> TYPE: PRT
<213> ORGANISM: Artificial Sequence
<220> FEATURE:
<223> OTHER INFORMATION: hPANLB2-3_359 heavy chain

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Pro Gly His Tyr Tyr Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
            325                 330                 335
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445
```

<210> SEQ ID NO 61
<211> LENGTH: 213
<212> TYPE: PRT
<213> ORGANISM: Artificial Sequence
<220> FEATURE:
<223> OTHER INFORMATION: hPANLB2-3_264 light chain

<400> SEQUENCE: 61

```
Ser Tyr Leu Leu Thr Gln Pro Pro Ser Val Ser Val Ser Pro Gly Gln
1               5                   10                  15

Thr Ala Ser Ile Thr Cys Ser Gly Asp Lys Leu Gly Gln Lys Phe Val
            20                  25                  30

Ser Trp Tyr Gln Gln Arg Pro Gly Gln Ser Pro Val Leu Val Ile Tyr
            35                  40                  45

Gln Asp Thr Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Gly
            85                  90                  95

Val Phe Gly Gly Gly Thr Asn Leu Thr Val Leu Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
            165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
        210
```

<210> SEQ ID NO 62
<211> LENGTH: 213
<212> TYPE: PRT

<213> ORGANISM: Artificial Sequence
<220> FEATURE:
<223> OTHER INFORMATION: hPANLB2-3_342 light chain

<400> SEQUENCE: 62

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Glu Lys Tyr Ala
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Met Ala Thr Leu Thr Ile Ser Gly Thr Gln Ala Val
65                  70                  75                  80

Asp Glu Ala Asp Tyr Tyr Cys Gln Thr Trp Asp Ser Asn Thr Ala Phe
                85                  90                  95

Val Phe Gly Thr Gly Thr Lys Val Thr Val Leu Gly Gln Pro Lys Ala
            100                 105                 110

Asn Pro Thr Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Gly Ser Pro Val Lys Ala Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 63
<211> LENGTH: 213
<212> TYPE: PRT
<213> ORGANISM: Artificial Sequence
<220> FEATURE:
<223> OTHER INFORMATION: hPANLB2-3_359 light chain

<400> SEQUENCE: 63

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Val Gly Glu Lys Tyr Ala
            20                  25                  30

Ser Trp Tyr Gln Gln Arg Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Ile
65                  70                  75                  80

Asp Asp Ala Asp Tyr Tyr Cys Gln Ala Trp Asp Asn Ser Ala Tyr Val
                85                  90                  95

Ile Phe Gly Gly Gly Thr Lys Leu Thr Val Leu Gly Gln Pro Lys Ala
            100                 105                 110

```
Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210

<210> SEQ ID NO 64
<211> LENGTH: 219
<212> TYPE: PRT
<213> ORGANISM: Artificial Sequence
<220> FEATURE:
<223> OTHER INFORMATION: light chain of anti-PlexinA1 antibody hPANKB2-
      3#135

<400> SEQUENCE: 64

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Gln Ile Ser Asn Arg Phe Ser Gly Val Pro
    50                  55                  60

Asp Arg Phe Arg Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Phe Pro Trp Thr Phe Gly Gln Gly Thr Ser Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 65
<211> LENGTH: 213
<212> TYPE: PRT
<213> ORGANISM: Artificial Sequence
```

```
<220> FEATURE:
<223> OTHER INFORMATION: light chain of anti-mouse IgA antibody
      mIANMIgL_095

<400> SEQUENCE: 65

Ser Tyr Glu Leu Thr Gln Pro Pro Ser Val Ser Val Ser Pro Gly Gln
1               5                   10                  15

Ser Ala Ser Ile Thr Cys Ser Gly Asp Lys Leu Gly Asp Arg Phe Val
            20                  25                  30

Thr Trp Tyr Gln Gln Lys Pro Gly Gln Ser Pro Val Leu Val Met Tyr
        35                  40                  45

Gln Asp Asn Gln Arg Pro Ser Gly Ile Pro Glu Arg Phe Ser Gly Ser
50                  55                  60

Asn Ser Gly Asn Thr Ala Thr Leu Thr Ile Thr Gly Thr Pro Ala Met
65                  70                  75                  80

Asp Glu Ala Asp Tyr Tyr Cys Gln Thr Trp Asp Ala Gly Thr Gly Val
                85                  90                  95

Val Phe Gly Gly Gly Thr Lys Leu Thr Val Leu Ser Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 66
<211> LENGTH: 219
<212> TYPE: PRT
<213> ORGANISM: Artificial Sequence
<220> FEATURE:
<223> OTHER INFORMATION: light chain of humanized anti-CD3 antibody
      hCE115HA/L0000

<400> SEQUENCE: 66

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 67
<211> LENGTH: 214
<212> TYPE: PRT
<213> ORGANISM: Artificial Sequence
<220> FEATURE:
<223> OTHER INFORMATION: amino acid sequence of PF1 light chain

<400> SEQUENCE: 67

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 68
<211> LENGTH: 447
<212> TYPE: PRT
<213> ORGANISM: Artificial Sequence
<220> FEATURE:
<223> OTHER INFORMATION: amino acid sequence of PF1 heavy chain

<400> SEQUENCE: 68

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
        435                 440                 445
```

The invention claimed is:

1. A method for preparing a plurality of multispecific antigen-binding molecules comprising common first polypeptides, wherein the method comprises:
   (a) carrying out for a plurality of different antigens a method for obtaining an antigen-binding molecule specifically binding to a predetermined antigen, wherein the method comprises the steps (a-1) and (a-2) below,
      (a-1) contacting the antigen with an antigen-binding molecule display library prepared by a method for preparing an antigen-binding molecule display library comprising common first polypeptides, wherein the method comprises the steps (1) and (2) below,
         (1) carrying out a plurality of times a method for preparing a bacteriophage displaying an antigen-binding molecule, comprising contacting a helper phage capable of expressing a first polypeptide with a bacterium capable of expressing a second polypeptide, wherein the first polypeptide and the second polypeptide associate with each other to form the antigen-binding molecule, wherein a plurality of bacteria used in the step are a bacterium population capable of expressing a plurality of second polypeptides differing in amino acid sequence, and helper phages used in the step are helper phages capable of expressing first polypeptides having identical amino acid sequences; and
         (2) recovering a plurality of bacteriophages displaying antigen-binding molecules prepared in (1); and
      (a-2) selecting an antigen-binding molecule binding to the antigen from the antigen-binding molecule display library; and
   (b) preparing a multispecific antigen-binding molecule using a plurality of the first polypeptides having identical amino acid sequences and a plurality of the second polypeptides having different amino acid sequences, contained in a plurality of antigen-binding molecules obtained in (a),
   wherein the first polypeptides associate with the plurality of second polypeptides, respectively, to form the plurality of antigen-binding sites specifically binding to the plurality of antigens.

2. A method for preparing a multispecific antigen-binding molecule comprising common first polypeptides, wherein the method comprises:
   (a) carrying out for a plurality of different antigens a method for obtaining an antigen-binding molecule specifically binding to a predetermined antigen, wherein the method comprises the steps (a-1) and (a-2) below,
      (a-1) contacting the antigen with an antigen-binding molecule display library prepared by a method for preparing an antigen-binding molecule display library comprising common first polypeptides, wherein the method comprises the steps (1) and (2) below,
         (1) carrying out a plurality of times a method for preparing a bacteriophage displaying an antigen-binding molecule, comprising contacting a helper phage capable of expressing a first polypeptide with a bacterium capable of expressing a second polypeptide, wherein the first polypeptide and the second polypeptide associate with each other to form the antigen-binding molecule, wherein a plurality of bacteria used in the step are a bacterium population capable of expressing a plurality of second polypeptides differing in amino acid sequence, and helper phages used in the step are helper phages capable of expressing first polypeptides having identical amino acid sequences; and
         (2) recovering a plurality of bacteriophages displaying antigen-binding molecules prepared in (1); and
      (a-2) selecting an antigen-binding molecule binding to the antigen from the antigen-binding molecule display library;
   (b) for a plurality of first polypeptides having identical amino acid sequences and a plurality of second polypeptides having different amino acid sequences, contained in a plurality of antigen-binding molecules obtained in (a), separately preparing polynucleotides encoding the first polypeptides and polynucleotides encoding the plurality of second polypeptides;
   (c) transferring each the polynucleotide prepared in (b) to a host cell; and
   (d) culturing the host cell of (c) to recover a multispecific antigen-binding molecule, wherein the first polypeptides associate with the plurality of second polypeptides, respectively, to form the plurality of antigen-binding sites specifically binding to the plurality of antigens.

3. The method according to claim 1, wherein the multispecific antigen-binding molecule is a bispecific antigen-binding molecule.

4. The method according to claim 2, wherein the multispecific antigen-binding molecule is a bispecific antigen-binding molecule.

5. The method according to claim 2, wherein a polynucleotide encoding the first polypeptide is inserted in the genome of the helper phage.

6. The method according to claim 2, wherein the polynucleotide encoding the first polypeptide is functionally linked to a promoter.

7. The method according to claim 2, wherein the first polypeptide is fused with a phage coat protein.

8. The method according to claim 2, wherein the helper phage is M13KO7.

9. The method according to claim 2, wherein the bacterium comprises a polynucleotide encoding the second polypeptide.

10. The method according to claim 2, wherein the polynucleotide encoding the second polypeptide is inserted in a phagemid vector.

11. The method according to claim 2, wherein the second polypeptide is fused with a phage coat protein.

12. The method according to claim 2, wherein the antigen-binding molecule has antibody variable region(s).

13. The method according to claim 12, wherein the first polypeptide and the second polypeptide are each selected from the group consisting of a polypeptide comprising an L chain variable region and a polypeptide comprising an H chain variable region, and differ from each other.

14. The method according to claim 13, wherein the polypeptide comprising an L chain variable region is the polypeptide further comprising an L chain constant region, and/or the polypeptide comprising an H chain variable region is the polypeptide further comprising an H chain constant region.

* * * * *